(12) United States Patent
Pancholi

(10) Patent No.: US 11,318,141 B2
(45) Date of Patent: May 3, 2022

(54) METHODS AND COMPOSITIONS RELATED TO STK1-TARGETED SMALL MOLECULES AS ANTIBIOTIC RESISTANCE BREAKERS

(71) Applicant: Ohio State Innovation Foundation, Columbus, OH (US)

(72) Inventor: Vijay Pancholi, Dublin, OH (US)

(73) Assignee: Ohio State innovation Foundation, Columbus, OH (US)

( * ) Notice: Subject to any disclaimer, the term of this patent is extended or adjusted under 35 U.S.C. 154(b) by 5 days.

(21) Appl. No.: 16/627,575

(22) PCT Filed: Jul. 2, 2018

(86) PCT No.: PCT/US2018/040602
§ 371 (c)(1),
(2) Date: Dec. 30, 2019

(87) PCT Pub. No.: WO2019/006459
PCT Pub. Date: Jan. 3, 2019

(65) Prior Publication Data
US 2020/0222416 A1 Jul. 16, 2020

Related U.S. Application Data

(60) Provisional application No. 62/527,589, filed on Jun. 30, 2017, provisional application No. 62/528,266, filed on Jul. 3, 2017.

(51) Int. Cl.
*A61K 31/545* (2006.01)
*A61P 31/04* (2006.01)
*A61K 31/519* (2006.01)

(52) U.S. Cl.
CPC .......... *A61K 31/545* (2013.01); *A61K 31/519* (2013.01); *A61P 31/04* (2018.01)

(58) Field of Classification Search
CPC .................................................. A61K 31/545
USPC ......................................................... 514/200
See application file for complete search history.

(56) References Cited

U.S. PATENT DOCUMENTS

| | | | |
|---|---|---|---|
| 8,252,841 B2 | 8/2012 | Sperandio et al. | |
| 2009/0325944 A1 * | 12/2009 | Walker Kahne | C07D 239/60 514/227.2 |

OTHER PUBLICATIONS

Parkhomenko et al., ARKIVOC (Gainsville, FL, US (2005), vol. 8, pp. 82-88.*
International Search Report and Written Opinion issued by the International Searching Authority (ISA/US) in PCT Application No. PCT/US2018/040602 dated Aug. 28, 2018. 30 pages.
Pubchem MLS000094740. Aug. 16, 2005.
Pubchem CCG-199209. Aug. 2, 2011.
Pubchem CCG-175227. Aug. 2, 2011.
Pubchem EU-0027235. Mar. 30, 2007.
Boudreau, Marc A., et al. "Phosphorylation of BlaR1 in manifestation of antibiotic resistance in methicillin-resistant *Staphylococcus aureus* and its abrogation by small molecules." ACS infectious diseases 1.10 (2015): 454-459.
Tomić, Katarina, Jörg Tatchen, and Christel M. Marian. "Quantum chemical investigation of the electronic spectra of the keto, enol, and keto-imine tautomers of cytosine." The Journal of Physical Chemistry A 109.37 (2005): 8410-8418.
Agarwal, S., Agarwal,S., Pancholi,P., & Pancholi,V. Role of Serine/threonine phosphatase (SP-STP) in *Streptococcus pyogenes* physiology and virulence. J. Biol. Chem. 286, 41368-41380 (2011).
Agarwal, S., Agarwal,S., Pancholi,P., & Pancholi,V. Strain-specific regulatory role of eukaryote-like serine/threonine phosphatase in pneumococcal adherence. Infect. Immun. 80, 1361-1392 (2012).
Appelbaum,P.C. The emergence of vancomycin-intermediate and vancomycin-resistant *S. aureus*. Clin. Microbiol. Infect. 12(S-1), 16-23 (2006).
Arnaud, M., A. Chastanet, and M. Debarbouille. 2004. New vector for efficient allelic replacement in naturally nontransformable, low-GC-content, gram-positive bacteria. Appl. Environ. Microbiol. 70:6887-6891.
Asif, M. Chemical cheracteristics, synthetic methods, and biological potential of quinazoline and quinazoline derivatives. Int. J. Med. Chem. 395637, 1-27 (2014).
Bae, T., and O. Schneewind. 2006. Allelic replacement in *Staphylococcus aureus* with inducible counter-selection. Plasmid 55:58-63.
Beier,D. & Gross,R. Regulation of bacterial virulence by two-component systems. Curr Opin Microbiol 9, 143-152 (2006).
Beltramini,A.M., Mukhopadhyay,C.D., & Pancholi,V. Modulation of cell wall structure and antimicrobial susceptibility by a *Staphylococcus aureus* eukaryotic-like serine/threonine kinase and phosphatase. Infect. Immun. 77, 1406-1416 (2009).
Bjarnsholt,T., Ciofu,O., Molin,S., Givskov,M., & Høiby,N. Applying insights from biofilm biology to drug development—Can a new approach be developed? Nat Rev. Drug Discov. 12, 791-808 (2013).
Bossemeyer,D. The glycine-rich sequence of protein kinases: a multifunctional element. Trends Biochem. Sci. 19, 201-205 (1994).
Boucher,H.W. & Sakoulas,G. Perspectives on Daptomycin resistance, with emphasis on resistance in *Staphylococcus aureus*. Clin. Infect Dis. 45, 601-608 (2007).
Brown,D. Antibiotic resistance breakers: can repurposed drugs fill the antibiotic discovery void? Nat. Rev. Drug Discov. 14, 821-832 (2015).
Bugrysheva,J., Froehlich,B.J., Freiberg,J.A., & Scott,J.R. Serine/Threonine protein kinase Stk is required for virulence, stress response and penicillin tolerance in *Streptococcus pyogenes*. Infect. Immun. 79, 4201-4209 (2011).
Burnside,K. et al. Regulation of hemolysin expression and virulence of *Staphylococcus aureus* by a serine/threonine kinase and phosphatase. PLoS One 5, e11071 (2010).

(Continued)

*Primary Examiner* — Taofiq A Solola
(74) *Attorney, Agent, or Firm* — Meunier Carlin & Curfman LLC

(57) ABSTRACT

Disclosed are methods and compositions related to STK1 inhibitors, such as Inh2-B1 (methyl 5-oxo-3-(phenyl carbamoyl)-1-thioxo-4,5dihydro[1,3]thiazolo[3,4-a]quinazoline-8-carboxylate). The STK1 inhibitors can act as an antibiotic resistance breakers against multidrug-resistant *Staphylococcus aureus*.

12 Claims, 18 Drawing Sheets

Specification includes a Sequence Listing.

(56) References Cited

OTHER PUBLICATIONS

Cameron,D.R. et al. Serine/threonine phosphatase Stp1 contributes to reduced susceptibility to vancomycin and virulence in *Staphylococcus aureus*. J. Infect. Dis. 205, 1677-1687 (2012).
Cameron,D.R., Howden,B.P., & Peleg,A.Y. The interface between antibiotic resistance and virulence in *Staphylococcus aureus* and its impact upon clinical outcomes. Clin. Infect. Dis. 53, 576-582 (2011).
Canova,M.J. et al. A novel mode of regulation of the *Staphylococcus aureus* vancomycin-resistance-associated response regulator VraR mediated by Stk1 protein phosphorylation. Biochem. Biophys. Res. Commun. 447, 165-171 (2014).
Chawla,Y. et al. Protein kinase B (PknB) of *Mycobacterium* tuberculosis is essential for growth of the pathogen in vitro as well as for survival within the host. J. Biol. Chem. 289, 13858-13875 (2014).
Cheung, A.L., Bayer, A.S., Zhang, G., Gresham ,H., Xiong,Y.Q. Regulation of virulence determinant in vitro and in vivo in *S. aureus*. FEMS Med. Micobiol. 40, 1-9 (2004).
Cheung,A. & Duclos,B. Stp1 and Stk1: the Yin and Yang of vancomycin sensitivity and virulence in vancomycin-intermediate *Staphylococcus aureus* strains. J. Infect. Dis. 205, 1625-1627 (2012).
Debarbouille, M. et al. Characterization of serine/ threonine kinase involved in virulence of *Staphylococcus aureus*. J. Bacteriol. 191, 4070-4081 (2009).
Delaune,A. et al. Peptidoglycan cross-linking relaxation plays an important role in *Staphylococcus aureus* WalKR-dependent cell viability. PLoS One 6, e17054 (2011).
Donat,S. et al. Transcriptome and functional analysis of the eukaryotic-type serine/threonine kinase PknB in *Staphylococcus aureus*. J Bacteriol 191, 4056-4069 (2009).
Dubrac,S., Bisicchia,P., Devine,K.M., & Msadek,T. A matter of life and death:cell wall homeostasis and the WalKR(YycGF) essential signal transduction pathway. Mol. Microbiol. 70, 1307-1322 (2008).
Dubrac,S., Boneca,I.G., Poupel,O., & Msadek,T. New insights into the WalK/WalR (YycG/YycF) essential signal transduction pathway reveal a major role in controlling cell wall metabolism and biofilm formation in *Staphylococcus aureus*. J Bacteriol 189, 8257-8269 (2007).
Dworkin,J. Ser/Thr phosphorylation as a regulatory mechanism in bacteria. Curr. Opin. Microbiol. 24, 47-52 (2015).
Dworkin,J. The Medium is the message: Interspecies and interkingdom signaling by peptidoglycan and related bacterial glycans. Annu. Rev. Microbiol. 68, 137-154 (2014).
Fisher,J.F., Meroueh,S.O., & Mobashery,S. Bacterial resistance to beta-lactam antibiotics: compelling opportunism, compelling opportunity. Chem. Rev. 105, 395-424 (2005).
Fridman,M. et al. Two unique phosphorylation-driven signaling pathways crosstalk in *Staphylococcus aureus* to modulate the cell-wall charge: Stk1/Stp1 meets GraSR. Biochemistry 52, 7975-7986 (2013).
Gao,R., Mack,T.R., & Stock,A.M. Bacterial response regulators: Versatile regulatory strategies from common domains. Trends Biochem. Sci. 32, 225-234 (2007).
Groisman,E.A. & Mouslim,C. Sensing by bacterial regulatory systems in host and non-host environments. Nat. Rev. Microbiol. 4, 705-709 (2006).
Hauser,A.R., Mecsas,J., & Moir,D.T. Beyond Antibiotics: New Therapeutic Approaches for Bacterial Infections. Clin. Infect. Dis. 63, 89-95 (2016).
Hede, K. An infectious arm race. Nature 509, S2-S3 (2014).
Horstmann,N. et al. Dual-site phosphorylation of the control of virulence regulator impacts group a streptococcal global gene expression and pathogenesis. PLoS. Pathog. 10, e1004088 (2014).
Humphrey,K., Dalke,A., & Schulten,K. VMD—Visual Molecular Dynamics. J. Molec. Graphics 14, 33-38 (1996).
Irwin,J.J., Sterling,T., Mysinger,M.M., Bolstad,E.S., & Coleman,R.G. ZINC: A free tool to discover chemistry for biology. J. Chem. Inf. Model. 52, 1757-1768 (2012).
Jin, H. and Pancholi, V. 2006. Identification and biochemical characterization of a eukaryotictype serine/threonine kinase and its cognate phosphatase in *Streptococcus pyogenes*:Their biological functions and substrate identification. J. Mol. Biol. 357:1351-1372.
Leiba,J. et al. A novel mode of regulation of the *Staphylococcus aureus* catabolite control protein A (CcpA) mediated by Stk1 protein phosphorylation. J. Biol. Chem. 287, 43607-43619 (2012).
Libby,E.A., Goss,L.A., & Dworkin,J. The eukaryotic-like Ser/Thr kinase PrkC regulates the essential WalRK two-component system in Bacillus subtilis. PLoS. Genet. 11, e1005275 (2015).
Liebeke,M., Meyer,H., Donat,S., Ohlsen,K., & Lalk,M. A metabolomic view of *Staphylococcus aureus* and its ser/thr kinase and phosphatase deletion mutants: involvement in cell wall biosynthesis. Chem. Biol. 17, 820-830 (2010).
Lipinski,C.A., Lombardo,F., Dominy,B.W., & Feeney,P.J. Experimental and computational approaches to estimate soubility and permeability in drug discovery and development settlings. Adv. Drug Deliv. Rev. 1-3, 3-26 (2001).
Liu,M. et al. Defects in ex vivo and in vivo growth and sensitivity to osmotic stress of group A *Streptococcus* caused by interruption of response regulator gene vicR. Microbiology 152, 967-978 (2006).
Lowder,B.V. et al. Recent human-to-poultry host jump, adaptation, and pandemic spread of *Staphylococcus aureus*. Proc. Natl. Acad. Sci. U. S. A 106, 19545-19550 (2009).
May,M. Time for team work. Nature 509, S4-S5 (2014).
Morris,G.M. et al. AutoDock4 and AutoDockTools4: Automated docking with selective receptor flexibility. J. Comput. Chem. 30, 2785-2791 (2009).
Najera, I. et al. Focused research in different approaches to antibiotic resistance: Roche's re-entry into antibiotics. Nature 509, S18-S22 (2014).
Ng,W.L. et al. Constitutive expression of PcsB suppresses the requirement for the essential VicR (YycF) response regulator in *Streptococcus pneumoniae* R6. Mol. Microbiol. 50, 1647-1663 (2003).
Otto,M. Staphylococcal biofilms. Curr. Top. Microbiol. Immunol. 322, 207-228 (2008).
Pancholi,V., Boël,G., & Jin,H. *Streptococcus pyogenes* Ser/Thr kinase-regulated cell wall hydrolase is a cell division plane-recognizing and chain-forming virulence factor. J. Biol. Chem. 285, 30861-30874 (2010).
Parkhomenko,O.O., Kovalenko,S.M., Cherynykh,V.P., & Osolodchenko,T.P. Synthesis,and antimicrobial activity of 5-oxo-1-thioxo-4,5-dihydro[1,3]thiazolo[3,4-a]quinazolines. ARKIVOC VIII, 82-88 (2005).
Passalacqua,K.D., Satola,S.W., Crispell,E.K., & Read,T.D. A mutation in the PP2C phosphatase gene in a *Staphylococcus aureus* USA300 clinical isolate with reduced susceptibility to vancomycin and daptomycin. Antimicrob. Agents Chemother. 56, 5212-5223 (2012).
Peleg,A.Y. et al. Whole genome characterization of the mechanisms of daptomycin resistance in clinical and laboratory derived isolates of *Staphylococcus aureus*. PLoS. One. 7, e28316 (2012).
Pereira,S.F.F., Goss,L., & Dworkin,J. Eukaryote-like Serine/Threonine kinases and phosphatases in bacteria. Microbiol. Mol. Biol. Rev. 75, 192-212 (2011).
Rakette,S., Donat,S., Ohlsen,K., & Stehle,T. Structural analysis of *Staphylococcus aureus* serine/threonine kinase PknB. PLoS. One. 7, e39136 (2012).
Richter,S.G. et al. Small molecule inhibitor of lipoteichoic acid synthesis is an antibiotic for Gram positive bacteris. Proc. Natl. Acad. Sci. U. S. A. 110, 3531-3556 (2013).
Ruer,S., Pinotsis,N., Steadman,D., Waksman,G., & Remaut,H. Virulence-targeted Antibacterials: Concept, promise, and susceptibility to resistance Mechanisms. Chem. Biol. Drug Des 86, 379-399 (2015).
Sanchez Garcia,M. et al. Clinical outbreak of linezolid-resistant *Staphylococcus aureus* in an intensive care unit. JAMA 303, 2260-2264 (2010).
Sarste,M., Sibbald,P.R., & Wittinghofer,A. The P-loop-a common motif in ATP and GTP-binding proteins. Trends Biochem. Sci. 19, 430-434 (1990).
Schreiber,M., Res,I., & Matter,A. Protein kinases as antibacterial targets. Curr. Opin. Cell. Biol. 21, 325-330 (2009).

(56) References Cited

OTHER PUBLICATIONS

Sievert,D.M. et al. Vancomycin-resistant *S. aureus* in the United States, 2002-2006. Clin. Inf. Dis. 46, 668-674 (2008).

Stewart,P.S. Prospects for Anti-Biofilm Pharmaceuticals. Pharmaceuticals. (Basel) 8, 504-511 (2015).

Stock,A.M., Robinson,V.L., & Goudreau,P.N. Two-component signal transduction. Annu. Rev. Biochem. 69, 183-215 (2000).

Sun,F. et al. Protein cysteine phosphorylation of SarA/MgrA family transcriptional regulators mediates bacterial virulence and antibiotic resistance. Proc. Natl. Acad. Sci. U. S. A 109, 15461-15466 (2012).

Tamber,S., Schwartzman,J., & Cheung,A.L. Role of PknB kinase in antibiotic resistance and virulence in Community-acquired methicillin-resistant *Staphylococcus aureus* strain USA300. Infect. Immun. 78, 3637-3646 (2010).

Truong-Bolduc,Q.C. & Hooper,D.C. Phosphorylation of MgrA and its effect on expression of the NorA and NorB efflux pumps of *Staphylococcus aureus*. J Bacteriol 192, 2525-2534 (2010).

Truong-Bolduc,Q.C., Ding,Y., & Hooper,D.C. Posttranslational modification influences the effects of MgrA on norA expression in *Staphylococcus aureus*. J. Bacteriol. 190, 7375-7381 (2008).

Vornhagen,J. et al. Kinase inhibitors that increase the sensitivity of methicillin resistant *Staphylococcus aureus* to beta-Lactam Antibiotics. Pathogens. 4, 708-721 (2015).

Walburger,A. et al. Protein kinase G from pathogenic mycobacteria promotes survival within macrophages. Science 304, 1800-1804 (2004).

Wang,D. & Gao,F. Quinazoline derivatives:synthesis and bioactivities. Chem. Central J, 7, 95 (2013).

Wang,R. et al. Identification of novel cytolytic peptides as key virulence determinants for community-associated MRSA. Nature Med. 13, 1510-1514 (2007).

Wehenkel,A. et al. Mycobacterial ser/thr protein kinases and phosphatases: physiological roles and therapeutic potential. Biochimica et Biophysica Acta 1784, 193-202 (2008).

Wilen, S.H. Tables of Resolving Agents and Optical Resolutions p. A268.

Wilen, Samuel H., André Collet, and Jean Jacques. "Strategies in optical resolutions." Tetrahedron 33.21 (1977): 2725-2736.

Wyckoff,T.J., Taylor,J.A., & Salama,N.R. Beyond growth: novel functions for bacterial cell wall hydrolases. Trends Microbiol. 20, 540-547 (2012).

Young,T.A., Delagoutte,B., Endrizzi,J.A., Falick,A.M., & Alber,T. Structure of *Mycobacterium* tuberculosis PknB supports a universal activation mechanism for Ser/Thr protein kinases. Nat. Struct. Biol. 10, 168-174 (2003).

International Preliminary Report on Patentability issued for Application No. PCT/US2018/040602, dated Jan. 9, 2020.

\* cited by examiner

A

N-(3,5-dimethylphenyl)-2(3,5-dimethylpyrazol-1-yl)-6-methyl pyrimidine -4 amine

| Compounds | Structure | Binding Energy (kcal/mol) | No. of Conformers |
|---|---|---|---|
| ANP | 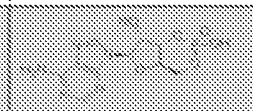 | -9.53 | 46 |
| Inh2-lead | 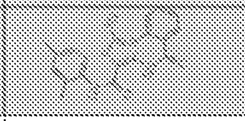 | -10.04 | 68 |
| A1 | 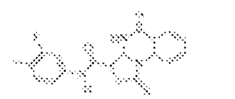 | -9.86 | 31 |
| A2 | 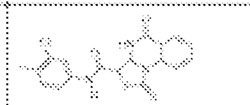 | -10.36 | 77 |
| A4 | 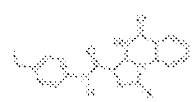 | -10.23 | 41 |
| A5 | 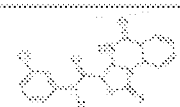 | -9.93 | 89 |
| A6 | 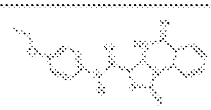 | -9.89 | 37 |
| A7 | 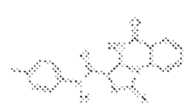 | -10.80 | 66 |
| A8 | 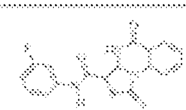 | -9.53 | 28 |
| B1 | 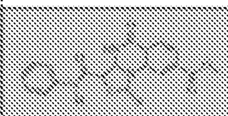 | -11.58 | 21 |
| B2 | 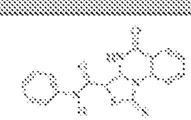 | -8.78 | 32 |

A

Ceftriaxone (µM)

| 151 | 75.5 | 37.8 | 18.9 | 9.4 | 4.7 | 2.36 | 1.18 | 0.59 | 0.3 | 0.15 |

Ceftriaxone (µg/ml)

| Inh2-B1 (µM) | | 1 | 2 | 3 | 4 | 5 | 6 | 7 | 8 | 9 | 10 | 11 | 12 |
|---|---|---|---|---|---|---|---|---|---|---|---|---|---|
| | | | 100 | 50 | 25 | 12.5 | 6.3 | 3.1 | 1.6 | 0.78 | 0.4 | 0.2 | 0.1 |
| | A | 23+3** | 0 | 12 | 22 | 22 | 21 | 20 | 22 | 20 | 20 | 19 | 20 |
| | B | 100 | 0 | 0 | 0 | 0 | 0 | 0 | 0 | 0 | 0 | 0 | 0 |
| | C | 50 | 7 | 0 | 0 | 0 | 0 | 0 | 0 | 0 | 0 | 0 | 1 | 3 |
| | D | 25 | 16 | 0 | 6* | 10 | 14 | 17 | 15 | 14 | 15 | 14 | 16 | 13 |
| | E | 12.5 | 22 | 0 | 14* | 17 | 17 | 17 | 20 | 20 | 22 | 20 | 21 | 22 |
| | F | 6.25 | 20 | 0 | 15* | 19 | 20 | 20 | 20 | 20 | 20 | 20 | 20 | 18 |
| | G | 3.125 | 19 | 0 | 12* | 22* | 22 | 22 | 22 | 20 | 20 | 22 | 18 | 16 |
| | H | 1.56 | 20 | 0 | 9* | 19* | 20 | 20 | 20 | 20 | 18 | 16 | 18 | 18 |

Cefotaxime (µM)

| 220 | 110 | 55 | 27.5 | 13.8 | 6.9 | 3.4 | 1.7 | 0.86 | 0.43 | 0.21 |

Cefotaxime (µg/ml)

| Inh2-B1 (µM) | | 1 | 2 | 3 | 4 | 5 | 6 | 7 | 8 | 9 | 10 | 11 | 12 |
|---|---|---|---|---|---|---|---|---|---|---|---|---|---|
| | | | 100 | 50 | 25 | 12.5 | 6.3 | 3.1 | 1.6 | 0.78 | 0.4 | 0.2 | 0.1 |
| | A | 21+4** | 0 | 11 | 16 | 21 | 22 | 18 | 25 | 22 | 21 | 21 | 20 |
| | B | 100 | 0 | 0 | 0 | 0 | 0 | 0 | 0 | 0 | 0 | 0 | 02 | 02 |
| | C | 50 | 9 | 0 | 0 | 0 | 0 | 01 | 07 | 07 | 06 | 5 | 5 | 12 |
| | D | 25 | 12 | 0 | 5* | 15 | 14 | 15 | 19 | 13 | 17 | 13 | 16 | 17 |
| | E | 12.5 | 20 | 0 | 14 | 14 | 15 | 20 | 20 | 20 | 20 | 18 | 20 | 21 |
| | F | 6.25 | 24 | 0 | 17 | 20 | 20 | 18 | 20 | 20 | 20 | 19 | 20 | 23 |
| | G | 3.125 | 18 | 0 | 17 | 20 | 20 | 20 | 20 | 18 | 17 | 13 | 21 | 20 |
| | H | 1.56 | 15 | 0 | 15* | 20 | 20 | 15 | 16 | 17 | 15 | 15 | 15 | 15 |

Figure 15B

```
                           SEQUENCE LISTING

<160> NUMBER OF SEQ ID NOS: 42

<210> SEQ ID NO 1
<211> LENGTH: 36
<212> TYPE: DNA
<213> ORGANISM: Artificial Sequence
<220> FEATURE:
<223> OTHER INFORMATION: Synthetic construct

<400> SEQUENCE: 1
ctacggccat atgataggta aaataataaa tgaacg                                36

<210> SEQ ID NO 2
<211> LENGTH: 28
<212> TYPE: DNA
<213> ORGANISM: Artificial Sequence
<220> FEATURE:
<223> OTHER INFORMATION: Synthetic construct

<400> SEQUENCE: 2
cgcgggatcc ttagacatct tcattcgc                                        28

<210> SEQ ID NO 3
<211> LENGTH: 44
<212> TYPE: DNA
<213> ORGANISM: Artificial Sequence
<220> FEATURE:
<223> OTHER INFORMATION: Synthetic construct

<400> SEQUENCE: 3
ctacggccat atgctagagg cacaattttt tactgatact ggac                      44

<210> SEQ ID NO 4
<211> LENGTH: 36
<212> TYPE: DNA
<213> ORGANISM: Artificial Sequence
<220> FEATURE:
<223> OTHER INFORMATION: Synthetic construct

<400> SEQUENCE: 4
ccgcggatcc tcatacttta tcaccttcaa tagccg                               36

<210> SEQ ID NO 5
<211> LENGTH: 30
<212> TYPE: DNA
<213> ORGANISM: Artificial Sequence
<220> FEATURE:
<223> OTHER INFORMATION: Synthetic construct

<400> SEQUENCE: 5
aaactcgaga tgcaaatggc tagaaaagtt                                      30

<210> SEQ ID NO 6
<211> LENGTH: 30
<212> TYPE: DNA
<213> ORGANISM: Artificial Sequence
<220> FEATURE:
<223> OTHER INFORMATION: Synthetic construct

<400> SEQUENCE: 6
tttggatccc tactcatgtt gttggaggaa                                      30

<210> SEQ ID NO 7
```

```
<211> LENGTH: 18
<212> TYPE: DNA
<213> ORGANISM: Artificial Sequence
<220> FEATURE:
<223> OTHER INFORMATION: Synthetic construct

<400> SEQUENCE: 7
tggaagtatg tcgtgaag                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic construct

<400> SEQUENCE: 8
gtgctggttg tgagtaat                                                 18

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
taggtccaga cgcgagctat                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
cgtctttcgc atgaccacta                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
tcggtattgc tggtgtcaaa                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
caacacgcca aacaacaatc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
```
cgaactcagg atctgcaaca                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
cgctgcgtta tcccagttat                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ccacctgatc caccattagg                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gctggttcag catcatctca                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
cacaacaaca tggcacacaa                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
tgaaatcacg tcaccaggaa                                            20

<210> SEQ ID NO 19
<211> LENGTH: 21
<212> TYPE: DNA
<213> ORGANISM: Artificial Sequence
<220> FEATURE:
<223> OTHER INFORMATION: Synthetic construct

<400> SEQUENCE: 19
aatggttgca ttaacgcttg t                                          21

<210> SEQ ID NO 20
<211> LENGTH: 20
<212> TYPE: DNA

```
<213> ORGANISM: Artificial Sequence
<220> FEATURE:
<223> OTHER INFORMATION: Synthetic construct

<400> SEQUENCE: 20
ttgctgtttt tggttggaca                                                 20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
tgggtatgtc gaacaaagca                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
tttccgtttg aaattgctga                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
aggaaatgca ggtcacgaag                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
ttagttgcag gtgcttgtgc                                                 20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
aatggccgtt caatctcaag                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
acgtatgcaa cgtgaccgta                                                 20
```

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
aggtcaagca catcatgcag                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
accgatttct ccgcctactt                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
taaccacacc agcaccatgt                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
tgttggtggg aaaattggtt                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
ctgcaggtgc tactggttca                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct

<400> SEQUENCE: 32
acagctgcgt tgatttgttg                                                    20

<210> SEQ ID NO 33
<211> LENGTH: 21
<212> TYPE: DNA
<213> ORGANISM: Artificial Sequence
<220> FEATURE:

<223> OTHER INFORMATION: Synthetic construct

<400> SEQUENCE: 33
gttatccgga attattgggc g                                             21

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34
ccgggctttc acatcagact                                               20

<210> SEQ ID NO 35
<211> LENGTH: 25
<212> TYPE: DNA
<213> ORGANISM: Artificial Sequence
<220> FEATURE:
<223> OTHER INFORMATION: Synthetic construct

<400> SEQUENCE: 35
agtacaattc ggtagataga gttag                                         25

<210> SEQ ID NO 36
<211> LENGTH: 25
<212> TYPE: DNA
<213> ORGANISM: Artificial Sequence
<220> FEATURE:
<223> OTHER INFORMATION: Synthetic construct

<400> SEQUENCE: 36
cttgctgtca ttcctttgct gttag                                         25

<210> SEQ ID NO 37
<211> LENGTH: 27
<212> TYPE: DNA
<213> ORGANISM: Artificial Sequence
<220> FEATURE:
<223> OTHER INFORMATION: Synthetic construct

<400> SEQUENCE: 37
agttgtatct attttagaaa catttgt                                       27

<210> SEQ ID NO 38
<211> LENGTH: 22
<212> TYPE: DNA
<213> ORGANISM: Artificial Sequence
<220> FEATURE:
<223> OTHER INFORMATION: Synthetic construct

<400> SEQUENCE: 38
ttctatttat tactcctaac at                                            22

<210> SEQ ID NO 39
<211> LENGTH: 24
<212> TYPE: DNA
<213> ORGANISM: Artificial Sequence
<220> FEATURE:
<223> OTHER INFORMATION: Synthetic construct

<400> SEQUENCE: 39
tcctattaat tatctgttaa tctc                                          24

```
<210> SEQ ID NO 40
<211> LENGTH: 24
<212> TYPE: DNA
<213> ORGANISM: Artificial Sequence
<220> FEATURE:
<223> OTHER INFORMATION: Synthetic construct

<400> SEQUENCE: 40
gaataaagtc ctccaaagtt ctat                                          24

<210> SEQ ID NO 41
<211> LENGTH: 25
<212> TYPE: DNA
<213> ORGANISM: Artificial Sequence
<220> FEATURE:
<223> OTHER INFORMATION: Synthetic construct

<400> SEQUENCE: 41
atcctcccaa taatcaaaac actct                                         25

<210> SEQ ID NO 42
<211> LENGTH: 26
<212> TYPE: DNA
<213> ORGANISM: Artificial Sequence
<220> FEATURE:
<223> OTHER INFORMATION: Synthetic construct

<400> SEQUENCE: 42
cttgatgcac taaacttttg aaatat                                        26
```

METHODS AND COMPOSITIONS RELATED TO STK1-TARGETED SMALL MOLECULES AS ANTIBIOTIC RESISTANCE BREAKERS

CROSS REFERENCE TO RELATED APPLICATIONS

This application is a national stage application filed under 35 U.S.C. § 371 of PCT/US2018/040602 filed Jul. 2, 2018, which claims the benefit of priority to U.S. Provisional Application No. 62/527,589, filed Jun. 30, 2017, and U.S. Provisional Application No. 62/528,266, filed Jul. 3, 2017, each of which is incorporated by reference herein in its entirety.

STATEMENT REGARDING FEDERALLY FUNDED RESEARCH

This invention was made with government support under grant number AI057153 awarded by the National Institutes of Health. The government has certain rights in the invention.

BACKGROUND

Highly pathogenic and multidrug-resistant *S. aureus* (MDRSA), including methicillin, vancomycin-, daptomycin- and linezolid-resistant *S. aureus* are continuously replacing the traditional methicillin-resistant *S. aureus* (MRSA) in the community as well as in the hospital. With a lag in the development of new, broad-spectrum antibiotics from pharmaceutical companies, the emergence of multi-drug-resistant traits in highly pathogenic community-associated *S. aureus* strains demands identification of novel chemotherapeutic agents for the effective control of MRSA/MDRSA dissemination.

Two-component regulatory systems (TCSs) constituted by sensor histidine kinases (HK), and response regulators (RR) allow bacteria to respond rapidly to environmental changes by modulating the transcription of genes in a coordinated manner. *S. aureus* encodes several TCSs that control a variety of metabolic functions, cell division/cell wall biosynthesis, virulence, and multiple drug resistance through His and Asp residue phosphorylation mechanisms. Eukaryote-type Ser/Thr protein kinases (STKs) and phosphatases (STPs) are conserved in several Gram-positive bacteria. They provide an additional level of regulation for a variety of biological functions, including, metabolic regulation and fitness, cell wall biosynthesis, cell division, resistance to an antimicrobial peptide, expression of virulence factors, virulence regulation, biofilm formation, antibiotic efflux functions, and drug resistance. This regulation occurs via post-translational modifications mediated by the reversible phosphorylation of certain Ser/Thr residues of the targeted proteins. In *S. aureus*, STK1 and STP1 modulate the activity of several TCSs and stand-alone or mono-component regulators. They have also been incriminated in the reciprocal modulation of susceptibility to cell wall acting antibiotics such as certain cephalosporins and vancomycin. *S. aureus* STK1-dependent vancomycin resistance has been attributed to the Thr-phosphorylation of VraR (T106, T119, T175, T178) and GraR (T128, T130) TCS regulators. Quinolone resistance has been attributed to STK1-dependent phosphorylation of the stand-alone regulator MgrA at Ser110 and Ser113. Phosphorylation affects the DNA binding activity of MgrA resulting in derepression of norA transcription, a gene that encodes the efflux pump responsible for quinolone efflux. STK1 and STP1 have also been proposed to modify Thr residues of SarA and CcpA as well as Cys residues of MgrA, SarA, SarZ, and CymR regulators. Thus, eukaryote-type STK and STP enzymes contribute broadly to the expression of genes involved in virulence and antibiotic resistance. The deletion or acquisition of naturally occurring point mutations in the stp1 gene under selective pressure results in decreased susceptibility to many important antibiotics. Paradoxically, naturally occurring mutations in the stk1 gene have not been observed so far. STK1 as well as STP1 are not essential for *S. aureus*. Cumulative findings show that STK1 may serve as a better target than STP1 for the development of therapeutics against multi-drug-resistant *S. aureus*. Thus, the inhibition of STK1 activity by an inhibitor may help reduce the *S. aureus* resistance against cell wall acting antibiotics. What is needed in the art is an inhibitor of STK1 activity.

SUMMARY

Provided herein are small molecule STK1 inhibitors. The STK1 inhibitors can be defined by Formula I

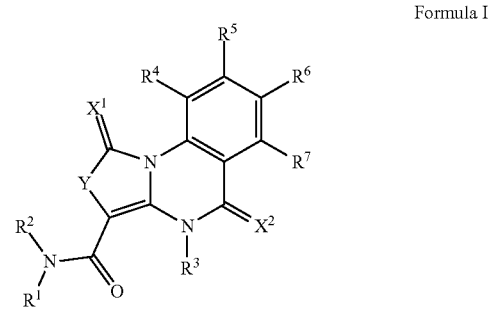

Formula I wherein
Y is selected from the group consisting of S and O;
$X^1$ is selected from the group consisting of S and O;
$X^2$ is selected from the group consisting of S and O: $R^1$ is —$(CHR^4)_n$-A and $R^2$ is selected from the group consisting of H and $C_{1-4}$ alkyl, or $R^1$ and $R^2$, together with the N atom to which they are attached, form a 4-6 membered heterocycloalkyl group or a 5-6 membered heteroaryl group, each optionally substituted with 1, 2, or 3 independently selected $R^B$ groups;
$R^3$ is selected from the group consisting of H and $C_{1-4}$ alkyl;
$R^4$, $R^5$, $R^6$, and $R^7$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;
each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

$R^A$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^B$ groups;

n is 0, 1, 2, or 3;

A is selected from the group consisting of $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, 4, or 5 independently selected $R^B$ groups; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some embodiments, $R^1$ is —$(CHR^A)_n$-A and $R^2$ is selected from the group consisting of H and $C_{1-4}$ alkyl. In some of these embodiments, A is defined by the structure below

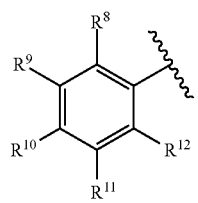

wherein $R^8$, $R^9$, $R^{10}$, $R^{11}$, and $R^{12}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^c$-$R^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{1-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In certain embodiments, the STK1 inhibitor is defined by Formula IA

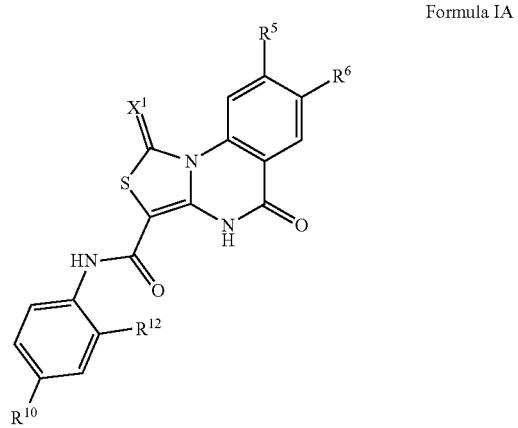

Formula IA wherein $X^1$ is selected from the group consisting of S and O;

$R^5$, $R^6$, $R^{10}$, and $R^{12}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some embodiments, $R^{12}$ can be selected from $C_{1-6}$ alkyl, $C_{1-4}$ haloalkyl, $C_{1-6}$ alkoxy, or $C_{1-6}$haloalkoxy. In some embodiments, $R^{12}$ can be halo.

In some embodiments, $R^{10}$ can be selected from $C_{1-6}$ alkyl, $C_{1-4}$ haloalkyl, $C_{1-6}$ alkoxy, $C_{1-6}$ haloalkoxy, and halo.

In some embodiments, $R^5$ is $C(O)OR^a$, $R^6$ is H, and $R^a$ is selected from $C_{1-6}$ alkyl and $C_{1-4}$ haloalkyl.

In some embodiments, $R^5$ is H, $R^6$ is $C(O)OR^a$, and $R^a$ is selected from $C_{1-6}$ alkyl and $C_{1-4}$ haloalkyl.

In some embodiments, $R^1$ can be —$(CHR^A)_n$-A, $R^2$ can be selected from the group consisting of H and $C_{1-4}$ alkyl; A can be cyclohexyl group optionally substituted by 1, 2, 3, 4, or 5 independently selected $R^B$ groups, and each $R^B$ can be independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the STK1 inhibitor can be defined by Formula IB

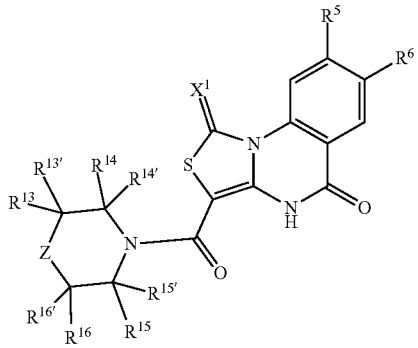

Formula IB wherein $X^1$ is selected from the group consisting of S and O;

Z is selected from the group consisting of $CR^{17}R^{17'}$, O, S, and $NR^{18}$;

$R^5$, $R^6$, $R^{13}$, $R^{13'}$, $R^{14}$, $R^{14'}$, $R^{15}$, $R^{15'}$, $R^{16}$, and $R^{16'}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

$R^{17}$ and $R^{17'}$, when present, are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

$R^{18}$, when present, is selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^a$, $R^b$, $R^c$, and $R^d$ is independently selected from H, $C_{1-4}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-4}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di(Cis alkyl)carbamyl, aminosulfonyl, $C_{1-6}$ alkylaminosulfonyl, and di($C_{1-6}$ alkyl aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is $C(O)OR^a$, $R^6$ is H, and $R^a$ is selected from $C_{1-6}$ alkyl and $C_{1-4}$ haloalkyl. In other embodiments, $R^5$ is H, $R^6$ is $C(O)OR^a$, and $R^a$ is selected from $C_{1-6}$ alkyl and $C_{1-4}$ haloalkyl.

In some embodiments, the STK1 inhibitor can be defined by Formula IC

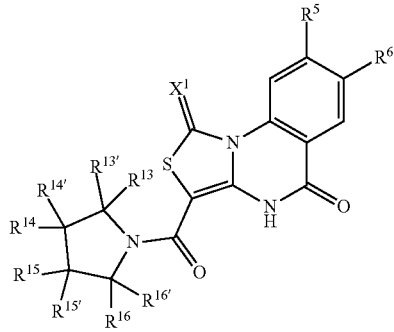

Formula IC wherein $X^1$ is selected from the group consisting of S and O;

Z is selected from the group consisting of $CR^{17}R^{17'}$, O, S, and $NR^{18}$;

$R^5$, $R^6$, $R^{13}$, $R^{13'}$, $R^{14}$, $R^{14'}$, $R^{15}$, $R^{15'}$, $R^{16}$, and $R^{16'}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is $C(O)OR^a$, $R^6$ is H, and $R^a$ is selected from $C_{1-6}$ alkyl and $C_{1-4}$ haloalkyl. In other embodiments, $R^5$ is H, $R^6$ is $C(O)OR^a$, and $R^a$ is selected from $C_{1-6}$ alkyl and $C_{1-4}$ haloalkyl.

In some embodiments, the STK1 inhibitor can be defined by Formula ID

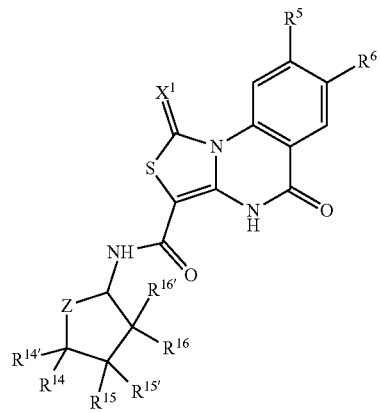

Formula ID wherein $X^1$ is selected from the group consisting of S and O:

Z is selected from the group consisting of $CR^{17}R^{17'}$, O, S, and $NR^{18}$;

$R^5$, $R^6$, $R^{14}$, $R^{14'}$, $R^{15}$, $R^{15'}$, $R^{16}$, and $R^{16'}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

$R^{17}$ and $R^{17'}$, when present, are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

$R^{18}$, when present, is selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is C(O)$OR^a$, $R^6$ is H, and $R^a$ is selected from $C_{1-6}$ alkyl and $C_{1-6}$ haloalkyl. In other embodiments, $R^5$ is H, $R^6$ is C(O)$OR^a$, and $R^1$ is selected from $C_{1-6}$ alkyl and $C_{1-4}$ haloalkyl.

In certain embodiments, the STK1 inhibitor is Inh2-B1 (methyl 5-oxo-3-(phenyl carbamoyl)-1-thioxo-4,5dihydro[1,3]thiazolo[3,4-a]quinazoline-8-carboxylate) or a salt, ester, or N-oxide thereof.

STK1 inhibitors, including the compounds described herein, can reduce the resistance of bacteria (e.g., *S. aureus*) against cell wall-acting antibiotics. Accordingly, the STK1 inhibitors described herein can be used to treat a bacterial infection in a subject. These methods can comprise administering to the subject a therapeutically effective amount of an antibiotic compound that acts on the cell wall of a bacteria (e.g., a cephalosporin) and an STK1 inhibitor described herein.

In some embodiments, the antibiotic can comprise a third generation cephalosporin (e.g., ceftriaxone or cefotaxime). In some embodiments, the bacterial infection can comprise a gram positive bacteria (e.g., *Staphylococcus aureus*). In certain embodiments, the bacterial infection can comprise a drug-resistant bacterial strain (e.g., a drug-resistant strain of *Staphylococcus aureus*, such as methicillin-resistant *Staphylococcus aureus*).

In some cases, the antibiotic (e.g., the cephalosporin) and the STK1 inhibitor can be administered to the subject within 48 hours or less of each other (e.g., within 24 hours or less of each other, within 12 hours or less of each other, within 8 hours or less of each other, within 4 hours or less of each other, within 2 hours or less of each other, or within 1 hour or less of each other. In certain cases, the antibiotic (e.g., the cephalosporin) and the STK1 inhibitor can be administered to the subject simultaneously (e.g., in the same dosage form, or in two separate dosage forms administered to the subject concurrently).

Also provided are methods of inhibiting Ser/Thr protein kinase (STK1) in a bacterial cell. These methods can comprise contacting the bacterial cell with an STK1 inhibitor described herein (e.g., Inh2-B1 (methyl 5-oxo-3-(phenyl carbamoyl)-1-thioxo-4,5dihydro[1,3]thiazolo[3,4-a]quinazoline-8-carboxylate). These methods can further involve contacting the bacterial cell with an antibiotic compound that acts on the cell wall of a bacteria (e.g., a cephalosporin). In some embodiments, the antibiotic can comprise a third generation cephalosporin (e.g., ceftriaxone or cefotaxime). In some embodiments, the bacteria can comprise a gram positive bacteria (e.g., *Staphylococcus aureus*). In certain embodiments, the bacteria can comprise a drug-resistant bacterial strain (e.g., a drug-resistant strain of *Staphylococcus aureus*, such as methicillin-resistant *Staphylococcus aureus*).

Also provided are pharmaceutical compositions that comprise a therapeutically effective amount of a Ser/Thr protein kinase (STK1) inhibitor to treat or prevent a bacterial infection in a subject dissolved or dispersed in a pharmaceutically acceptable carrier. In some embodiments, the composition can further comprise an antibiotic compound (e.g., an antibiotic that acts on the cell wall of a bacteria, such as a cephalosporin). In some embodiments, the antibiotic can comprise a third generation cephalosporin (e.g., ceftriaxone or cefotaxime).

Additional advantages will be set forth in part in the description that follows or may be learned by practice of the aspects described below. The advantages described below will be realized and attained by the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 10A shows the E-test strip-based MIC determination for cefotaxime (TX) and cefotaxime (CT) using MH-II agar plates. FIG. 10B shows the susceptibility of *S. aureus* MW2-WT to Inh2 as determined by the broth dilution method using Muller Hinton-II broth containing different concentrations of Inh2.

FIGS. 15A-15B show checkerboard assays for determining bactericidal assay. Serial two-fold dilutions of 2 mM of Inh2-B1 (MW=411.58 g/mol) and (A) 3 mM ceftriaxone (MW=669.7 g/mol) were made in two separate 96-well plates in vertical (B1-B12 to H1-H2 wells) and horizontal (A2-H2 to A12-H12 wells) directions respectively. Serially diluted Inh2-B1 (100 μL) in the individual well was then mixed with the 100 μL serially diluted ceftriaxone present in the corresponding wells. The resulting various combinations of Inh2-B1 (starting from 1 mM) and ceftriaxone (starting from 1.5 mM) or cefotaxime (2.1 mM) as well as serially diluted one Inh2-B1 (B1 to H1) and ceftriaxone (A2-A12) or cefotaxime (A2-A12) were then incorporated in Muller-Hinton mini agar plates (2 mL). The agar plates were then seeded and diluted *S. aureus* MW2-wild-type culture equivalent to approximately 23±3 CFU. This checkerboard assay was used to determine the ideal combination of lowest concentration of Inh2-B1 and ceftriaxone that kills 99.9% of the wild-type MW2. (B) a similar procedure as described above was employed to determine the impact on the bactericidal activity of cefotaxime in the presence or absence of Inh2-B1. ** CFU colony forming units of *S. aureus* MW2-A1 well shows CFUs without Inh2-B1 and ceftriaxone. A2-A12 CFUs only in the presence of ceftriaxone/cefotaxime. B1-H1 CFUs only in the presence of Inh2-B1. * Minute colonies appeared after 48 h incubation.

Figure 1:
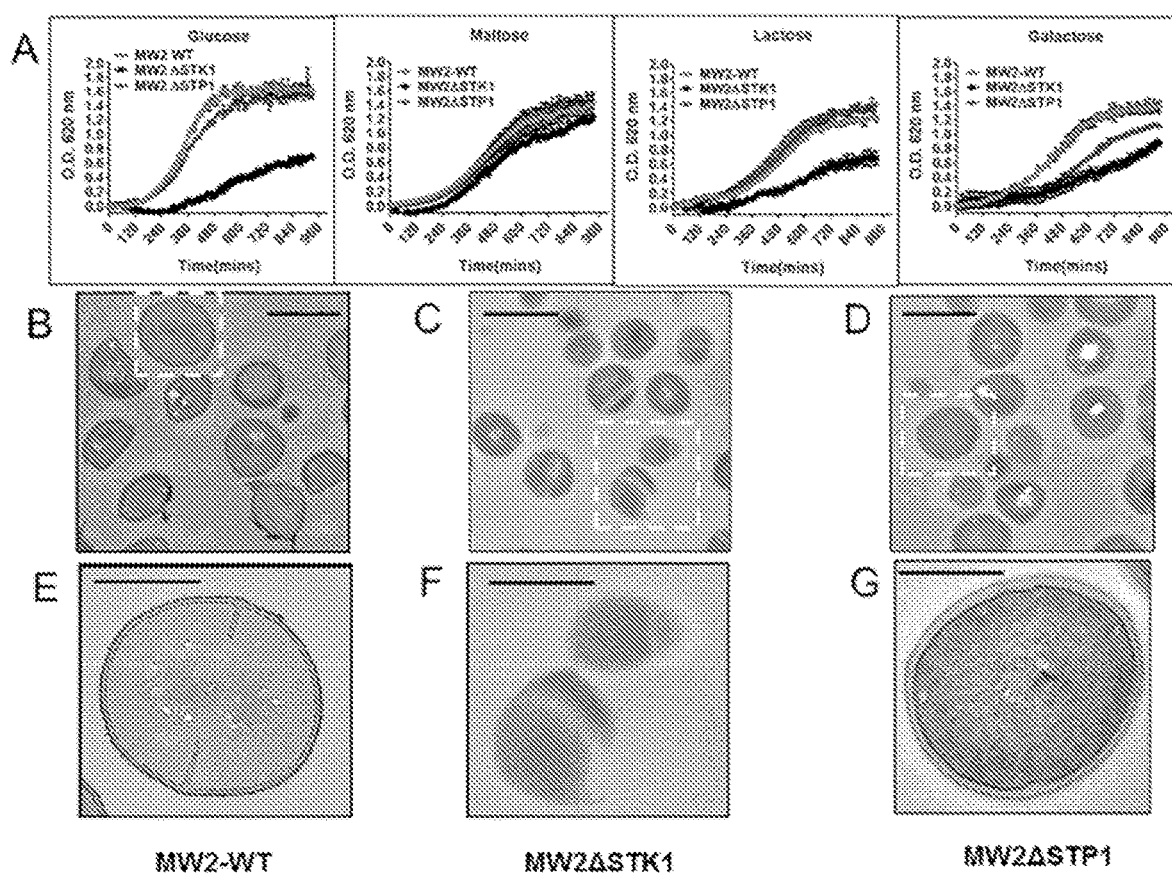
FIGS. 1A-G show the impact of the deletion of stk1 and stp1 genes in *S. aureus* MW2 growth and cell wall structure. (A) Growth patterns of the *S. aureus* MW2-wild-type, MW2ΔSTK1, and MW2ΔSTP1 strains in Chemically defined medium (CDM) supplemented with 1% carbohydrate (glucose, maltose, lactose, or galactose). Growth kinetics were measured in 96-well plates at 37° C. for 16 hours under constant rotation in a final volume of 200 μl using sterile 96-well plates. Optical density at 620 nm was measured at every 15 min. Data at each time point represent an O.D. value (mean±SD) obtained from three different experiments and each with quadruple wells for each strain. OD was measured spectrophotometrically as described in the Materials and Methods. Growth curves are shown in Red—MW2-wild-type strain; Black—MW2ΔSTK1 mutant; Blue—MW2ΔSTP1 mutant strains. (B-D) Transmission electron microscopy (TEM) at a low resolution of (B) wild-type MW2 and corresponding isogenic (C) ΔSTK1 and (D) ΔSTP1 mutants. The wild-type and mutant strains were grown in TSB, fixed in the glutaraldehyde and paraformaldehyde fixative and subsequently subjected to transmission electron microscopy as described in Materials and Methods. Inset bar-1.0 μm. (E-G) TEM of (B-D) at a higher resolution. Inset bar-500 nm.

(SM-STK). *S. pneumoniae* (Pneu-SATK). *Enterococcus faecalis* (LL-STK1), and *M. tuberculosis* (MTB-STK).

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

Unless otherwise defined, all technical and scientific terms used herein have the same meaning as commonly understood by one of ordinary skill in the art to which this invention belongs. Methods and materials are described herein for use in the present invention, other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

By "reduce" or other forms of the word, such as "reducing" or "reduction," is meant lowering of an event or characteristic (e.g., bacterial infection). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event. The term "control" is used synonymously with the term "treat."

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "C-m alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "C-m alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkylaminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge.

Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example. Jacques, et al., Enantiomers, Racemates and Resolutions (Wiley Interscience, New York, 1981); Wilen, S. H., et al., Tetrahedron 33:2725 (1977); Eliel. E. L. Stereochemistry of Carbon Compounds (McGraw-Hill, NY. 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature. e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company. Easton, Pa., 1985, p. 1418 and *Journal of Pharmaceutical Science*, 66, 2 (1977). Conventional methods for preparing salt forms are described, for example, in Handbook of Pharmaceutical Salts: Properties, *Selection, and Use*. Wiley-VCH, 2002.

Reference will now be made in detail to specific aspects of the disclosed materials, compounds, compositions, articles, and methods, examples of which are illustrated in the accompanying Examples and Figures.

STK1 Inhibitors

Ser/Thr protein kinase (STK1) plays a critical role in cell wall biosynthesis of and drug resistance in methicillin-resistant *Staphylococcus aureus* (MRSA). MRSA strains lacking STK1 become susceptible to failing cephalosporins, such as Ceftriaxone and Cefotaxime. STK1, despite being nonessential protein for MRSA survival, can serve as an important therapeutic agent for combination therapy.

Disclosed herein are small molecule inhibitors of STK1. The compounds can specifically inhibit STK1 activity by directly binding to its ATP-binding catalytic domain. The STK1 inhibitors can be defined by Formula I

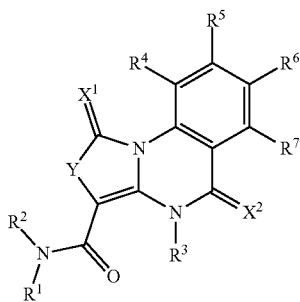

Formula I wherein
Y is selected from the group consisting of S and O;
X¹ is selected from the group consisting of S and O;
X² is selected from the group consisting of S and O;
R¹ is —(CHR$^A$)$_n$-A and R² is selected from the group consisting of H and C$_{1-4}$ alkyl, or R¹ and R², together with the N atom to which they are attached, form a 4-6 membered heterocycloalkyl group or a 5-6 membered heteroaryl group, each optionally substituted with 1, 2, or 3 independently selected R$^B$ groups;
R³ is selected from the group consisting of H and C$_{1-4}$ alkyl;
R⁴, R⁵, R⁶, and R⁷ are each independently selected from the group consisting of H, halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^B$ groups;
each R$^a$, R$^b$, R$^c$, and R$^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$cycloalkyl, 6-10 membered aryl, 5-10 membered heteroaryl, and 4-10 membered heterocycloalkyl are each optionally substituted with 1, 2, 3, or 4 independently selected R$^B$ groups;
each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl;
R$^A$ is selected from the group consisting of H, C$_{1-6}$ alkyl, C$_{1-6}$ alkoxy, and amino, wherein said C$_{1-6}$ alkyl is optionally substituted by 1, 2, 3, or 4 independently selected R$^B$ groups;
n is 0, 1, 2, or 3;
A is selected from the group consisting of C$_{3-10}$ cycloalkyl, C$_{6-10}$ aryl, 4-10 membered heterocycloalkyl, and 5-10 membered heteroaryl, wherein the C$_{3-10}$ cycloalkyl, C$_{6-10}$ aryl, 4-10 membered heterocycloalkyl, and 5-10 membered heteroaryl are each optionally substituted by 1, 2, 3, 4, or 5 independently selected R$^B$ groups; and
each R$^B$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkylaminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or a pharmaceutically acceptable salt, ester, or N-oxide thereof.

In some embodiments, R¹ is —(CHR$^A$)$_n$-A and R² is selected from the group consisting of H and C$_{1-4}$ alkyl. In some of these embodiments, A is defined by the structure below

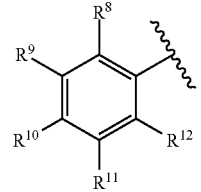

wherein
R⁸, R⁹, R¹⁰, R¹¹, and R¹² are each independently selected from the group consisting of H, halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR)NR$^c$R$^d$, NR$^c$C(=NR$^e$)NR$^c$-R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^B$ groups;
each R$^a$, R$^b$, R$^c$, and R$^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl are each optionally substituted with 1, 2, 3, or 4 independently selected R$^B$ groups;
each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl; and
each R$^B$ is independently selected from OH, NO, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$, alkyl, HO—C$_{1-3}$ alkyl, amino, C$_{1-6}$ alkylamino, di(C$_{1-6}$ alkyl)amino, thio, C$_{1-6}$alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino. C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In certain embodiments, the STK1 inhibitor is defined by Formula IA

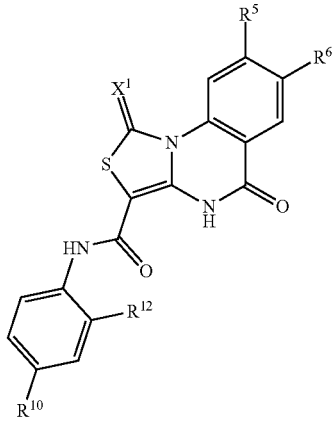

Formula IA wherein

X$^1$ is selected from the group consisting of S and O;

R$^5$, R$^6$, R$^{10}$, and R$^{12}$ are each independently selected from the group consisting of H, halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^B$ groups;

each R$^a$, R$^b$, R$^c$, and R$^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl are each optionally substituted with 1, 2, 3, or 4 independently selected R$^B$ groups;

each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl; and each R$^B$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or a pharmaceutically acceptable salt, ester, or N-oxide thereof.

In some embodiments, R$^{12}$ can be selected from C$_{1-6}$ alkyl, C$_{1-4}$ haloalkyl, C$_{1-6}$ alkoxy, or C$_{1-6}$ haloalkoxy. In some embodiments, R$^{12}$ can be halo.

In some embodiments, R$^{10}$ can be selected from C$_{1-6}$ alkyl, C$_{1-6}$ haloalkyl, C$_{1-6}$ alkoxy, C$_{1-6}$ haloalkoxy, and halo.

In some embodiments, R$^5$ is C(O)OR$^a$, R$^6$ is H, and R$^a$ is selected from C$_{1-6}$ alkyl and C$_{1-4}$ haloalkyl.

In some embodiments, R$^5$ is H, R$^6$ is C(O)OR$^a$, and R$^c$ is selected from C$_{1-6}$ alkyl and C$_{1-4}$ haloalkyl.

In some embodiments, R$^1$ can be —(CHR$^A$)$_n$-A, R$^2$ can selected from the group consisting of H and C$_{1-4}$ alkyl; A can be cyclohexyl group optionally substituted by 1, 2, 3, 4, or 5 independently selected R$^B$ groups; and each R$^B$ can be independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the STK1 inhibitor can be defined by Formula IB

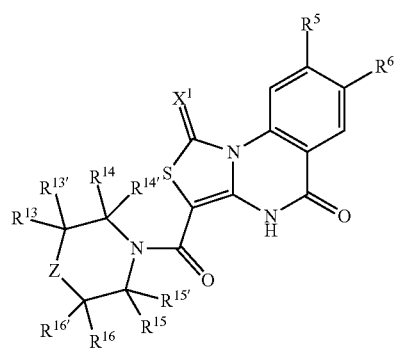

Formula IB wherein

X is selected from the group consisting of S and O;

Z is selected from the group consisting of CR$^{17}$R$^{17'}$, O, S, and NR$^{18}$;

R$^5$, R$^6$, R$^{13}$, R$^{13'}$, R$^{14}$, R$^{14'}$, R$^{15}$, R$^{15'}$, R$^{16}$, and R$^{16'}$ are each independently selected from the group consisting of H, halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{1-6}$ alkenyl, C$_{2-6}$ alkynyl, and C$_{1-4}$ haloalkyl are optionally substituted with 1, 2, 3, or 4 independently selected R$^B$ groups;

R$^{17}$ and R$^{17'}$, when present, are each independently selected from the group consisting of H, halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^d$, C(=NR$^e$)NR$^c$R$^d$, NR$^c$C(=NR$^e$) NR$^c$R$^d$, NR$^c$S(O)R$^b$, NR$^c$S(O)$_2$R$^b$, NR$^c$S(O)$_2$NR$^c$R$^d$, S(O) R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^B$ groups;

R[18], when present, is selected from H, $C_{1-6}$ alkyl, $C_{2-6}$ alkenyl, $C_{2-6}$ alkynyl, $C_{1-4}$ haloalkyl, $C_{3-10}$cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-6}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, CIA alkylaminosulfonyl, di($C_{1-6}$ alkylaminosulfonyl, aminosulfonylamino, $C_{1-6}$alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is $C(O)OR^a$, $R^6$ is H, and $R^1$ is selected from $C_{1-6}$ alkyl and $C_{1-4}$ haloalkyl. In other embodiments, $R^5$ is H, $R^6$ is $C(O)OR^a$, and $R^a$ is selected from $C_{1-6}$ alkyl and $C_{1-4}$ haloalkyl.

In some embodiments, the STK1 inhibitor can be defined by Formula IC $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_2$, alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the Ca-6 alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$, haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-4}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is $C(O)OR^a$, $R^6$ is H, and $R^a$ is selected from $C_{1-6}$ alkyl and $C_{1-4}$ haloalkyl. In other embodiments, $R^5$ is H, $R^6$ is $C(O)OR^a$, and $R^a$ is selected from $C_{1-6}$ alkyl and $C_{1-4}$ haloalkyl.

In some embodiments, the STK1 inhibitor can be defined by Formula ID

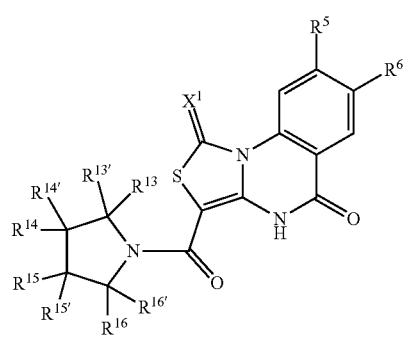

Formula IC

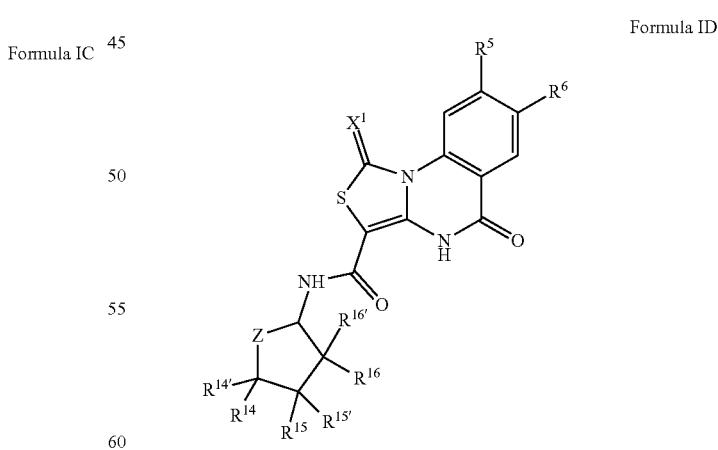

Formula ID wherein $X^1$ is selected from the group consisting of S and O;

Z is selected from the group consisting of $CR^{17}R^{17'}$, O, S, and $NR^{18}$;

$R^5$, $R^6$, $R^{13}$, $R^{13'}$, $R^{14}$, $R^{14'}$, $R^{15}$, $R^{15'}$, $R^{16}$, and $R^{16'}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, wherein $X^1$ is selected from the group consisting of S and O;

Z is selected from the group consisting of $CR^{17}R^{17'}$, O, S, and $NR^{18}$;

$R^5$, $R^6$, $R^{14}$, $R^{14'}$, $R^{15}$, $R^{15'}$, $R^{16}$, and $R^{16'}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

$R^{17}$ and $R^{17'}$, when present, are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{1-6}$ alkenyl, $C_{2-6}$ alkynyl, and $C_{1-4}$ haloalkyl are optionally substituted with 1, 2, 3, or 4 independently selected $R^B$ groups;

$R^{18}$, when present, is selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$haloalkoxy, cyano-$C_{1-3}$ alkyl, HO—$C^{1-6}$ alkyl, amino, $C_{1-6}$ alkylamino, di($C_{1-6}$ alkyl)amino, thio, $C_{1-6}$, alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

In some of these embodiments, $R^5$ is $C(O)OR^a$, $R^6$ is H, and $R^a$ is selected from $C_{1-6}$ alkyl and $C_{1-4}$ haloalkyl. In other embodiments, $R^5$ is H, $R^6$ is $C(O)OR^a$, and $R^a$ is selected from $C_{1-6}$ alkyl and $C_{1-4}$ haloalkyl.

In certain embodiments, the STK1 inhibitor is Inh2-B1 (methyl 5-oxo-3-(phenyl carbamoyl)-1-thioxo-4,5dihydro[1,3]thiazolo[3,4-a]quinazoline-8-carboxylate) or a salt, ester, or N-oxide thereof.

Functional analyses encompassing in vitro growth inhibition of MRSA, and in vivo protection studies in mice against the lethal MRSA challenge indicated that at high concentration neither Inh2-B1 nor Ceftriaxone or Cefotaxime alone was able to inhibit the growth of bacteria or protect the challenged mice. However, the growth of MRSA was inhibited, and a significant protection in mice against the bacterial challenge was observed at a micromolar concentration of Ceftriaxone or Cefotaxime in the presence of Inh2-B1. Cell-dependent minimal to no toxicity of Inh2-B1, and its abilities to down-regulate cell wall hydrolase genes and disrupt the biofilm formation of MRSA clearly indicated that Inh2-B1 serves as a therapeutically important "antibiotic-resistance-breaker," which enhances bactericidal activity of Ceftriaxone/Cefotaxime against highly pathogenic MRSA infection.

Herein, it is shown that STK1 serves as a novel target for the development of a small molecule-based therapeutic agent by acting as an "antibiotic resistance breaker." Such an agent can potentiate the bactericidal activity of the cell wall acting antibiotics which once served as "life-saving drugs" are now deemed to be "off the shelf" or the failing antibiotics due to the emergence of multidrug-resistant bacteria. Disclosed herein is a proof for this hypothesis by identifying small molecule inhibitors (e.g., Inh2-B1) that specifically targets STK1, alters cell wall biosynthesis, and adversely affects biofilm formation of S. aureus. Further, using the mouse model of S. aureus septicemia, it was confirmed that the STK inhibitors described herein (e.g., Inh2-B1) potentiate the bactericidal activity of cell-wall acting cephalosporins (e.g., Ceftriaxone and Cefotaxime) and provides significant protection against lethal MRSA infection.

Synthesis

The STK1 inhibitors described herein can be prepared using synthetic methodologies known in the art. By way of example, representative STK1 activators described herein can be prepared using the general synthetic strategy outlined in Scheme 1 below.

Scheme 1

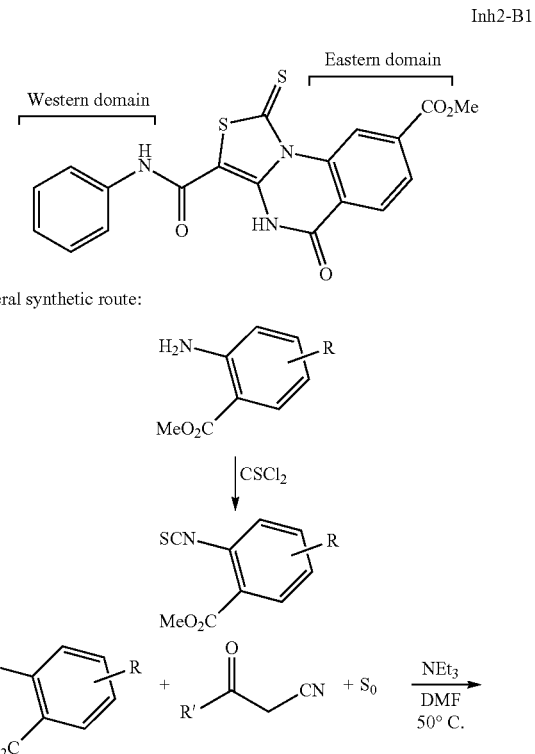

-continued

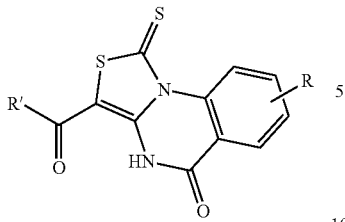

Eastern Domain Analogs

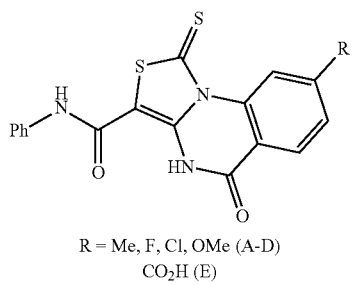

R = Me, F, Cl, OMe (A-D)
CO₂H (E)

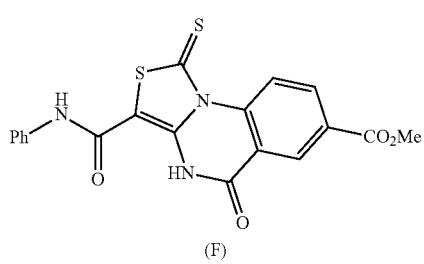

(F)

Western Domain Analogs

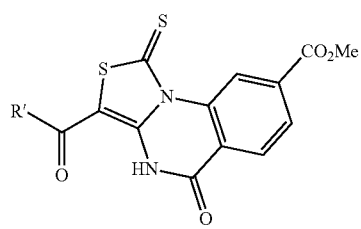

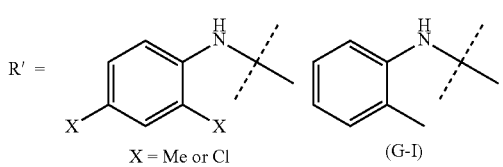

X = Me or Cl          (G-I)

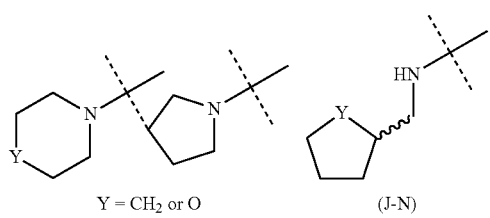

Y = CH₂ or O          (J-N)

-continued
Thiocarbonyl Replacement

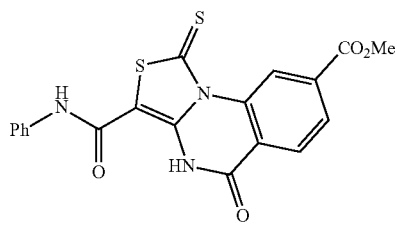

1. Me₂SO₄
2. Na₂SO₃ (aq)

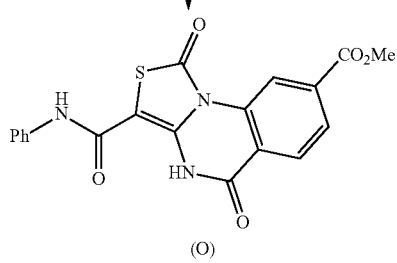

(O)

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations,* (Pergamon Press, 1996); Katritzky et al. (Ed.); *Comprehensive Organic Functional Group Transformations II* (Elsevier, 2$^{nd}$ Edition, 2004); Katritzky et al. (Ed.). *Comprehensive Heterocyclic Chemistry* (Pergamon Press, 1984); Katritzky et al., *Comprehensive Heterocyclic Chemistry II*, (Pergamon Press. 1996); Smith et al., *March's Advanced Organic Chemistry*: Reactions, Mechanisms, and Structure, 6$^{th}$ Ed. (Wiley, 2007); Trost et al. (Ed.), *Comprehensive Organic Synthesis* (Pergamon Press. 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M.

Wuts, *Protective Groups in Organic Synthesis*, 3rd Ed., Wiley & Sons. Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

STK1 inhibitors, including the compounds described herein, can reduce the resistance of bacteria (e.g., *S. aureus*) against antibiotics, such as cell wall-acting antibiotics. Accordingly, the STK1 inhibitors described herein can be used to treat a bacterial infection in a subject. These methods can comprise administering to the subject a therapeutically effective amount of an antibiotic compound (e.g., an antibiotic that acts on the cell wall of a bacteria, such as a cephalosporin) and an STK1 inhibitor described herein.

The methods include treatment of bacterial infections due to microorganisms, including Gram positive and Grain negative microorganisms such as *Staphylococcus aureus* (methicillin-susceptible and methicillin-resistant isolates), *Streptococcus pneumoniae* (including multidrug-resistant isolates [MDRSP]), *Streptococcus pyogenes, Streptococcus agalactiae, Streptococcus dysgalactiae, Streptococcus anginosus* group (including *S. anginosus, S. intermedius*, and *S. constellatus*), *Enterococcus faecalis* (ampicillin-susceptible), *Escherichia coli, Klebsiella pneumoniae, Klebsiella oxytoca, Morganella morganii, Haemophilus influenzae* (including beta-lactamase-producing strains) and *Haemophilus parainfluenzae* (including beta-lactamase-producing strains). The multidrug-resistant *Streptococcus pneumoniae* isolates are strains resistant to two or more of the following antibiotics: penicillin (minimum inhibitory concentration (MIC)>2 mcg/ml), second generation cephalosporins (e.g., cefuroxime), macrolides, chloramphenicol, fluoroquinolones, tetracyclines and trimethoprim/sulfamethoxazole.

In some embodiments, the methods include treating bacterial infections due to facultative Gran-positive microorganisms, e.g., Group CFG streptococci, *Viridans* group streptococci and *Streptococcus pneumoniae* (penicillin-intermediate, penicillin-resistant or multidrug-resistant); facultative Gram-negative microorganisms, e.g., *Citrobacter koseri* (ceftazidime-susceptible), *Citrobacter freundii* (ceftazidime-susceptible), *Enterobacter cloacace* (ceftazidime-susceptible), *Enterobacter aerogenes* (ceftazidime-susceptible), *Haemophilus influenzae* (beta-lactamase-negative, ampicillin-resistant), *Moraxrella catarrhalis, Neisseria gonorrhoeae, Neisseria meningitidis, Pasteurella multocida, Providencia rettgeri* (ceftazidime-susceptible), *Proteus mirabilis* (ceftazidime-susceptible), *Salmonella* spp. (ceftazidime-susceptible) and *Shigella* spp (ceftazidime-susceptible); and anaerobic microorganisms, e.g., *Clostridium* spp., *Finegoldia magna, Propionibacterium acnes, Fusobacterium nucleatum* and *Fusobacterium necrophorum*.

In some embodiments, the methods may include the treatment of complicated skin and skin structure infections (cSSSI). The cSSSI may be due to Gram-positive and Gram-negative microorganisms, such as *Staphylococcus, Streptococcus, Enterococcus, Escherichia, Klebsiella* and *Morganella*. In exemplary embodiments, the microorganism may be a *Staphylococcus aureus* including methicillin-susceptible and methicillin-resistant isolates. In other embodiments, the cSSSI may be due to *Streptococcus pyogenes, Streptococcus agalactiae, Streptococcus dysgalactiae* or *Streptococcus anginosus* group (including *S. anginosus, S. intermedius*, and *S. constellatus*). In still other embodiments, the cSSSI may be due to *Enterococcus faecalis*, e.g., an ampicillin-susceptible isolate of *Enterococcus faecalis*. In some embodiments, the cSSSI may be due to *Escherichia coli, Klebsiella pneumoniae, Klebsiella oxytoca* or *Morganella morganii*.

In some embodiments, the methods may include the treatment of community-acquired bacterial pneumonia (CABP). The CABP may be due to Gram-positive and Gram-negative microorganisms, such as *Streptococcus Staphylococcus, Haemophilus, Haemophilis, Klebsiella* and *Escherichia*. In exemplary embodiments, the infection may be due to susceptible isolates of *Streptococcus pneumoniae, Staphylococcus aureus, Haemophilus influenzae, Haemophilus parainfluenzae, Klebsiella pneumoniae* or *Escherichia coli*. In exemplary embodiments, the microorganism may be *Streptococcus pneumoniae*. The strain of *Streptococcus pneumoniae* may be penicillin-susceptible, penicillin-resistant or multidrug resistant. In further embodiments, the microorganism may be *Streptococcus pneumoniae* serotype 19A. In some embodiments, the CABP may be associated with concurrent bacteremia. In other exemplary embodiments, the microorganism may be *Staphylococcus aureus*. The strain or isolate of *Staphylococcus aureus* may be methicillin-susceptible or methicillin-resistant. In still other exemplary embodiments, the microorganism may be *Haemophilus influenzae. Klebsiella pneumoniae* or *Escherichia coli*. In exemplary embodiments, the microorganism may be a β-lactamase-nonproducing ampicillin-resistant (BLNAR) strain of *Haemophilus influenzae*. In other embodiments, the CABP may be due to *Enterobacter, Proteus. Serratia* or *Moraxella*. In further embodiments, the CABP may be due to *Enterobacter aerogenes, Proteus mirabilis, Serratia marcescens* or *Moraxella catarrhalis*.

When the methods involve co-administration of an STK1 inhibitor with an antibiotic, the antibiotic can be any suitable antibiotic compound described below. In some embodiments, the antibiotic can comprise a third generation cephalosporin (e.g., ceftriaxone or cefotaxime). In some embodiments, the bacterial infection can comprise a gram positive bacteria (e.g., *Staphylococcus aureus*). In certain embodiments, the bacterial infection can comprise a drug-resistant bacterial strain (e.g., a drug-resistant strain of *Staphylococcus aureus*, such as methicillin-resistant *Staphylococcus aureus*).

In some cases, the antibiotic (e.g., the cephalosporin) and the STK1 inhibitor can be administered to the subject within 48 hours or less of each other (e.g., within 24 hours or less of each other, within 12 hours or less of each other, within 8 hours or less of each other, within 4 hours or less of each other, within 2 hours or less of each other, or within 1 hour or less of each other. In certain cases, the antibiotic (e.g., the cephalosporin) and the STK1 inhibitor can be administered to the subject simultaneously (e.g., in the same dosage form, or in two separate dosage forms administered to the subject concurrently).

Also provided are methods of inhibiting Ser/Thr protein kinase (STK1) in a bacterial cell. These methods can comprise contacting the bacterial cell with an STK1 inhibitor described herein (e.g., Inh2-B1 (methyl 5-oxo-3-(phenyl carbamoyl-1-thioxo-4,5dihydro[1,3]thiazolo[3,4-a]quinazoline-8-carboxylate). These methods can further involve contacting the bacterial cell with an antibiotic compound that acts on the cell wall of a bacteria (e.g., a cephalosporin). In some embodiments, the antibiotic can comprise a third generation cephalosporin (e.g., ceftriaxone or cefotaxime). In some embodiments, the bacteria can comprise a gram positive bacteria (e.g., *Staphylococcus aureus*). In certain embodiments, the bacteria can comprise a drug-resistant bacterial strain (e.g., a drug-resistant strain of *Staphylococcus aureus*, such as methicillin-resistant *Staphylococcus aureus*).

Pharmaceutical Compositions

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein, or a pharmaceutically acceptable salt thereof, are suitable for parenteral administration. In some embodiments, the compounds provided herein are suitable for intravenous administration. In some embodiments, the compounds provided herein are suitable for oral administration. In some embodiments, the compounds provided herein are suitable for topical administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the pharmaceutical compositions provided herein are suitable for intravenous administration. In some embodiments, the pharmaceutical compositions provided herein are suitable for oral administration. In some embodiments, the pharmaceutical compositions provided herein are suitable for topical administration.

Also provided are pharmaceutical compositions which contain, as the active ingredient, a compound provided herein in combination with one or more pharmaceutically acceptable carriers (e.g. excipients). In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be, for example, in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in an effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The compositions provided herein can be administered one from one or more times per day to one or more times per week; including once every other day. The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a compound described herein can include a single treatment or a series of treatments.

Dosage, toxicity and therapeutic efficacy of the compounds provided herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

In some embodiments, the composition can further comprise an antibiotic compound described below (e.g., an antibiotic that acts on the cell wall of a bacteria, such as a cephalosporin). In certain embodiments, the antibiotic can comprise a third generation cephalosporin (e.g., ceftriaxone or cefotaxime).

Antibiotic Compounds

As discussed above, the compositions and methods described herein can further include the use of an antibiotic compound. In these compositions and methods, any suitable antibiotic known in the art may be used.

In general, antibiotic compounds are classified based on chemical structure and mode of action. In particular, antibiotics can be classified as (a) agents that inhibit the synthesis of bacterial cell walls, including the β-lactam class of antibiotics (e.g., penicillins, cephalosporins, or carbapenems) or other dissimilar agents such as vancomycin and bacitracin, (b) agents that act to permeabilize the cellular membrane causing a toxic release of intracellular material (e.g., detergents such as polymyxin). (c) agents that disrupt the function of 30S or 50S ribosomal subunits to interrupt protein synthesis (e.g., chloramphenicol, tetracyclines, or erythromycine), (d) agents that inhibit or block bacterial nucleic acid synthesis or metabolism (e.g., rifampin, rifabutin, or quinolones), and (e) agents that block or inhibit bacterial metabolism (e.g., trimethoprim or sulfonamides).

Examples of antibiotic agents include, but are not limited to, beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin, and the like), penicillinase-stable penicillins, acylamino and carboxypenicillins (such as piperacillin, azlocillin, mezlocillin, carbenicillin, temocillin, ticarcillin, and the like), and broader spectrum penicillins (such as streptomycin, neomycin, framycetin, gentamicin, apramycin, amikacin, spectinomycin, amoxycillin, ampicillin, and the like), cephalosporins, macrolides (such as tylosin, tilmicosin, aivlosin, erythromycin, azithromycin, spiramycin, josamycin, kitasamycin, and the like), lincosamides (such as lincomycin, clindamycin, pirlimycin, and the like), pleuromutilins (such as tiamulin, valnemulin, and the like), polypeptides, glycopeptides (such as vancomycin, and the like), polymixins (such as polymixin B, polymixin E and the like), sulfonamides (such as sulfamethazine, sulfadiazine, silver sulfadiazine, sulfatroxazole, sulfamethoxypyridazine, sulfanilamide, sulfamethoxazole, sulfisoxazole, sulfamnethizole, mafenide, and the like, alone or in combination with trimethoprim), chloramphenicol, thiamphenicol, florfenicol, tetracycline type agents (such as tetracycline, chlortetracycline, oxytetracycline, domeclocycline, doxycycline, minocycline, and the like), quinolones and fluoroquinolones (such as ciprofloxacin, enoxacin, grepafloxacin, levofloxacin, lomefloxacin, norfloxacin, ofloxacin, sparfloxacin, trovafloxacin, cinocacin, nalidixic acid, and the like), tiamulin, colistin, meropenem, sulbactam, tazobactam, methacycline, pyrimethamine, sulfacetamide, oxazolidinones, e.g., eperezolid, linezolid, N-((5S)-3-(3-fluoro-4-(4-(2-fluoroethyl)-3-oxy-1-p-piperazinyl)phenyl-2-oxy-5-oxazolidinyl) methyl)acetamide, (S)—N-((3-(5-(3-pyridyl)thiophen-2-yl)-2-oxy-5-oxazolidinyl)methyl)acetamide, 2,2-difluoro-N-({(5S)-3-[3-fluoro-4-(4-glycoloylpiperazin-1-yl)phenyl-1]-2-oxo-1,3-oxazolidin-5-yl}methyl)ethanethioamide, (S)—N-((3-(5-(4-pyridyl)pyrid-2-yl)-2-oxy-5-oxazolidinyl) methyl)acetamide hydrochloride, and the like, aminoglycosides (kanamycin, tobramycin, netilmicin, and the like), aminocyclitols, amphenicol, ansamycin, carbaphenern, cephamycin, rifampicin, monobactam, oxacephem, streptogramins (such as quinupristin, dalfopristin, and the like), cycloserines, mupirocin, urea hydroxamates, folic acid analogs (such as trimethoprim, and the like), antibiotic-type antineoplastic agents (such as aclarubicin, actinomycin D, actinoplanone, aeroplysinin derivative, Nippon Soda anisomycins, anthracycline, azino-micyin-A, busucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-Alb, fostriecin, glidobactin, gregatin-A, grincamycin, herbimycin, idarubicin, illudins, kazusamycin, kesarirhodins, menogaril, mitomycin, mitoxantorone, mutamycin, mycophenolate mofetil, neoenactin, oxalysine, oxaunomycin, peplomycin, pilatin, pirarubicin, porothramycin, pyrindamycin A, rapamycin, rhizoxin, rodorubicin, sibanomycin, siwenmycin, sorangicin-A, sparsomycin, steffimycin B, talisomycin, terpentecin, thrazine, tricrozarin A, zorubicin, systemic antibacterials (such as 2,4-diaminopyrimidine), nitrofuran sulfones, narbofloxacin, and the like, and combinations thereof.

In some embodiments, the antibiotic can comprise an agent that inhibits the synthesis of bacterial cell walls, such as a β-lactam antibiotic compound. The f-lactam class of antibiotics represent a large and important class of antibiotics whose overall effectiveness is threatened by the emergence of resistance, which is in particular, caused by the continued appearance of beta-lactamase enzymes in various bacteria.

The beta-lactam cephalosporin antibiotics are a group of semi-synthetic derivatives of cephalosporin C, an antimicrobial agent of fungal origin. They are structurally and pharmacologically related to the penicillins. The cephalosporin ring structure is derived from 7-aminocephalosporanic acid (7-ACA) while the penicillins are derived from 6-aminopenicillanic acid (6-APA). Both structures contain the basic beta-lactam ring but the cephalosporin structure allows for more gram negative activity than the penicillins and aminocillins. Substitution of different side chains on the cephalosporin ring allows for variation in the spectrum of activity and duration of action.

Cephalosporins are grouped into "generations" by their antimicrobial properties. The first cephalosporins were designated first generation while later, more extended spectrum cephalosporins were classified as second generation cephalosporins. Currently, three generations of cephalosporins are recognized and a fourth has been proposed. Significantly, each newer generation of cephalosporins has greater gram negative antimicrobial properties than the preceding generation. Conversely, the "older" generations of cephalosporins have greater gram positive coverage than the "newer" generations.

Examples of suitable cephalosporins that can be used in conjunction with the compositions and methods described herein include first generation cephalosporins, such as, Cefacetrile (cephacetrile), Cefadroxil (cefadroxyl; Duricef®). Cefalexin (cephalexin; Keflex®), Cephaloglycin, Cefalonium (cephalonium), Cefaloridine (cephaloradine), Cefalotin (cephalothin; Keflin®), Cefapirin (cephapirin; Cefadryl®), Cefatrizine, Cefazaflur, Cefazedone, Cefazolin (cephazolin; Ancef®, Kefzol®), Cefradine (cephradine; Velosef®), Cefroxadine, Ceftezole; second generation cephalosporins, such as, Cefaclor (e.g., Ceclor®, Distaclor®, Keflor®, Raniclor®, Cefonicid (e.g. Monocid®), Cefprozil (e.g., cefproxil; Cefzil®), Cefuroxime (e.g., Zinnat®, Zinacef®, Ceftin®, Biofuroksym®), Cefuzonam, Cefmetazole, Cefotetan, Cefoxitin, Carbacephems (e.g., loracarbef (Lorabid®)), Cephamycins (e.g., cefbuperazone, cefmetazole (Zefazone®), cefminox, cefotetan (Cefotan®), cefoxitin (Mefoxin®)); second generation cephamycins, such as, cefotetan or cefoxitin; third generation cephalosporins, such as, Cefcapene, Cefdaloxime, Cefdinir (Omnicef®), Cefditoren, Cefetamet, Cefixime (Suprax®), Cefmenoxime, Cefodizime, Cefotaxime (Claforan®), Cefpimizole, Cefpodoxime (Vantin®, PECEF), Cefteram, Ceftibuten (Cedax), Ceftiofur, Ceftiolene, Ceftizoxime (Cefizax®), Ceftriaxone (Rocephin®), Cefoperazone (Cefobid), Ceftazidime (Fortum®, Fortaz®), or Oxacephems (e.g. latamoxef); fourth generation cephalosporins, such as, cefepime (Maxipime®), cefclidine, cefluprenam, cefoselis, cefozopran, cefpirome (Cefrom®), cefquinome, or flomoxef; or fifth generation cephalosporins, such as ceftobiprole, ceftaroline, or ceftolozane, Other examples of cephalosporins include, for example, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime, or Nitrocefin.

In some embodiments, the cephalosporin can be a third generation cephalosporin. In certain embodiments, the cephalosporin can be Ceftriaxone. In certain embodiments, the cephalosporin can be Cefotaxime.

The examples below are intended to further illustrate certain aspects of the methods and compounds described herein, and are not intended to limit the scope of the claims.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: A Novel STK1-Targeted Small-Molecule as an "Antibiotic Resistance Breaker" Against Multidrug-Resistant *Staphylococcus aureus*

Results

STK1 and STP1 Reciprocally Regulate the Growth in *S. aureus* MW2 Strain.

Figure 9:
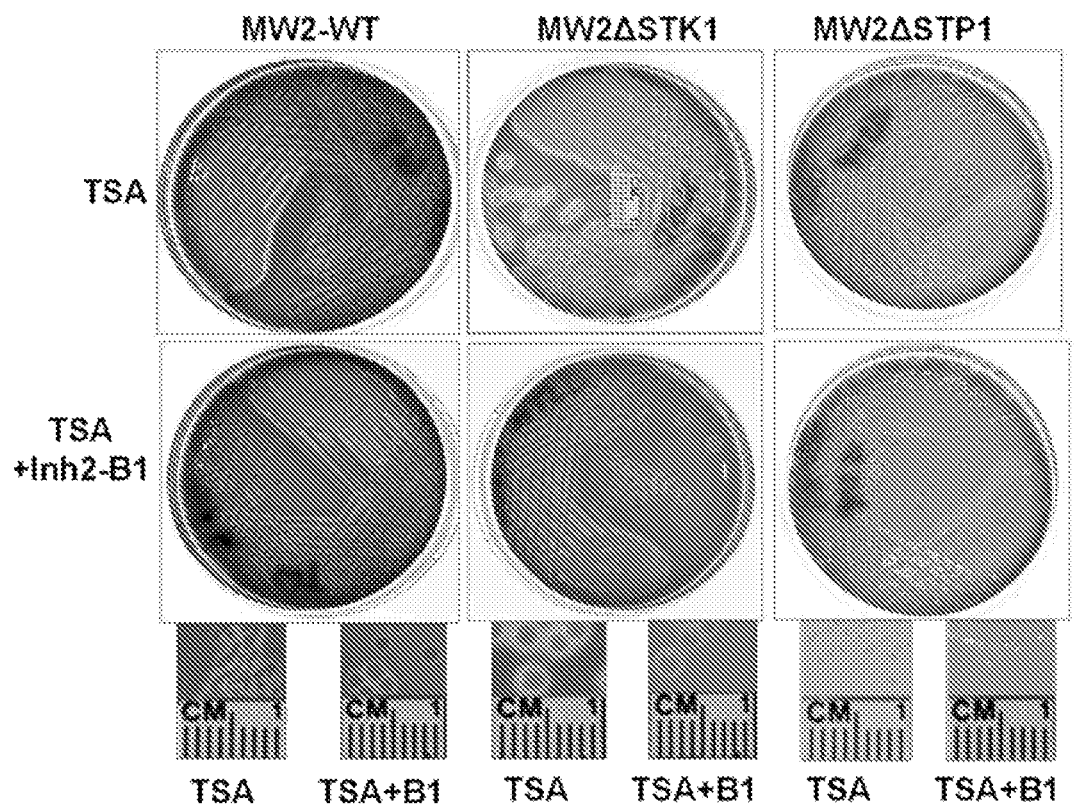
FIG. 9 shows the colony morphology any hemolysis patterns of *S. aureus* MW2-WT wild-type, and MW2ΔSTK1 and MW2ΔSTP1 mutant strains on TSA blood agar plates incorporated with or without 50 μM Inh2-B1. See the increased hemolysis around the colonies of the MW2ΔSTK1 mutant and absence of hemolysis around those of MW2ΔSTP1 mutant as depicted in the enlarged portion of certain representative colonies shown under each panel of the strain. A one centimeter bar is included to facilitate the determination of the relative size of colonies and corresponding hemolytic zones around them.

It has been reported that the growth of *S. aureus* isogenic mutants lacking STK1, but not STP1, is retarded when compared to the parent wild-type strains. Considering the wide range of prevailing strain variations in MRSA for virulence as well as drug resistance, ΔSTK1 and ΔSTP1 mutants were derived from a community-associated and highly pathogenic multidrug-resistant *S. aureus* strain (MW2) in the present investigation (FIG. 1). The impact of deletion of these genes on the growth as well as the susceptibility of the mutants against cell wall acting antibiotics was tested. In comparison to the Wild-type strain, MW2ΔSTK1 mutant showed colonies with a larger hemolytic zone (MW-WT) on blood agar plates. On the other hand, the MW2ΔSTP1 mutant strain developed non-hemolytic colonies (FIG. 9). These results concurred with those reported for similar mutants derived from *S. aureus* Newman strain. The growth of MW2ΔSTK1 and not MW2ΔSTP1 was retarded in chemically defined medium (CDM) supplemented with different carbohydrate sources indicating that the STK1 activity contributes to overall staphylococcal metabolic fitness (FIG. 1A). Electron microscopy of the MW2ΔSTK1 mutant in comparison to the MW2-wildtype (FIGS. 1B and 1E) revealed altered cell wall structures and defective cell septa in ~40% of cells (FIGS. 1C and 1F). These features were in contrast to the MW2ΔSTP1 mutant displaying intact and thick cell wall phenotypes (FIGS. 1D and 1G), as reported previously for *S. aureus* N315 and USA300.

Figure 10A:
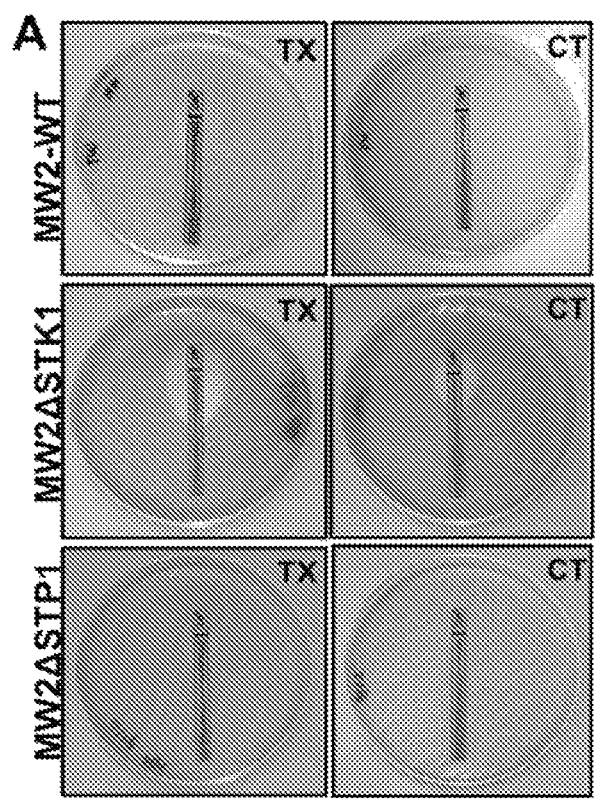
FIGS. 10A-10B illustrate the determination of susceptibility of *S. aureus* MW2 (WT, ΔSTK1 and ΔSTP1) strains to ceftriaxone, cefotaxime, and Inh2 using Miller Hinton-II media.

*S. aureus* STK1 has become an attractive target because of its close association with cell wall biosynthesis process and the observation revealing the increased susceptibility to cell wall acting antibiotics. Initial screening of antibiotic susceptibility by E™-test revealed increased susceptibility of MW2ΔSTK1 mutant to Ceftriaxone (MIC=4 µg/ml) and Cefotaxime (MIC=4 µg/ml) in comparison to the MW2-WT (>100 µg/ml) and MW2ΔSTP1 mutant (>100 µg/ml) (FIG. 10A). These results confirmed earlier findings with *S. aureus* N315 strains, and thus indicated that the innate antibiotic resistance of *S. aureus* can be substantially reduced by inhibiting the STK1 activity (FIG. 10A).

Identification of Small Molecule Inhibitors of STK1.

Based on the above results, it was hypothesized that STK1 could serve as a novel therapeutic target, and a putative inhibitor of STK1 serve as an "antibiotic resistance breaker." Further, this inhibitor, in turn, could potentiate the bactericidal activity of some of the cell wall acting antibiotics, which are deemed "inactive" or "failing" due to the emergence of MDRSA. Quinazoline-based small molecule compounds have been shown to inhibit kinase activity. Several amino-quinazoline-based inhibitors (Mitoxantrone, VI12112) have been described to inhibit the Ser/Thr kinase activity of mycobacterial PknB. In a library of 32 small molecule compounds that inhibited the growth of *S. aureus* RN4220 at varying concentrations ranging from 25-100 µM, it was found that the core structure of many of these compounds belonged to quinazoline group. It was, therefore, hypothesized that one or more compounds in this pre-screened library might possess STK1 inhibitory activity. Although STKs are transmembrane proteins, the isolated kinase domains of these proteins have been found to be soluble and when purified from *E. coli* retain enzymatic activity. Further, the crystal structure of the soluble STK1 kinase domain referred here as STKK1 has recently been solved. The purified recombinant STKK1 protein (first 280 aa of STK1) was therefore used for further experimental purposes.

Figure 2:
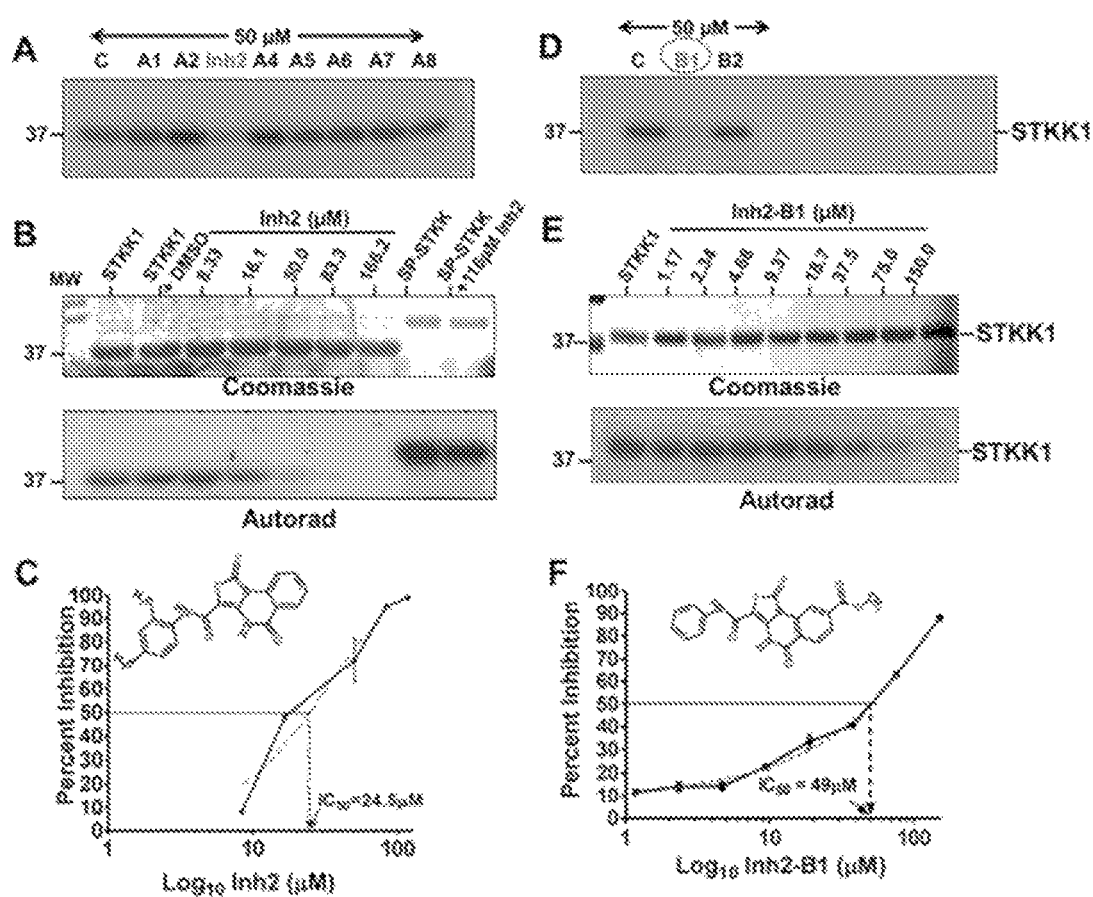
FIGS. 2A-F show identification of small molecule inhibitors targeted to *S. aureus* STK1. (A and D) Screening of Inh2-derivatives (50 μM as indicated) for their ability to inhibit the kinase activity of *S. aureus* STKK1. (B and E) Coomassie-stained gels and corresponding autoradiograph show the dose-dependent inhibitory activity of a small molecule inhibitors. (B) Inh2 (N-(2,4-Dimethylphenyl)-5-oxo-1-thioxo-4,5-dihydro [1,3]thiazolo[3,4-α] quinazoline-3-carboxamide) and (E) Inh2-B1 [Methyl 5-oxo-3-(phenyl carbamoyl)-1-thioxo-4,5dihydro[1,3]thiazolo[3,4-a]quinazoline-8-carboxylate] targeted to *S. aureus* STKK1 (the soluble kinase domain of STK1, 280 aa). (C and F) Quantitative analysis ($IC_{50}$ concentration) of Inh2 and Inh2-B1-mediated inhibition of STKK1 activity after 5 min preincubation. Each data point represents an average percent inhibition of three individual readings of radioactivity incorporation (radioactive counts per minute or CPM) (Mean±SEM) in protein bands of samples treated with different concentrations of the inhibitor in comparison to control samples. CPM measured in the protein band of the control sample without inhibitor was treated as 100% incorporation or 0% inhibition.
Figure 10B:
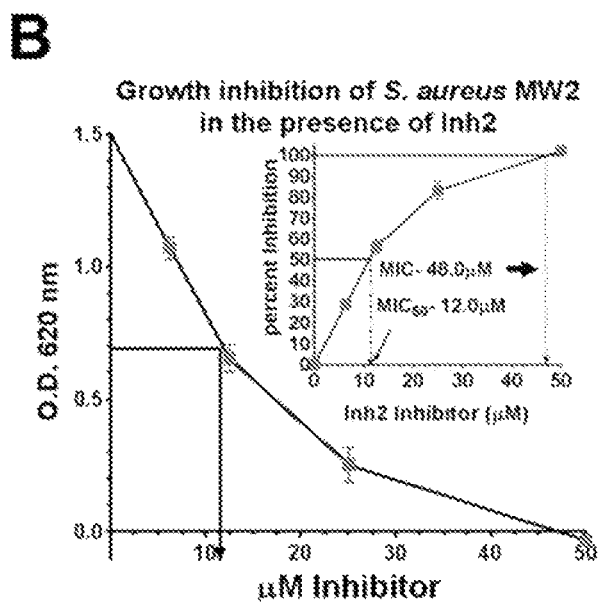
Figure 11:
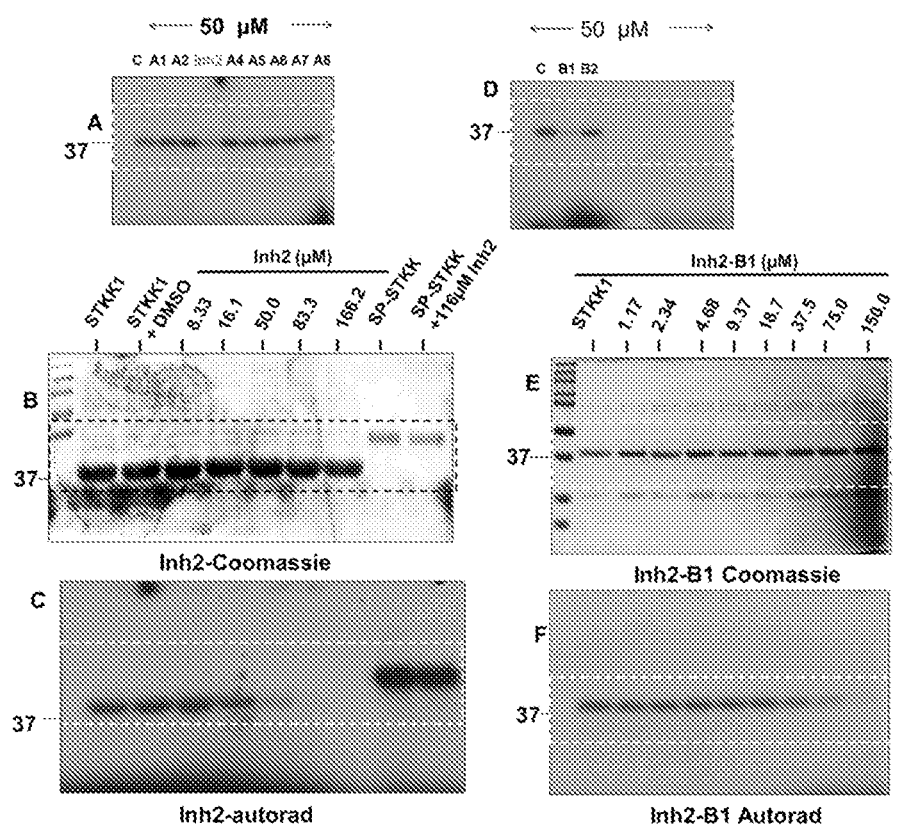
FIGS. 11A-11F show the screening of Inh2-derivatives for STKK1 phosphorylation inhibition. (A and D) Screening on Inh2 derivatives (50 μM as indicated) for their ability to inhibit the kinase activity of *S. aureus* STKK1. (B and E) Coomassie-stained gels and corresponding autoradiograph. (C and F) show the dose-dependent inhibitory activity of two small molecule inhibitors, (B) Inh2 (N-(2,4-dimethylphenyl)-5-oxo-1-thioxo-4,5-dihydro-[1,3]thiazolo[3,4-α] quinazoline-3-carboxamide) and (E) Inh2-B1 (methyl 5-oxo-3-(phenyl carbamoyl)-1-thioxo-4,5dihydro[1,3]thiazolo[3,4-a]quinazoline-8-carboxylate), targeted to *S. aureus* STKK1 (the soluble kinase domain of STK1, 280 aa). The dotted rectangles represent the portion of each picture shown in FIG. 2.
Figure 12A:
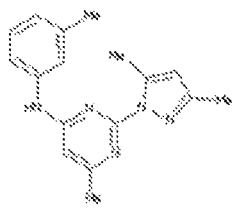
FIGS. 12A-12B show the determination of $IC_{50}$ concentrations of Inh-31 (A) and Inh-32 (B). Dotted lines depict regression lines. Each data point represents an average reading obtained from two independent experiments.
Figure 12A:
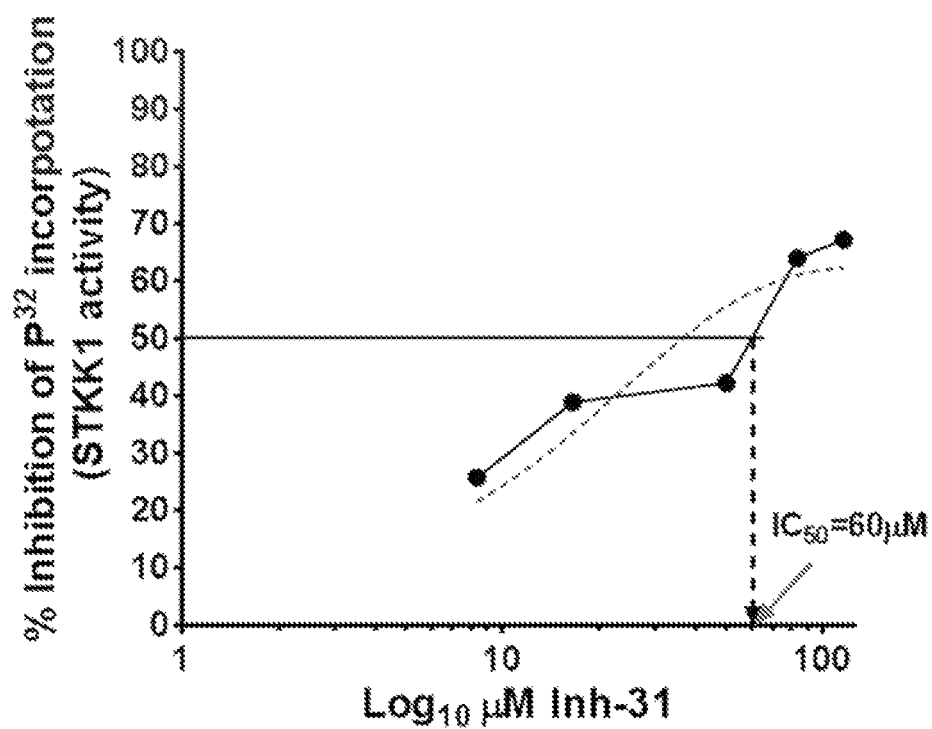
Figure 12B:
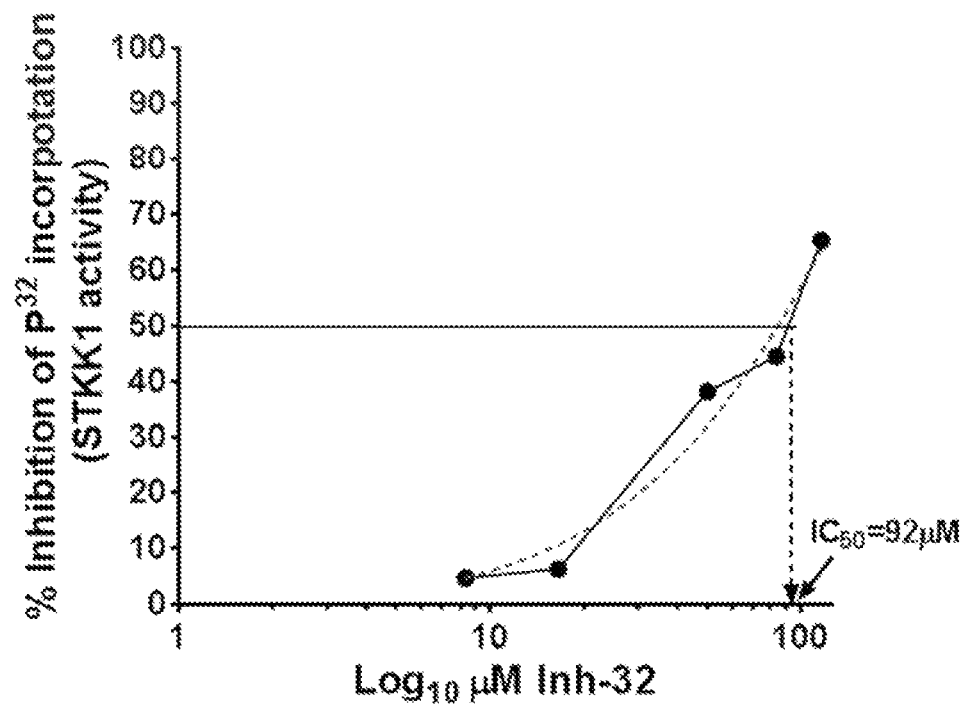
Figure 13:
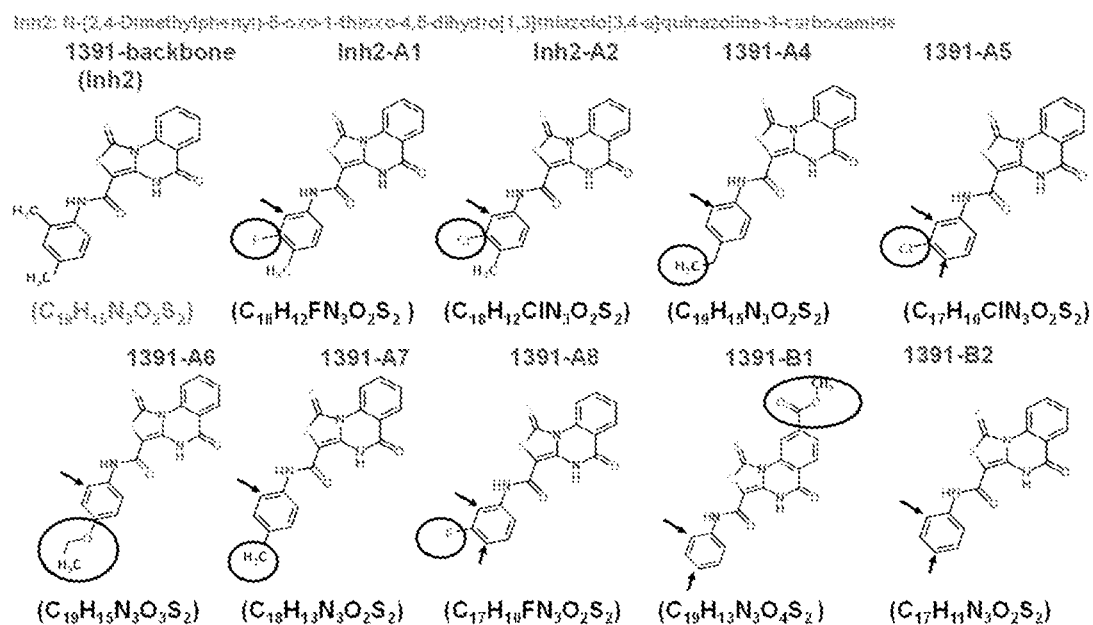
FIG. 13 shows the structure of Inh2 (compound 1391) as well as some of its derivatives. Circled areas denote the location of the side chain modification. The arrows denote the site of the original side chain that was deleted to modify the Inh2 to arrive at the new structure.

Upon screening of these pre-screened compounds for their ability to inhibit the in vitro autophosphorylation activity of STKK1, Inh2 (381.5 Da, FIG. 2A-2C, FIG. 11A-11C), Inh31 (293.4 Da, FIG. 12A) and Inh32 (293.4 Da, FIG. 12B) were identified as three potential candidates. Maximum inhibition of the kinase activity of STKK1 was observed using Inh2 ($IC_{50}$ 24.5 µM) (FIG. 2A-2C. FIG. 11A-11C) followed by Inh31 (60 µM) (FIG. 12A) and Inh32 (92.0 µM) (FIG. 12B). We, therefore, focused on Inh2, which is chemically characterized as N-(2,4-Dimethylphenyl)-5-oxo-1-thioxo-4,5-dihydro[1,3]thiazolo[3,4-a]quinazoline-3-carboxamide (FIG. 2B, FIG. 13). The Inh2 compound also appeared to be specific for staphylococcal STK1, since even at 116 µM concentration, it did not inhibit autophosphorylation of *S. pyogenes* SP-STK (FIGS. 2B, 11B, 11C). Although the MW2 mutant lacking STK1 displayed retarded growth (FIG. 1), STK1 as such is not essential for bacterial survival. However, in the broth dilution-based antibiotic susceptibility assays, the $IC_{50}$ concentration of Inh2 for MW2 was found to be 12.0 µM and minimum inhibitory concentration of 48 µM indicating that Inh2 can have an additional off-target activity (FIG. 10B). Inh2 was, therefore, used as a lead compound to obtain relevant derivatives that show a comparable Ser/Thr kinase inhibitory activity and phenotypic characteristics of the MW2ΔSTK1 mutant, i.e., retarded growth but not bactericidal activity.

To validate and establish the physiologically relevant chemical inhibition of STK1 activity by Inh2, ten derivatives were synthesized, adhering to the Lipinski RO5 rule using the on-line tool ZINC (http://zinc.docking.org) (FIG. 13). All ten derivatives were then examined for their ability to inhibit the kinase activity of STKK1 as well as growth inhibition of *S. aureus* MW2 as described above. Only Inh2-B1 [Methyl 5-oxo-3-(phenyl carbamoyl)-1-thioxo-4,5dihydro[1,3]thiazolo[3,4-a]quinazoline-8-carboxylate] inhibited kinase activity of STKK1 ($IC_{50}$=49 µM) (FIG. 2D-2F, and FIG. 11D-11F) with growth even at concentration of >50 µM as shown below. Inh2-B1 did not show any changes in the hemolysis pattern of colonies of MW2-WT. MW2ΔSTK1 or MW2ΔSTP1 (FIG. 9) indicating that increased hemolysis may not be the outcome of direct STK inhibition but by the factors modulated within the downstream signaling pathways which may also be influenced by other co-regulator.

Inh2 and Inh2-B1 Compete with ATP for Binding to the Catalytic Domain of STK1.

To determine the in vivo binding ability of Inh2 and Inh2-B1 to STKK, the whole cell lysate of *S. aureus* MW2 was subjected to solid-phase ATP affinity chromatography. Bound proteins of the whole cell lysates to the ATP-column were eluted with 50 µM Inh2 and Inh2-B1 inhibitors, and subsequently resolved by SDS-PAGE, and visualized by Coomassie staining or electrotransferred to a PVDF membrane. Immunoblot analysis using an anti-STK1 antibody revealed the presence of STK1 in the Inh2- and Inh2-B1-eluted fractions (FIGS. 3A and 3B). When the experiment was repeated with group A *Streptococcus* (*S. pyogenes*) whole cell lysates, Inh2 did not elute the bound SP-STK (FIG. 3C). Similar results were also obtained by using Inh2-B1 instead of Inh2. To confirm these findings, the purified recombinant *S. aureus* STKK1 protein and *S. pyogenes* SP-STKK protein were subjected to solid-phase-ATP-column chromatography as described above and eluted with Inh2-B1. The latter could elute only the *S. aureus* STKK1 protein (FIG. 3D) and not *S. pyogenes* SP-STKK protein (FIG. 3E). These results indicated that Inh2-B1 did not target *S. pyogenes* SP-STK in vivo as was observed by in vitro assays (FIG. 2A-2F).

Figure 14:
FIG. 14 is a comparison of molecular docking analysis-based binding affinities of Inh2 and its derivatives with the crystal structure of the kinase domain of *S. aureus* STK (PDB ID 4EQM).
Figure 14:
Figure 14:
Figure 14:
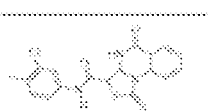
Figure 14:
Figure 14:
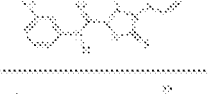
Figure 14:
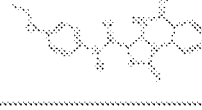
Figure 14:
Figure 14:
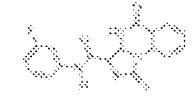
Figure 14:
Figure 14:
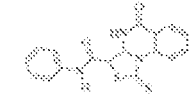

Further, to define the binding site of the inhibitor within the catalytic site of the STK1 protein, the small molecule inhibitors (Inh2 and all Inh2-derivatives including Inh2-B1) were subjected to molecular docking analysis. The latter was achieved by employing blind-docking on the available 3D structure of the kinase domain of STK1 (PDB 4EQM) (FIG. 3F, FIG. 14). By employing the Autodock grid (126×71×71) on this model and using the Lamarckian genetic algorithm, 200 runs were examined with 300 random individuals in the first population for each docking simulation. The lowest-energy conformation of each inhibitor was chosen, clustered, and ranked based on the energy score according to an RMSD cutoff of 3 Å. This cluster was found to localize in the ATP-binding pocket (FIG. 3F). Subsequently, narrow grids of dimensions 50×50×50 were employed in the region containing the inactive ATP analog, ANP. The focused or targeted docking was reiterated to identify clusters with the highest number of populated clusters (conformers) and lowest energy for Inh2, ANP, as well as nine Inh2-derivatives (FIG. 14). This series of simulation placed Inh2 in a position that is superimposable to the ATP binding site (FIG. 3G). In the 4EQM structure, five residues K39, E88, Y89, I90, and L140 were found to form an interaction network with bound ANP (inactive ATP) (FIG. 3G, see also FIG. 3J). The docking analysis identified six additional residues S22, V24, A37, M87, T94, and F150 in the proximity of Inh2 (FIG. 3H). In this model, Inh2 interacted with the protein at high affinity (−10.82 kcal $mol^{-1}$ with 68 conformers (FIG. 3J and FIG. 14). Interestingly, among all ten derivatives. Inh2-B1 showed the highest theoretical affinity for the catalytic domain of the STKK1 (−11.58 kcal $mol^{-1}$ with 21 conformers FIG. 3J and FIG. 14). Docking analysis also revealed the interaction of Inh2-B1 compound with a glycine-rich loop (G17-G19) as well as additional interacting amino acid side chains of L16 and G92, forming a unique pose that is different from that of ANP and Inh2 (FIG. 3J). A comparison of sequences encompassing the catalytic domain of various Gram-positive STKKs also indicated that a motif containing $G^{17}GGG^{20}$ residues is uniquely present only in *S. aureus*, unlike GRGG in STKs of other Gram-positive pathogens (FIG. 3K). This comparison also concurs with the molecular docking-based predictive analysis of the affinity of Inh2-B1 for *S. aureus* STKK1 and supports the inability of Inh2 to inhibit *S. pyogenes* SP-STKK.

Inh2-B1 Serves as "Antibiotic Resistance Breaker" and Rejuvenates the Lost Activity of Cell Wall Acting Antibiotics Since the STK1 is not essential for bacterial survival and its absence results in retardation of growth, an end-point bactericidal assay was done, employing the Checkerboard titration method followed by a time-to-kill assay using the broth dilution method. The 96-well plate-based checkerboard titration assays were performed using the fixed number of CFUs of MW2 strain, and the survival of the bacteria was measured on solid agar plates as an end-point result. The presence of ≥1 CFU of the wild-type MW2 strain was noticed only in the wells that had ≤50 µM of Inh2-B1, ≤75.00 µM of Ceftriaxone or ≤110 µM of Cefotaxime. Further analysis revealed the growth of MW2 even up to a concentration of 90 µM Inh2-B1 (i.e., Minimum bactericidal concentration [MBC] of 100 µM), 125 µM Ceftriaxone (i.e. MBC 151.15 µM i.e., 100 µg/ml) or 176 µM of Cefotaxime (MBC of 220 µM i.e. 100 µg/ml). Additionally, in the presence of 50 µM of Inh2-B1, the MBC of Ceftriaxone for MW2 reduced to 0.59 µM. i.e., 0.39 µg/ml (256-fold reduction) (FIG. 15A), and that of Cefotaxime reduced to 27.5 µM, i.e., 12.5 µg/ml (8-fold reduction) (FIG. 15B). The cut-off value to designate clinical isolates of *S. aureus* for antibiotics, including Ceftriaxone (TX) and Cefotaxime (CT) as susceptible, is less than 4 µg/ml (i.e., <4.8 µM of TX, and <7 µM of CT). These results, thus, indicated that Inh2-B1 serves as an antibiotic resistance breaker and enhances the bactericidal activity of Ceftriaxone more efficiently than of Cefotaxime on drug-resistant *S. aureus* (FIG. 15). To substantiate this static culture/endpoint-based results, in subsequent experiments. CFU counts of MW2-WT grown in the presence of various concentrations of Inh2-B1 were examined over a period of 16 h. Even at 100 µM of Inh2-B1, MW2 showed more than 3 log increase in growth, i.e. from the starting inoculum concentration of 4×10⁶ CFU to 1.8±1.0×10⁹ CFU growing (FIGS. 4A and 4B). Observed growth inhibition was therefore treated in comparison to the wild-type (~2 log reduction) at a very high concentration of Inh2-B1 as resistant or as minimal inhibition. Such inhibition could be an outcome of the non-specific toxic effect associated with the compound. Similarly, it was also determined CFU counts of MW2-WT and MW2ΔSTK1 strains each grown in the absence or the presence of 50 µM of Inh2-B1 and 1.5 µM Ceftriaxone (1 µg/ml) or 3 µM Cefotaxime (1 µg/ml) for 16 h employing the broth dilution method. In the presence of only Inh2-B1 or only Ceftriaxone, or Cefotaxime, the growth pattern of the wild-type remained unaltered even after 16 h of incubation (FIGS. 4C, 4D). As expected, in the absence of STK1 activity, the growth of MW2ΔSTK1 reduced significantly in the presence of Ceftriaxone because of the increased susceptibility to cell wall acting antibiotics (FIGS. 4E and 4F). In the presence of Inh2-B1, the growth pattern of the MW2 wild-type was slightly retarded and mimicked to that of MW2ΔSTK1 as a result of the chemical inactivation of STK1 activity as described above (FIGS. 4A and 4B). However, in the presence of the mixture of 1.5 µM Ceftriaxone (1 µg/ml) and 50 µM Inh2-B1, the growth of the MW2 wild-type was dramatically inhibited similarly to MW2ΔSTK1 (FIGS. 4C and 4D). Further, to address whether MW2 or STK1 could become refractory to a potential combined therapy, the S. aureus MW2 wild-type strain was grown in the presence of suboptimal dose of Inh2-B1 alone and combination with Ceftriaxone and Cefotaxime (25 µM Inh2-B1 and 3 µM of Ceftriaxone or 3 µM Cefotaxime) for consecutive 10 generations. The passaged strain in both cases did not show any changes in the stk1 gene as determined by PCR and DNA sequencing indicating that that STK1 activity remained intact. Further, the bactericidal activity of Ceftriaxone also remained intact in the presence of 50 µM Inh2-B1 as described above. Together these results supported the notion that STK1 is playing an important role in certain essential and physiologically relevant cellular activities, such as cell wall biosynthesis. These results confirmed that Inh2-B1 indeed serves as an antibiotic resistance breaker.

Figure 16:
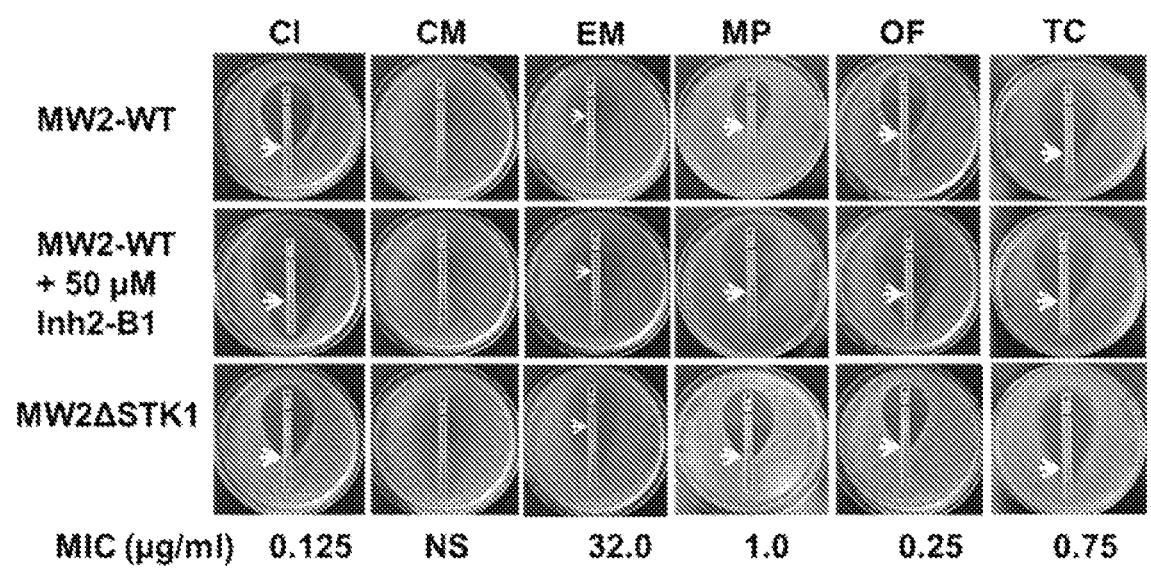
FIG. 16 shows susceptibility patterns of *S. aureus* MW2-WT and *S. aureus* MW2ΔSTK1 against various antibiotics as determined by E-test. Antibiotic susceptibility of MW2-WT strain was measured in the presence and absence of 50 μM Inh2-B1 and their comparison with *S. aureus* MW2ΔSTK1 mutant strain carried out in the absence of Inh2-B1. White arrows indicate the MIC values (μg/ml) shown underneath each panel of antibiotics. CI—ciprofloxacin, CM—clindamycin, EM—erythromycin, MP—meropenem. OF—ofloxacin, and TC—tetracycline.

Inhibitory activity of Inh2-B1 on S. aureus MW2 at high concentration prompted the question of whether Inh2-B1 would also act synergistically with antibiotics other than those that target cell wall biosynthesis. Changes in antibiotic susceptibility patterns of MW2-WT were noted for other antibiotics in the presence and absence of Inh2-B1 by E-test™. In the same assay, the MW2ΔSTK1 mutant was used as a positive parallel control to compare its susceptibility pattern with that of the MW2-WT strain in the presence of Inh2-B1. The results demonstrated that Inh2-B1 did not change susceptibility patterns of any of the 6 antibiotics (Ciprofloxacin[CI], Clindamycin [CM], Erythromycin [ER], Meropenem [MP]. Ofloxacin [OF], and Tetracycline [TC]) for the MW2 strain. MIC values of all antibiotics for MW2-WT in the presence and absence of Inh2-B1 and those of MW2ΔSTK1 remained unaltered indicating that the observed synergistic activity of Inh2-B1 is mediated essentially via STK1 inhibition and by interfering with cell wall biosynthesis (FIG. 16).

Inh2 and Inh2-B1 Treatment Affect the Cell Wall Biosynthesis Via Regulating Expression of Cell Wall Hydrolase-Encoding Genes.

Figure 5:
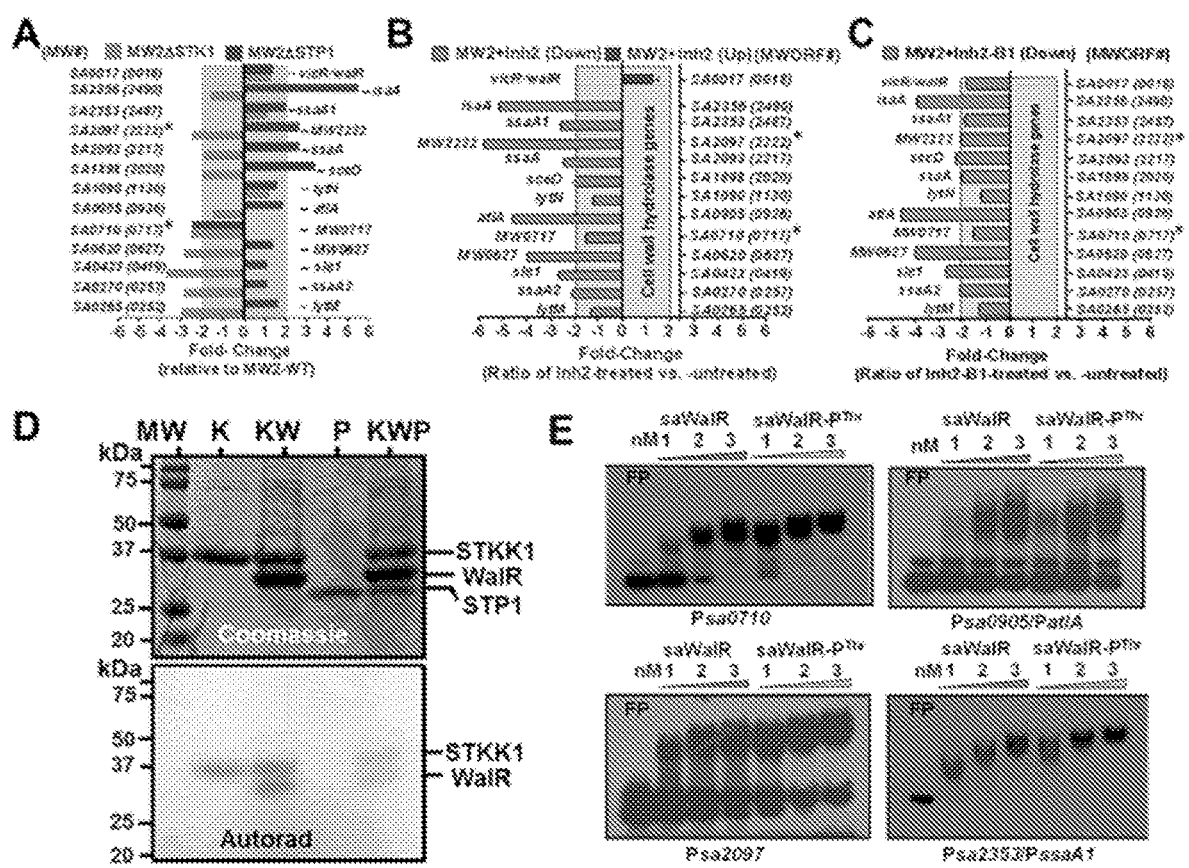
FIGS. 5A-E show Inh-2 and Inh2-B1 treatment adversely affect the expression of genes encoding cell wall hydrolases in S. aureus via inhibiting STK1 activity. (A) qRT-PCR-based mRNA expression profiles of cell wall hydrolase genes in MW2ΔSTK1 and MW2ΔSTP1 mutants vs. MW2-WT show the reciprocal regulation in the absence of STK1 and STP1. Numbers shown on the Y-axis refer to ORF (open reading frame) numbers of the cell wall hydrolase-specific genes present in the S. aureus N315 genome and numbers within parentheses refer to the corresponding genes present in the MW2 genome. qRT-PCR-based mRNA expression profiles of cell wall hydrolase genes in S. aureus MW2-WT wild-type strain treated with (B) Inh2 and (C) Inh2-B1. Each horizontal bar represents an average value (Mean±S.D.) from three different experiments each with three technical replicates. (D) STK1 and STP1-mediated reversible phosphorylation of S. aureus WalR. Phosphorylation assays were carried out in the phosphorylation buffer containing $\gamma^{32}$P-ATP as described in the Materials and Methods section. The upper panel in (D) represents the Coomassie-stained SDS-page gel with differentially migrated S. aureus STKK1(K), WalR (W), and STP1 (P) proteins. Each lane represents the combination of one or more of these proteins present in the phosphorylation, dephosphorylation, and control reaction mixtures. The lower panel is a corresponding autoradiogram of the upper panel. Numbers on the left represent molecular weight markers (MW) in kDa. (E) EMSAs showing the impact of the binding of different concentrations of the recombinant WalR and the STKK1-phosphorylated WalR to the promoter region of four genes-specific (SA0710, SA0905, SA2097, SA2353) $\gamma^{32}$P-DNA probe on their electrophoretic migration in the gel.

In S. pyogenes, SP-STK and SP-STP reciprocally regulate the expression of the key cell wall hydrolase, CdhA, possibly via reversible phosphorylation of WalR as also recently reported in B. subtilis. The WalR-mediated regulation of cell wall hydrolases is also observed for S. pneumoniae and S. aureus. Cell wall hydrolases play a crucial role in the modulation of the cell wall structure, muropeptide-turnover/recycling, cell shape, cell division, growth as well as innate immune detection and ultimately fitness, virulence, and drug resistance. A previous report on transcriptome analysis of S. aureus NCTC 8325 mutants lacking respective stk1 gene has shown that the observed defective cell wall is likely due to the altered regulation of cell wall hydrolases required for the cell wall biosynthesis. The expression profile of genes encoding cell wall hydrolases in S. aureus MW2 wild-type strain and mutants lacking STK1 and STP1 by qRT-PCR analysis were examined. These results were then compared with those obtained with wild-type strain treated with and without Inh2 and Inh2-B1. This analysis revealed reciprocal regulation of 9 out of 13 tested genes in MW2ΔSTK1 and MW2ΔSTP1 mutants when compared to the MW2-WT strain (FIG. 5A). Out of these nine differentially altered genes, The MW2ΔSTK1 mutant strain displayed significantly reduced transcript abundance (i.e. exceeding cut off limit of 2-fold) of four (SA0620. SA0423, SA270, and SA0265) out of those nine differentially regulated genes. Similarly, the MW2ΔSTP1 mutant displayed significantly upregulated transcript abundance of three (SA2356, SA1898. SA 2093 and SA2356) of those nine genes. In contrast to these patterns, unique differential regulation of two remaining genes (SA0710, and SA2097) was observed. While the transcript abundance of SA0710 was found to be significantly decreased (>2-fold) in MW2ΔSTK1 as well as MW2ΔSTP1 mutants, the reciprocal regulation of another gene. SA2097, was observed in the absence of stk1, as well as stp1 genes i.e. decreased and transcript abundance in MW2ΔSTK1 and MW2ΔSTP1 mutants respectively. Notably, there was no significant change in the expression level of the walR/VicR (SA0017/MW0018) gene in the absence of either the stk1 or stp1 gene, indicating that the observed differential regulation of cell wall hydrolase genes was not directly due to the differential transcript abundance of the walR gene. Similar to the down-regulation of cell wall hydrolase genes in the MW2ΔSTK1 mutant, treatment of the MW2-WT strain with Inh2 and Inh2-B1 also caused the down-regulation of cell wall hydrolase-encoding genes (FIGS. 5B and 5C). The two-component regulator, WalR, has been shown to modulate the transcription profile of several cell wall hydrolase genes, including those encoding LytM, AtlA, SsaA, and IsaA proteins in S. aureus. Further, the deletion of either the stk1 or stp1 gene did not alter the walR transcript abundance. It was therefore examined whether the observed altered transcription profile was due to the post-translational modification of WalR. To test this, recombinant WalR to the STK1- and STP1-mediated in vitro phosphorylation and dephosphorylation. In vitro phosphorylation results, revealing STK1- and STP1-mediated reversible phosphorylation of the recombinant WalR protein concurred with the hypothesis and the notion that STK1 might modulate and fine tune the expression of cell wall hydrolases via functional status of WalR (FIG. 5D). To confirm this, posttranslationally modified WalR differentially binds to promoters of some of the cell wall hydrolase genes were examined, which showed differential transcript abundance. To determine this binding, an electrophoretic mobility shift assay (EMSA) was used, using recombinant WalR and STKK1-phosphorylated WalR, and determined its ability to bind to the promoter regions of four genes. As described above (FIG. 5A), two of these genes (SA0710 and SA2097) were differentially regulated, and two showed no changes in their expression when either the stk1 or stp1 gene was deleted, or when STK1 activity was chemically inhibited with Inh2 or Inh2-B1 (FIGS. 5B and 5C). EMSA was performed as described in the Materials and Methods section. The results showed that the STKK1-phosphorylated WalR protein, in comparison to the unphosphorylated WalR, bound specifically to the $^{12}$P-labeled SA0710 and SA2097 DNA probe with significantly high efficiency (>2 fold Bound/free ratio) (FIG. 5E). However, this increased promoter binding efficiency of WalR-P was not observed for other two genes (SA0905 and SA2353), which served as negative control (FIG. 5E). In the presence of 100× cold-probes specific to all four genes, the binding of corresponding $^{32}$P-labeled DNA probes to WalR was completely inhibited. Together, these results revealed the impact of the Inh2-B1-mediated chemical inhibition of the STK1 activity similar to the deletion of the stk1 gene in S. aureus indicating that STK1 contributes to the WalR binding to its certain promoters and is able to modulate the transcription of corresponding downstream genes. Thus, the observed effect of Inh2-B1 can be mediated via inhibiting STK1-mediated WalR phosphorylation and modulating the ability of phosphorylated WalR to regulate transcription of cell wall hydrolase genes and resulting expression of cell wall hydrolases and subsequently the cell wall biosynthesis in S. aureus.

Inh2-B1 Inhibits S. aureus Biofilm Formation.

Figure 6:
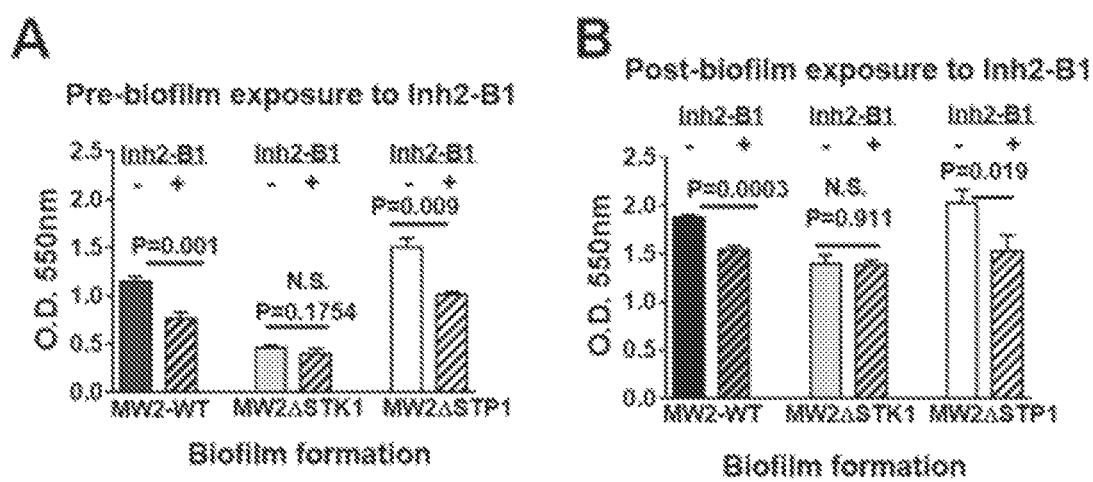
FIGS. 6A-B show Inh2-B1 disrupts the formation S. aureus biofilms. (A) Biofilms formation by S. aureus MW2 wild-type, MW2ΔSTK1 and MW2ΔSTP mutant strains in the absence and presence of 25 µM Inh2-B1 after 48 h. (B) Effect of Inh2-B1 (25 µM) on the preformed biofilms by S. aureus MW2 wild-type, MW2ΔSTK1, and MW2ΔSTP1 mutant strains. Biofilm formation was quantitatively estimated after 48 h of incubation by the crystal violet staining method. Bar diagrams represent average values (Mean±S.D) obtained for different parameters from three independent cultures each with three technical replicates. P<0.05 was treated as a significant difference.

S. aureus biofilm formation is a complex multifactorial phenomenon. Since cell wall hydrolases play a crucial role in cell wall biosynthesis and the biofilm formation, it was examined whether Inh2-B1 alone can inhibit the biofilm formation by S. aureus employing the crystal violet stain method. The results shown in FIG. 6 revealed that the S. aureus mutant lacking STK1 formed poor biofilms when compared to that of the wild-type (P=0.0005). MW2ΔSTP1 mutant, on the other hand, formed comparable and robust biofilms comparable to the wild-type strain (P=0.1361). In the same assay, when the biofilm formation was allowed to occur in the presence of Inh2-B1, the MW2 wild-type (P=0.001), as well as the MW2ΔSTP1 mutant strains (P=0.009) but not the MW2ΔSTK1 strain (P=0.175) showed the significantly decreased formation of biofilms (FIG. 6A). Subsequently, it was tested Inh2-B1 could reduce the preformed biofilms. Indeed as expected, further incubation resulted in the increased recovery of the biofilms in all strains. Despite this increase, a similar pattern of the significant reduction in biofilm formation was observed when individual biofilms of the MW2 wild-type (P=0.0003) and MW2ΔSTP1 (P=0.001) were further treated with Inh2-B1 for 48 h. Inh2-B1 treatment, however, did not affect biofilms of MW2ΔSTK1 (P=0.911) (FIG. 6B). Further, the decrease in biofilm formation by Inh2-B1-treated MW2-WT and MW2ΔSTP1 was comparable to that of MW2ΔSTK1 treated with or without Inh2-B1 indicating that the observed reduction is due the chemical inactivation of STK1 activity in these strains. Together these results indicated that Inh2-B1, in addition to its role as an antibiotic resistance breaker, played a significant role in the regulation of biofilm formation and in the disruption of preformed biofilms via inhibiting the STK1 activity.

Inh2-B1 Displays Cell-Dependent Minimal to No Cytotoxicity.

To investigate the potential therapeutic value of Inh2-B1, cytotoxic properties of the compound were first examined in vitro. Confluent cultures of an established human pharyngeal carcinoma cell lines (Detroit 562), and normal cell lines (BEAS-2B) were incubated in the presence of increasing concentrations of Inh2-B1 (1.56-100 μM), for 24 h in a $CO_2$ incubator. Lactate dehydrogenase (LDH) activity was then assessed using a standard chromogenic substrate in the supernatant of each well. While BEAS-2B cell lines showed relatively higher cytotoxicity (~15%). Detroit 562 human lung cell lines showed less than 5% lysis (FIGS. 7A and 7B). Since many kinase inhibitors have been therapeutically used to inhibit tumor cell proliferation but not lysis, the impact of Inh2-B1 was examined on cell proliferation of these human cell lines by MTT assays. Inh2-B1 did not affect cell proliferation of Detroit 562 cell lines even at 100 μM concentration (FIG. 7C). However, cell proliferation inhibition was observed in BEAS-2B in the presence of Inh2-B1 only at 100 μM (~40%, P<0.001) and 50 μM (~20%, P<0.001) concentration (FIG. 7D). Together these results indicated that while some cell type may display toxic effects at a very high concentration of Inh2-B1, Inh2-B1 may remain nontoxic in vivo to most cells at a low therapeutic concentration.

Inh2-B1 Serves as an Antibiotic-Resistant-Breaker and Enhances Bactericidal Activity of Ceftriaxone and Cefotaxime in the S. aureus Septicemia Mouse Model.

Figure 7:
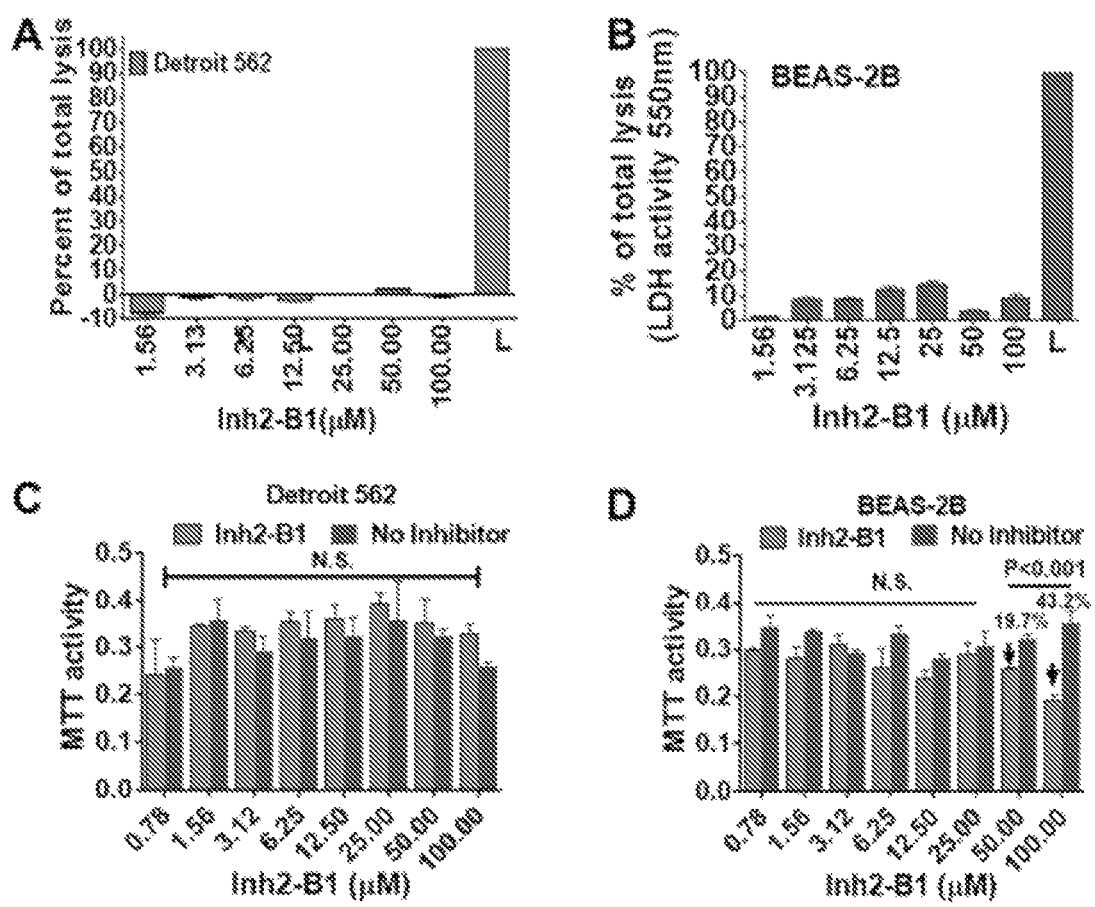
FIGS. 7A-D show human cell-dependent cytotoxic properties of Inh2-B1. (A and B) Lactate dehydrogenase (LDH) activity in Inh2-B1-treated human cell lines grown in 96-well tissue culture plates. LDH activity was measured in the supernatants of (A) Detroit 562, and (B) BEAS-2B cells lines treated with different concentrations of serially Inh2-B1 (serially 2-fold dilution-100 µM-1.56 µM) for 24 h. LDH activity in individual wells was detected spectrophotometrically ($\gamma$=490 nm) and normalized to the LDH activity of the whole cell lysates of confluent cultures of different cell lines (L), which was treated as 100% lysis. (C and D) Effect of different concentrations (100 µM-0.78 µM) of Inh2-B1 on the proliferation of (C) Detroit 562, and (D) BEAS-2B cell lines grown in 96 well tissue culture plates as determined by the MTT test. The cells were treated with Inh2-B1 in a final volume of 100 µl for 24 h. At the end of incubation, tissue culture medium was removed and replaced with fresh 100 µl of the medium containing MTT solution (0.5 mg/ml) and further incubated for 4 h. The purple color of formazan salt crystals formed in each well was solubilized and spectrophotometrically analyzed ($\gamma$=570 nm) as described in the Materials and Method section. Each bar shows the average (Mean±S.D) reading of three different experiments each carried in triplicate wells. P<0.05 treated as a significant difference. N.S.=not significant.
Figure 8:
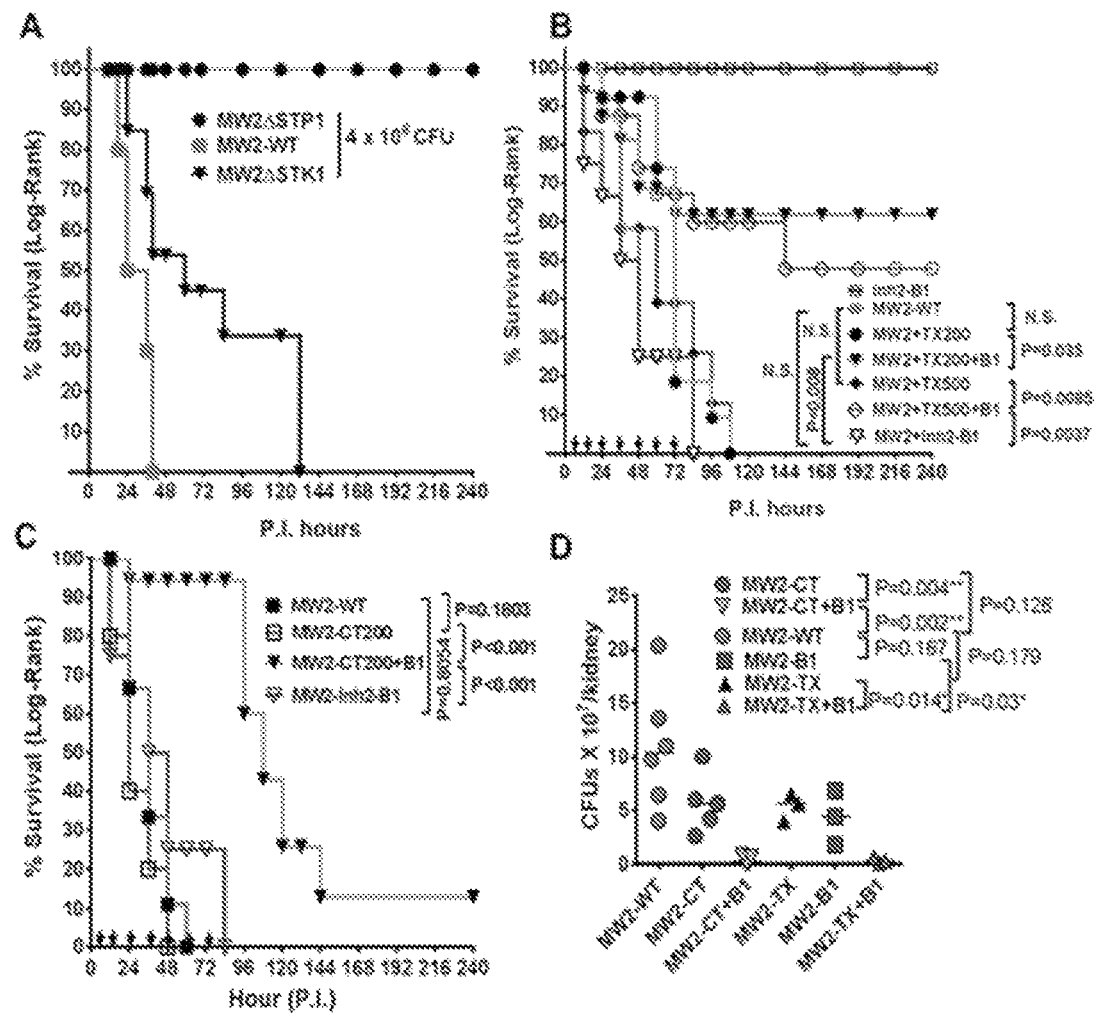
FIGS. 8A-D show Inh2-B1 enhances the in vivo bactericidal activity of Ceftriaxone and Cefotaxime in the *S. aureus* mouse septicemia model. (A) Effect of the deletion of the genes encoding STK1 and STP1 on the virulence of *S. aureus* MW2 strain in the mouse septicemia model. A group of 10 CD-1 female mice (~20 g) were challenged retro-orbitally with *S. aureus* MW2-WT wild-type. MW2ΔSTK1 or MW2ΔSTP1 mutant strains ($4.0 \times 10^8$ CFU/ 100 μl) and were observed for ten days for mortality and morbidity. (B) Effect of treatment with only Inh2-B1 (5 mg/kg body weight) or Ceftriaxone (10 and 25 mg/kg body weight i.e. 200 and 500 μg/mouse), and combination of Inh2-B1 (5 mg/kg, 100 μg/mouse) and Ceftriaxone (10 and 25 mg/kg, 200 and 500 μg/mouse) on mice challenged with a lethal dose ($4.0 \times 10^8$ CFU/100 μl) of the MW2-WT strain. (C) Effect of treatment with only Cefotaxime (10 mg kg/body weight, 200 μg/mouse), and combination of Inh2-B1 (5 mg/kg body weight, 100 μg/mouse) and Cefotaxime (10 mg/kg body weight, 200 μg/mouse) on mice challenged with a lethal dose ($4.0 \times 10^8$ CFU/100 μl) of the MW2-WT strain. Mice were treated every 12 h for four days as described in detail in the text (arrows on the X-axis) and were observed for ten days for morbidity and mortality. P values less than 0.05 were treated as significant and were determined by the Log-Rank test using GraphPad Prism 6 software. N.S. not significant. (D) Determination of colony forming units in kidneys of treated and untreated challenged mice. To obtain relative differential bacterial loads in different treated and untreated challenged groups, 3-6 mice were sacrificed on Day 3 P.I. The tissue extracts of kidneys were appropriately diluted, and CFU was counted on tryptic soy agar (TSA). Results were statistically analyzed based on the median values obtained from each group (WT, CT, TX, B1, CT+B1 and TX+B1) using t-test with Welch correction. P value less than 0.05 was treated as significant. WT—wild-type, CT—Cefotaxime, TX, Ceftriaxone, B1-Inh2-B1.

Mouse septicemia model was employed to evaluate STK1 as a therapeutic target and provide a proof of concept derived from the in vitro bactericidal assays described above that the STK1-inhibitor, Inh2-B1, can rejuvenate the bactericidal activity of Ceftriaxone and Cefotaxime in vivo. To determine the impact of the deletion of stk1 and stp1 genes on the pathogenicity of S. aureus, the CD-1 mice were challenged by inoculating bacterial suspensions of the corresponding mutant (MW2ΔSTK1 and MW2ΔSTP1), and the wild-type (MW2-WT) strains in the bloodstream of CD-1 mice via the periorbital venous plexus. Morbidity and mortality of the experimental animals were monitored twice daily for ten days. The untreated control mice challenged with the S. aureus MW2-WT strain died by 36 h post challenge (FIG. 8A). Mice that were challenged with the MW2ΔSTK1 mutant strain displayed a significantly delayed onset of acute infection when compared to infection with the wild-type MW2. However, all the challenged mice died by day 5 p.i. (FIG. 8A, MW2ΔSTK1 vs. MW2-WT, P=0.0037). On the other hand, all mice challenged with MW2ΔSTP1 survived indicating that the deletion of stp1 gene attenuates S. aureus virulence. Subsequently, a group of ten CD1 mice were treated intraperitoneally with compounds Inh2-B1 (5 mg/kg i.e. 100 μg/mouse), Ceftriaxone (10-25 mg/kg i.e. 200 and 500 μg/mouse), a combination of Inh2-B1 (5 mg/kg) and Ceftriaxone (10 and 25 mg/kg), or vehicle control at 12 h intervals. A total of nine doses were administered starting 4 h after the challenge with S. aureus MW2. The survival of challenged animals treated with therapeutic agents was recorded for ten days (FIG. 8B). The survival pattern of MW2-challenged mice that had received only Inh2-B1 or Ceftriaxone showed similar mortality patterns as was observed for mice that received no therapy (Inh2-B1 vs. untreated P<1.0. Ceftriaxone vs. untreated P<1.0). However, the MW2-challenged mice that received a combination therapy (Inh2-B1 5 mg/kg body weight, and Ceftriaxone 10 or 25 mg/kg body weight) showed significant (60%) survival (P<0.003). Increasing the dose of Ceftriaxone from 200 to 500 μg/mouse did not provide proportionately increased protection. Further, mice that were treated with only Inh2-B1 or only the vehicle survived all throughout the observation period and showed no morbid signs of illness, supporting the minimal to nontoxic nature of Inh2-B1 observed by the cell-line based in vitro toxicity/proliferation assays (FIG. 7).

To determine whether the Cefotaxime was as effective in vivo as Ceftriaxone, similar mouse protection studies were used as described above replacing Ceftriaxone with Cefotaxime using similar concentration (10 mg/kg body weight) in the presence and absence of Inh2-B1 (5 mg/kg body weight). The combination therapy (Inh2-B1+CT) significantly prolonged the survival of mice (P<0.001). The survival of the challenged mice in the absence of any therapy, or in the presence of only Cefotaxime remained the same, and all mice died within 36-48 hours unlike when the challenged mice were given a combined therapy (FIG. 8C). However, a number of survived animals at the end of 10 days were significantly low when the combined therapy included Cefotaxime instead of Ceftriaxone (FIGS. 8B and 8C). Irrespective of this survival pattern, the presence of S. aureus MW2 burden on day 3 P.I. was significantly low (P=0.002-0.014) in kidneys of mice, which received the combined therapy as compared to single therapy of Ceftriaxone, Cefotaxime, Inh2-B1, or no therapy (FIG. 8D).

Together, these results demonstrated that inhibition of the kinase activity of STK1 enhanced the bactericidal activity of Ceftriaxone and Cefotaxime. Inh2-B1, thus, can serve as an "antibiotic resistance breaker" and hence, can be used in a combination therapy to repurpose the so-called "failing" or "ineffective" cephalosporins against severe MRSA infection.

Discussion

The development of organism-specific, and target-based (with a defined mechanism of action) therapeutic agent over broad-spectrum agents is thought to represent a good strategy to cope with the emergence of selective drug-resistant species. Some of these strategies include those that target virulence, biofilm formation, and antibiotic resistance. It is disclosed herein that STK1 serves as a therapeutic target. It was clear that STK1, although plays a role in cell wall biosynthesis and the *S. aureus* mutant lacking STK1 becomes susceptible to the failing cell wall acting antibiotics and shows retarded growth, it is not an essential protein such as WalR for *S. aureus* survival. Hence, the development of a therapeutic agent against STK1 can be envisaged only in breaking the MRSA resistance against and enhancing or repurposing the "failing/ineffective" cell wall acting antibiotics. The STK1-inactivating compound, Inh2-B1, can serve as an "antibiotic resistance breaker." The quinazoline core structure of this compound has a precedent for many eukaryotic kinase inhibitors. Several amino-quinazoline-based inhibitors (Mitoxantrone, VI12112) have been described to inhibit the Ser/Thr kinase activity of mycobacterial PknB. However, this chemical inhibition did not result in growth inhibition even though the pknB gene is essential for growth. In addition to the quinazoline-type inhibitor, tetrahydro benzothiophene compound, AX20017 has also been identified that inhibits the activity of PknG, a nonPASTA-containing mycobacterial kinase that enables bacterial survival within human macrophage. This compound restores macrophage-mediated killing but does not inhibit the growth of extracellular bacteria. More recently, a sulfonamide-type STK1 inhibitor for *S. aureus* has also been identified that seems to enhance the in vitro activity of cell wall acting beta-lactam antibiotic, Nafcillin. However, its efficacy in enhancing the bactericidal activity of Nafcillin in vivo against a lethal challenge of *S. aureus* is presently unknown. In the present investigation, it is shown that a derivative of Inh2. Inh2-B1, specifically inhibits the kinase activity of *S. aureus* STK1. Inh2-B1 shows minimal to none cell-dependent toxicity to human cells and enhances the bactericidal activity of the failing Ceftriaxone/Cefotaxime antibiotic against highly drug-resistant and pathogenic *S. aureus* both in vitro bactericidal assays and in vivo experimental septicemia mouse infection model.

Figure 3:
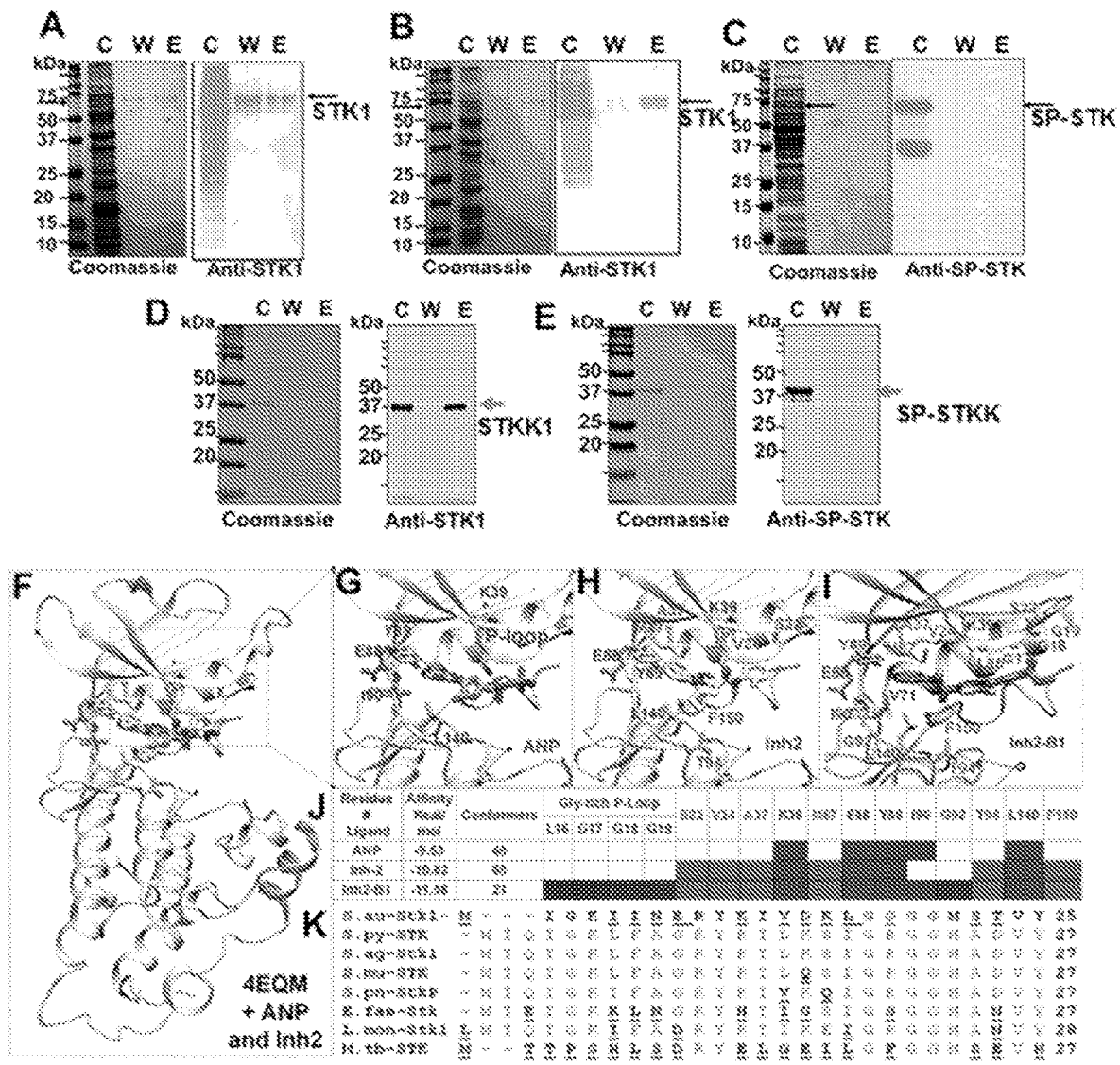
FIGS. 3A-K show binding of Inh2 and Inh2-B1 to the catalytic ATP-binding pocket of STK1. In vivo binding of (A) Inh2 and (B) Inh2-B1 to S. aureus STK1 as determined by ATP-column chromatography. Whole cell lysostaphin-digest of the MW2-wild type strain was passed on to the buffered equilibrated ATP-agarose column and eluted with 50 µM Inh2 or Inh2-B1 followed by detection of STK1 in Western Blot assay using the anti-STK1 polyclonal antibody as described in the Materials and Methods section. (C) A similar experiment showing whole cell lysate of the phage-lysin digested S. pyogenes M1T1 strain showing no elution of SP-STK. STK1 (~90 kDa) and SP-STK (~70 kDa) proteins (see pointed arrow) in their respective bacterial lysates are found with its degraded forms as described previously[20,36]. C-cell lysate, W-wash fraction, E-elution fraction. (D) Binding of the purified recombinant STKK1 to solid-phase ATP-column and its elution by Inh2-B1. (E) Binding of the purified recombinant SP-STK to solid-phase ATP-column and its elution by Inh2-B1. (F) In silico, molecular docking analysis-based the highest scored docked pose of ANP and Inh2 in the binding pocket of the kinase domain of S. aureus STK1 (PDB ID 4EQM). The protein is shown in the white cartoon. Interaction of (G) ANP (inactivated ATP shown in cyan), (H) small molecule compound Inh2 (shown in yellow) and (1) Inh2-B1 (shown in dark orange) and key residues (only the side-chain non-hydrogenous atoms) around 3.5 Å from the inhibitor are shown in the sticks. The coloring code of the atom type: C (Yellow or green in inhibitors and cyan in ANP), N (blue), and O (red). (J) A summary table is showing the association of ANP, Inh2, and Inh2-B1 with amino acid residues reflecting their affinity for the ATP-binding pocket and a number of conformers clustered in this region during molecular docking analysis. ANP constitutes key residues (blue fonts). The residues around Inh-2 are shown in red fonts and the residues around P-loop that directly interact with Inh2-B1 are shown in purple fonts (See also FIG. 55 for affinity and number of conformers for all Inh2 derivatives). (K) A comparison of the N-terminal sequence of STK1 with those of other Gram-positive pathogens showing the unique nature of the S. aureus STK1 P-loop (Red fonts). The underlined bold letters denote non-conserved amino acid residues.
Figure 17:
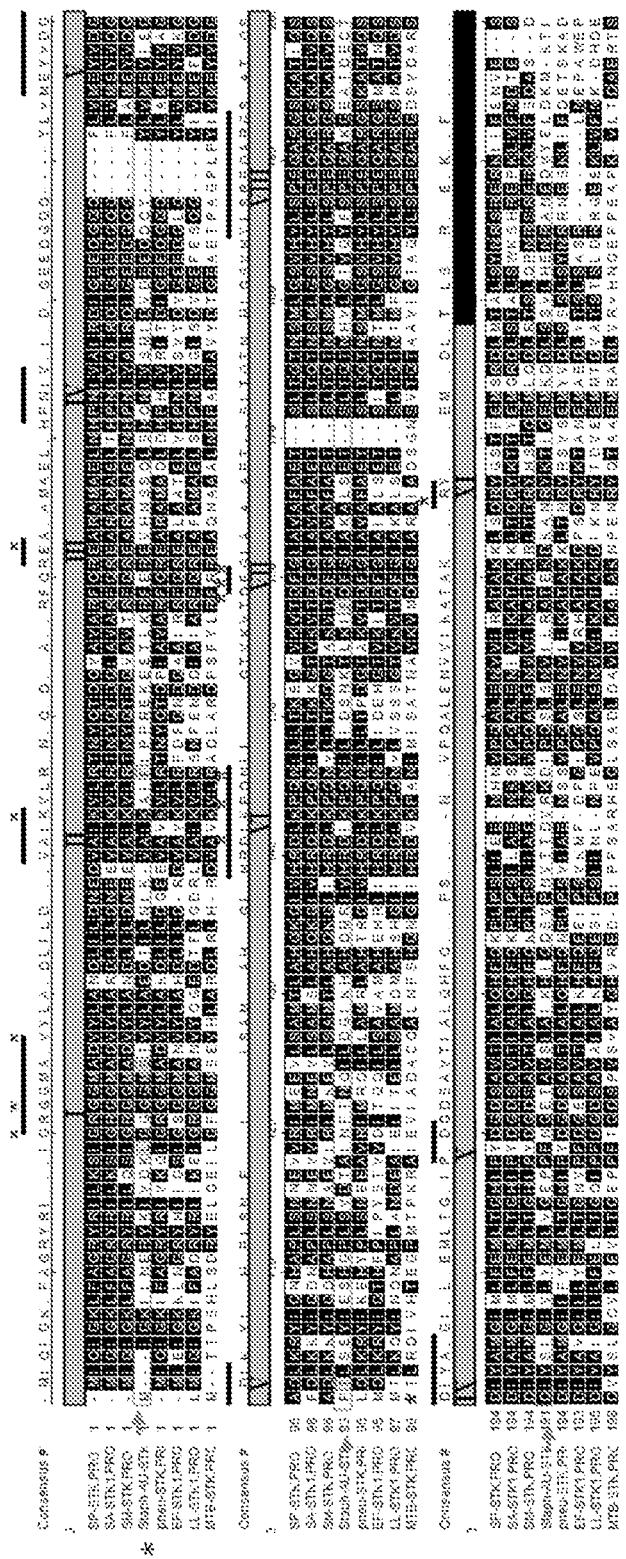
FIG. 17 shows a comparison of the amino acid sequence of the kinase domain of *S. aureus* STK1 with those of other gram-positive bacteria and *M. tuberculosis*. The boxed sequence (*) denotes *S. aureus* STKK1 (Staph-AU-Stk1). The STKK1 in the present study included 280 aa. The sequence in black denotes the conserved residues. Hank's motif (I-XI) region for catalytic kinase activity is shown above the sequence comparison. Note the P-loop $L^{16}G^{17}GGG^{20}$ in *S. aureus* STKK1 instead of a conserved GRGGMAD motif. $S^{22}$, $F^{37}$, $T^{94}$, and $F^{150}$ are the unique residues of the catalytic domain of *S. aureus* STKK1. Other Ser/Thr kinases shown in the comparison are from *S. pyogenes* (SP-STK), *S. agalactiae* (SA-STK1). *S. mutans*

The catalytic domain of the STKs of gram-positive pathogens is highly conserved. Crystal structures of the kinase domain of mycobacteria STK (PDB ID:-1MRU) and that of *S. aureus* STK1 (PDB ID:4EQM) suggest a conserved mechanism of activation for these kinases. However, Inh2-B1 did not inhibit the kinase activity of SP-STK of *S. pyogenes*. To understand this specificity, structure-based docking analysis was used to determine molecular interactions of Inh2 and Inh2-B1 within the catalytic domain using the crystal structures of *S. aureus* STK1 (PDB ID-4EQM). The amino acid sequence comparison of the kinase domain of Ser/Thr kinases of several Gram-positive pathogens has revealed a conserved ATP-binding site with a typical glycine-rich GRGG loop (FIG. 3). The role of this loop is implicated in stabilizing the phosphates of ATP, and hence also called the P-loop. Notably, the P-loop of *S. aureus* STK1 containing a unique tetra-glycine ($G^{17}GGG^{20}$) motif differs from those of STKs of other Gram-positive pathogens, which instead share the conserved G(R)GG motif (FIG. 3K). The inability of Inh2-B1 to inhibit the kinase activity of *S. pyogenes* SP-STK thus can be attributed to a different glycine-rich (GRGG) loop. Interestingly, Inh2-B1 but not ANP or Inh2 recognizes and interacts directly with the P-loop. Additional residues that are not recognized by inactivated ATP (ANP) or the lead molecule. Inh2, are L16 and G92. Additionally, among the six Inh2/Inh2-B1-interacting amino acid residues (S22, V24, A37, M87, T94, and F150; FIGS. 3H and 3I), four of them except V24 and M87 are unique to the *S. aureus* STK1 (see the amino acid residues highlighted in pink in FIG. 17). This unique sequence, as well as the P-loop, constituted by L16, 017-20 residues present in *S. aureus* STK1, may allow Inh2-B1 to attain a pose for a stronger and a stable interaction with the catalytic domain of STK1. A recent study has shown that the species-specific PASTA domain and associated free peptidoglycans somehow determine the specificity of the STK enzyme for its activation in response to external stimuli. The molecular docking analysis of Inh2-derivatives showing the highest affinity (−11.6 kCal/mol) of Inh2-B1 for the kinase domain of STK1 (PDB 4EQM) suggests that the tertiary structure (catalytic pocket) formed by the glycine-rich loop and the surrounding networks of amino acids contribute to the species-specific kinase activity.

Gram-positive bacteria employ eukaryote-type-Ser/Thr kinases (STKs) and phosphatases (STPs) to regulate fundamental biological processes. In *S. aureus*. STK1 controls bacterial virulence and plays a significant role in multidrug resistance traits. Mutations in the stp1 gene or the deletion of the stp1 gene result in increased drug resistance with no effect on growth. In this regard, the STP1 protein represents a poor candidate for a therapeutic target to control drug resistance problem despite the fact that *S. aureus* STP1 mutants are attenuated for virulence as also observed for MW2 in the present investigation (FIG. 8A). The substrates of STKs, in general, include both stand-alone and TCS regulators including WalR as recently reported for *S. pyogenes* and *B. subtilis*. Several important cell wall hydrolase genes, such as lytM, atlA, ssaA, have been reported to be down-regulated in *S. aureus* Stk1 mutant as has also been reported in conditional walR mutant of *S. aureus*. Here, it is shown that the expression of cell wall hydrolase genes is reduced in mutants lacking STK1 as well as in the Inh2-B1-treated MW2-WT. The reciprocally regulated expression of some of these genes in mutants lacking STP1 as compared to the isogenic mutant lacking STK1 derived from MW2 strain suggests that the *S. aureus* STK1 can also phosphorylate WalR in vivo as in vitro. The results showing reversible phosphorylation of *S. aureus* WalR by STK1 and STP1, and WalR binding to the promoter regions of certain genes support this notion and a possible mechanism of STK1-mediated regulation of staphylococcal cell wall hydrolases and mechanism underlying the "antibiotic-resistance-breaker" property of Inh2-B1.

Figure 4:
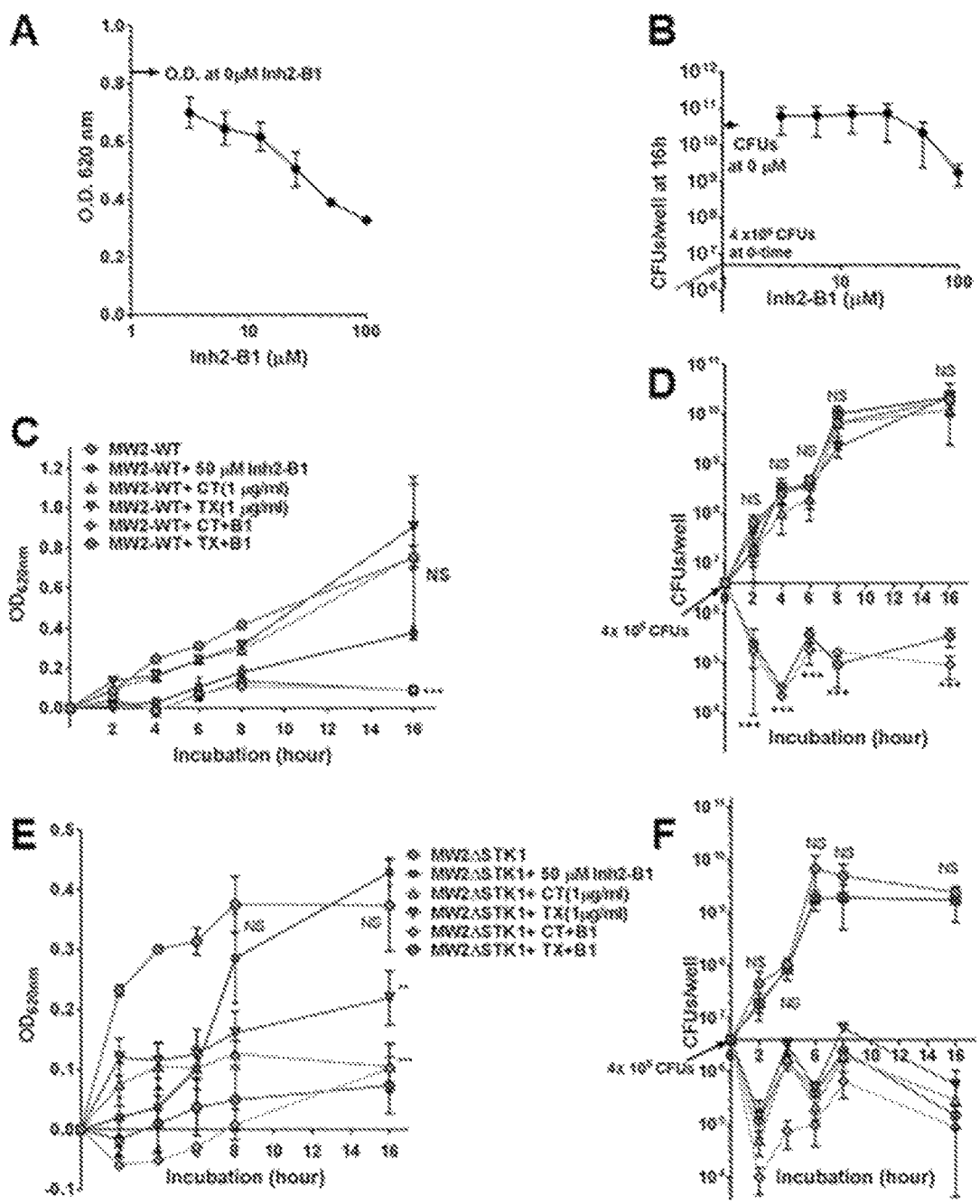
FIGS. 4A-F show. Effects of Inh2-B1 enhances the bactericidal activity of Ceftriaxone and Cefotaxime. Time-to-kill experiment shows Optical Density (OD) at 620 nm and viable bacterial counts (colony forming units) of (A and B) MW2-WT at different time intervals, when grown in the presence and absence of Inh2-B1 inhibitor. Optical Density and corresponding Colony forming units of (C and D) MW2-WT and (E and F) MW2ΔSTK1 cultures in the presence or absence 50 µM Inh2-B1, 1.51 µM (1 µg/ml) Ceftriaxone, 2.125 µM (1 µg/ml) Cefotaxime, and combination of Inh2-B1 plus Ceftriaxone, and Inh2-B1 plus Cefotaxime. The experiments were carried out as described in the Materials and Method section using Muller-Hinton broth and seeded with 4×10$^6$ CFUs of S. aureus MW2-Wild type or MW2ΔSTK1 strains per well. Each data points represent Mean±S.D. P values of significance (=<0.01, *=<0.001) were determined using the t-test with Welch's corrections. NS—Not significant.

The process of antibiotic resistance, biofilm formation, and cell wall biosynthesis are interrelated. The ability of Inh2-B1 to inhibit cell wall hydrolases as shown in the MW2ΔSTK1 mutant, and also the biofilm formation supports that inhibition of the expression of WalR-dependent genes encoding cell wall hydrolases was found to be directly associated with the *S. aureus* ability to form biofilms. The formation of biofilms results in decreased accessibility of antibiotics, which in turn promote the emergence of the drug-resistant population. The Inh2-mediated down-regulation of genes that encode cell wall hydrolases may relax peptidoglycan crosslinking and in turn, may facilitate penetration of other antibiotics or restore susceptibility to wall-acting antibiotics (FIG. 4). The fact that highly drug-resistant MW2ΔSTP1 mutant also became susceptible to Ceftriaxone and showed decreased biofilm formation suggests that the increased ability to form robust biofilms may serve as an additional factor that contributes to less penetration of effective antibiotics and increased drug resistance. In this regard, the present approach not only helps in enhancing bactericidal activity of the failing antibiotics but also serves as an anti-biofilm agent. Inh2-B1 in this context serves as a double-edged sword-"antibiotic resistant breaker." One of the concerns that whether a potential combined therapy can fail if some mutation occurs in the STK1 encoding gene or indirectly through other hitherto unknown pathways. It is noteworthy that while mutations in the stp1 gene of clinical isolates of S. aureus have frequently been observed but not in the conserved kinase domain of the stk1 gene. In fact, the stk1 gene in all S. aureus genomes is completely conserved.

In summary, disclosed herein is the first comprehensive report on the identification STK1-specific and therapeutically relevant compound that can serve as an antibiotic resistant breaker and anti-biofilm agent. The compounds Inh2-B1 serves as an antibiotic resistance breaker by essentially inhibiting the kinase activity of S. aureus STK1 that contributes significantly to antibiotic drug resistance via modulating the function of cell wall biosynthesis machinery. Thus, its action is effectively perceived in combination therapy with certain cephalosporins that are deemed to be ineffective. Inh2-B1 poses minimal risks regarding cytotoxic or apoptotic activities on human cells. The latter property is essential since many kinase inhibitors have been successfully used based on their ability to cause apoptosis of human cells for tumor therapy. The inability of Inh2-B1 to cause no apparent toxic effects in experimental animals or minimal toxicity to normal or tumor cells, and ability to remain stable in the serum and body fluid, such as peritoneal fluid, are important initial safety features of this agent. The present findings thus clearly demonstrate the specificity of Inh2-B1 for S. aureus STK1 and support the future endeavors to develop an effective combination therapy with various ineffective cephalosporins and other cell wall acting antibiotics to repurpose them therapeutically and economically more effective against severe multidrug-resistant MRSA infections.

Materials and Methods

Bacterial Strain, Media, and Cell Lines.

S. aureus strains MW2, a highly pathogenic and a multidrug-resistant strain was obtained from Network on Antimicrobial Resistance in Staphylococcus aureus (NARSA). Streptococcus pyogenes M1T15448 was obtained as described previously. Staphylococcus strain was grown in tryptic soy broth (TSB) or TS agar. Streptococcus strain was grown in Todd-Hewitt broth supplemented with 0.5% yeast extract or 5% sheep-blood TS agar. Escherichia coli strain (DH5α, BL21 DE3-pLysS) were grown in Luria-Bertani (LB) or LB agar with or without ampicillin (100 µg/ml). All bacterial culture media were obtained from Difco (BD and Co, Sparks, Md.). Antibiotics unless otherwise indicated were used at the following concentrations: 100 g/ml of ampicillin and 10 µg/ml of chloramphenicol for E. coli, 10 µg/ml of erythromycin and 10 µg/ml of chloramphenicol and 1.5 µg/ml of anhydrotetracycline for S. aureus. Human pharyngeal carcinoma cell line (Detroit 562, CCL-138ATCC), and BEAS-2B (normal lung/bronchoalveolar immortalized cell lines, CRL-9609, ATCC), were grown in 24 well plates to obtain a confluent culture. Detroit 562 cell lines were grown in RPMI 1640-GlutaMax-1 (GIBCO) tissue culture medium with 10% fetal bovine serum. BEAS-2B cell lines were grown in a serum-free medium, LHC-9, supplemented with epidermal growth factor and pituitary extract.

Recombinant STKK1 and In Vitro Kinase Assays.

For the present study, recombinant His-tag-STKK1 was created along with part of the adjacent juxta-membrane domain (1-280 aa) using the pET14b vector system and specific primers (Table-1 and Table-2) as described previously. The recombinant proteins were expressed in BL21 DE3 (pLysS) and purified using $Ni^{+2}$-NTA-affinity chromatography, dialyzed against 10 mM Tris/HCl, pH 7.5, and stored as 10% glycerol stock (500 µg/ml) at −20° C. as described previously. In vitro kinase assays were performed using 2 µg STKK1 in the presence of 1 µCi $\gamma^{32}$P-ATP (specific activity 3000 Ci/mMol, PerkinElmer) at 30° C. for 45 min in a final volume of 30 µl phosphorylation buffer (50 mM Tris/HCl, pH7.5, 1 mM dithiothreitol, 5 mM $MgCl_2$, and/or 5 mM $MnCl_2$). The inhibition of autophosphorylation of STKK1 was carried out using this assay in the presence and absence of (50 µM) individual members of the 32 prescreened small molecule compound library. Phosphorylated proteins were separated by SDS-PAGE and subsequently identified by using Coomassie stain and autoradiography. The individual phosphorylated protein bands were then excised and subjected to radioactive counting using beta-scintillation counter for quantitative analysis. Experiments were repeated at least three times for statistical analysis. Compounds that showed more than 80% inhibition of the kinase activity was then further titrated (concentration range <1-150 µM) to determine its $IC_{50}$ concentration for S. aureus STKK1 after preincubated for 5 min.

Construction of Δstk1 and Δstp1 Mutants.

S. aureus MW2 mutants lacking stk1 or stp1 were created as described previously essentially using pMADΔstk1chl and pKOR1Δstp1 vectors that were originally used to derive similar mutants from S. aureus N315 strain (Table 1). Briefly, each plasmid construct was passed through S. aureus RN4220 strain before transformation into electrocompetent MW2. The Δstk1 mutant was selected on TSA containing chloramphenicol (10 µg/ml). The Δstp1 mutant was selected on TSA containing anhydrotetracycline followed by TSA and TSA with chloramphenicol.

Chloramphenicol-sensitive transformants were confirmed on TSA plates with repeated passage to obtain the markerless Δstp1 mutant. The genetic integrity of mutants was confirmed by PCR and DNA sequencing using appropriate primers. Growth curves of each mutant and the wild-type parent strain were measured in sterile 96-well microtiter plates using 1:250 diluted seed inoculum from the late log-phase culture. In addition to TSB, chemically defined medium (Teknova, Hollister, Calif. cat #4751) supplemented with 1% (w/v) glucose, maltose, lactose, or galactose was used to determine the impact on metabolic fitness. Growth curves were measured using PolarStar Galaxy spectrofluorimeter (BMG), which was preprogrammed to monitor changes in absorbance of the culture at 620 nm every min at 37° C. for 16 h with horizontal shaking for 10 seconds before measuring the reading. The growth curve for each strain was then plotted using GraphPad Prism 6.

Transmission Electron Microscopy (TEM):

TEM of the S. aureus strains was performed after fixing the late log-phase grown bacterial cells with 2.5% glutaraldehyde and 4% paraformaldehyde.

Quantitative Real-Time PCR.

The late log phase-grown *S. aureus* strains MW2 wild-type, and isogenic ΔSTK1 and ΔSTP1 mutant strains, as well as *S. aureus* MW2 strain treated with 25 µM Inh2-B1 for 4 h, were subjected to lysostaphin treatment to obtain whole cell lysate. Total RNA from the resulting lysate was first extracted by TRIZOL™ (Invitrogen/Thermo) and treated with RNase-free DNaseI. High-quality total RNA (RIN>7.0, and 260/280 and 260/230 ratios >1.8) was then extracted by using RNA purification kit (Norgen, Canada) per manufacturer's instructions and confirmed by an Agilent 2100 Bioanalyzer (Agilent Technologies, Palo Alto, Calif.). The first-strand cDNA from the total RNA was generated, and relative mRNA concentration was quantitated using SYBR Green qRT-PCR master mix and specific primers, using a Light Cycler® 480 real-time PCR machine (Table 2). The results obtained for all samples (three biological replicates each in triplicates) were normalized to corresponding values of 16S rRNA. All results including relative fold-changes in the mRNA expression (mutant vs. wild-type or treated vs. nontreated) for individual genes were analyzed using Exor4 software (Roche Applied Science). Changes in expression ratios by more than 2-fold (up- or down-regulation) were considered as significant.

Electrophoretic Mobility Shift Assays (EMSA).

EMSA experiments were performed using end-labeled ~250-300-bp (encompassing the promoter element upstream of four cell wall hydrolase-encoding genes SA0710. SA0905, SA2097, and SA2353. These probes were PCR-amplified using specific primers (Table 2). Briefly, the binding reaction was performed in 35 µl reaction mixture containing labeled probe (20,000 cpm/ml) with purified 1-3 nM purified WalR in EMSA buffer (2 mg/ml poly dI-dC (Sigma), 10 mM Tris pH 7.5, 35 mM KCl, 1 mM EDTA pH 7.5, 1 mM DTT, 6% glycerol and 1 mM $MgCl_2$). Phosphorylated and non-phosphorylated WalR were first incubated with poly dI-dC containing reaction buffer for 5 min at room temperature. The probe DNA was added, and the reaction mixture was incubated at 37° C. for 25 min. WalR-bound and free probe in the reaction mixtures were resolved by 4.5% non-denaturing polyacrylamide gel electrophoresis (200V×30 min) using 0.5×TBE buffer and visualized by autoradiography. To establish the specificity of the STKK~P-phosphorylated WalR in binding to DNA, the autophosphorylated STKK~P was incubated with the $^{32}$P-labeled promoter probe as a control. Similarly, the 100-fold Cold-probe was mixed with the labeled probe in the EMSA to determine the specificity of WalR binding to its promoter. The band intensities were quantitated using AlphaInnotech ImageQuant densitometric software. The ratio of the concentration of nonphosphorylated WalR versus phosphorylated WalR required to achieve 50% of the maximum binding of phosphorylated WalR to different promoter probes was determined based on two separate experiments by GraphPad prism-6. These results were used to determine the relative binding efficiency of STKK-phosphorylated WalR to various promoters.

Small Molecule Compounds.

32 compounds were picked that inhibited the growth of *S. aureus* RN4220 in the final concentration of ~40-60 µM range from the original small molecule library of 167.405 compounds. This library was tested at the National Screening Laboratory for Regional Center of Excellence for Biodefense and Emerging Infectious Disease (NSRB) at the Harvard Medical School (Boston, Mass.). This prescreened NSRB library was the starting point of present investigation. Among these 32 compounds (serial number from Inh to Inh32), Inh-2 (N-(2,4-Dimethylphenyl)-5-oxo-1-thioxo-4,5-dihydro-[1,3] thiazolo [3,4-α] quinazoline-3-carboxamide) (initial screen hit 1391-A20) was identified as one of the three molecules that showed dose-dependent STK1 inhibition with lowest $IC_{50}$ (San Diego, Calif.). Using this compound as the lead molecule, nine other compounds, each representing with modified side chain(s), were designed using the online ZINC software for the validation of biological properties of STK1 inhibition. These compounds were custom synthesized (mCule Co., San Diego, Calif.) (FIG. 13) at >95% purity and were initially stocked at 25 mM concentration in DMSO and stored at −80° C. Subsequent dilution to the desired concentration was carried out in 50 mM Tris/HCl buffer in a pH range of 7.5-8.8. At this pH range, all molecules were found to be completely soluble yielding no visible pellet upon centrifugation (16,000×g for 2 min).

In Vivo Binding of the Inhibitor to *S. aureus* STK1.

An overnight culture of *S. aureus* MW2 strain was centrifuged, and the resulting bacterial pellet was resuspended in lysostaphin digestion buffer (50 mM Tris/HCl buffer, pH 7.5, containing 5 µg/ml DNAse/RNAse and protease inhibitor cocktail) in ⅒ the volume of the original culture volume. The latter was then subjected to lysostaphin treatment (15 U/ml). The lysostaphin digest was sonicated (5 sec pulse at every 10 sec for 10 min at 50% of 130 W, 20 Kz amplitude), and the debris free whole cell lysate was obtained after centrifugation (10.000×g, 10 min, 4° C.). The lysate was then equilibrated with binding buffer (10 mM Tris/HCl pH 8.0 and 150 mM NaCl) and passed through the solid phase-ATP-Separopore® 4B-CL column (BioWorld) pre-equilibrated with the binding buffer. The column was then washed with ten column volumes of binding buffer. Subsequently, the bound proteins were eluted with the 10-column volume of buffer containing 50 µM Inh-2 and Inh2-B1. *S. aureus* crude lysate, the last fraction of the column washing step, and eluted fractions were resolved by SDS-PAGE and electroblotted onto a PVDF membrane. The latter was probed with affinity purified rabbit anti-STK1 (IgG) (12) to determine the presence of STK1 eluted from the bound proteins from the crude lysate by the inhibitor in chemiluminescence-based Western Blot analysis. A similar experiment was performed using *S. pyogenes* whole cell lysates obtained from phage lysin-digested *S. pyogenes* M1T1 strain using the anti-SP-STK antibody as described previously using to determine the specificity of the inhibitor for *S. aureus* STK1.

In Silico Determination of the Binding of Inh2-Derivatives to STK1 by Molecular Docking.

To determine the interactive environment within the ATP-binding catalytic domain of STK1 for individual Inh2 derivatives, in silico molecular docking analysis was carried out employing Autodoc 4.0 software. To prepare the ligand, the program mol2chemfig (http://www.jcheminf.com/content/4/1/24), and a web server NCI/CADD (http://cactus.nci.nih.gov/translate) were used to generate the structure from SMILE. Furthermore, the structure of the compound was drawn with ACD Chem Sketch 11.0 (http://www.acdlabs.com/resources/freeware/chemsketch). Subsequently, its molecular geometry was optimized at the B3LYP/6-31G (d,p) level up to a convergence in the energy of $10^{-5}$ AU using the Gaussian03 package. The crystal structure 4EQM (chain A) of *S. aureus* STK1 kinase domain was used for docking of the compounds after removing all the heteroatoms and crystal waters.

The AutoDock 4.0 was used to conduct blind docking to identify the most likely binding site of the compound.

AutoGrid 4.0 was employed to build a 126×71×71 grid map covering the kinase domain with a spacing of 0.675 Å. The Lamarckian Genetic Algorithm was used for conformational sampling of the compound. For each docking simulation, 200 runs were carried out with 300 random individuals in the first population with $2.5\times10^7$ energy evaluations and the $2.7\times10^7$ number of generations. For the local search, the so-called pseudo-Solis and Wets algorithms were applied using the default parameter. From each docking run, the lowest-energy conformations of the compound were chosen for clustering with an RMSD cutoff of 2 Å. The conformations of the compound were then ranked and clustered based on their energy scores and populations.

Subsequently, for targeted or focused docking, grids with dimensions 50×50×50 and a spacing of 0.375 Å were focused on the biggest cluster that was obtained from the blind docking to get the most probable binding pose of the compound. Here, parameters of $2.5\times10^6$ energy evaluations and the $2.7\times10^6$ number of generations were applied. However, rest of the docking settings were kept similar to the blind docking step. The final conformations of the compound were ranked and clustered by energy and population scores. The VMD (Visual Molecular Dynamics) 1.9.1 was used for analysis and image preparation.

MIC and MBC Determination.

Growth inhibition of *S. aureus* strains (MW2-WT, MW2ΔSTK1 and/or MW2ΔSTP1) in the presence of Ceftriaxone (TX), Cefotaxime (CT), Ciprofloxacin (CI), Clindamycin (CM), Erythromycin (ER). Meropenem (MP), Ofloxacin (OF) and Tetracycline (TC) was initially determined using the E-Test method (AB BIODISK North America Inc., Piscataway, N.J.) on Muller-Hinton agar plates as described previously in the absence or the presence of 50 μM Inh2-B1. Subsequently, the susceptibility of *S. aureus* MW2 strain to Ceftriaxone, Cefotaxime, Inh2, and Inh2-B1 was confirmed by the CLSI recommended serial dilution method using Muller Hinton broth. Minimum bactericidal activity (MBC) was measured using Muller-Hinton agar. Changes in the MBC of Ceftriaxone/Cefotaxime in the presence of serially diluted Inh2-B1 was determined in two steps. Initial screening was carried out using the Checkerboard method using Muller-Hinton agar (FIG. 15). The MBC was identified by determining the lowest concentration of antibacterial agent that displayed a reduction in the viability of the initial bacterial inoculum by ≥99.9% (absence of any colony forming unit). Subsequent time to kill assays were carried out using 50 μM Inh2-B1 and Ceftriaxone. Cefotaxime (1 μg/ml) in a final volume of 250 μl using a sterile 96-well (U-bottom) microtiter plate over a period of 16 h at 37° C. under constant rotation (120 rpm). Optical density and corresponding CFU counts were measured at every two-hour interval up to 8 hours with a final overnight reading at the end of incubation period. CFU counts were measured using appropriate dilution of 10 μl of properly mixed samples at each time interval. All experiments were performed in three biological replicates and the statistical analysis of the results obtained at each time point was carried out by the non-parametric t-test with Welch's correction using GraphPad Prism 6 software.

Cytotoxicity.

Various concentrations (1.56-100 μM) of the small molecule compounds Inh2-B1 were tested for their cytotoxicity by incubating them for 24 h in the cell lines mentioned above. The cytotoxicity of compounds was determined by measuring the activity of lactate dehydrogenase (LDH) released from the damaged cells during incubation. The LDH assay was performed in triplicate wells. At the end of incubation, the plates were lightly centrifuged, and the culture supernatants were examined for the presence of LDH activity using Cytotoxicity Detection Kit (Promega) per the manufacturer's instructions. LDH activity was detected spectrophotometrically (Molecular device, 490 nm) and normalized to the total LDH activity (100%) in cell lysate of the untreated cells. Background value obtained with untreated culture supernatant was subtracted before data evaluation.

MTT-Assay:

Impact of Inh2-B1 on cell proliferation was determined by MTT (3-[4,5-dimethylthiazol-2-yl]-2,5 diphenyl tetrazolium bromide)-based assay using Roche Colorimetric proliferation assay kit. Cell lines mentioned above were grown in 96-well tissue culture plates in the $CO_2$ incubator at 37° C. The cells were treated with Inh2-B1 as described above in a final volume of 100 μl for 24 h. At the end of incubation, tissue culture medium from each well was removed and replaced with fresh 100 μl of the medium containing MTT solution (0.5 mg/ml) and further incubated for 4 h. The purple color of formazan salt crystals formed in each well was solubilized with the addition of 100 μl of 10% SDS solution in 0.01M HCl and further incubating for 10-12 h. The solubilized formazan product in each well was spectrophotometrically analyzed using a microtiter plate reader (Molecular Devices, 570 nm). Absorbance values of wells containing MTT reagents without cells and the untreated cultured cells with MTT reagents were considered as the background and negative controls. All tests were performed in triplicate wells. The average background value obtained from 10 wells was subtracted from the test values, and the corrected values obtained from untreated and treated cells were statistically analyzed by Student's test. $P<0.05$ was treated as a significant difference.

Biofilm Formation:

The ability to form biofilms by *S. aureus* MW2 strain in the absence and presence of Inh2-B1 was determined using the crystal violet stain method. Briefly, the assay was carried out in 24-well tissue culture plates in a final volume of 500 μl of TSB broth with or without Inh2-B1 (25 μM). The culture plates were then seeded with 1:1000 dilution of the freshly grown *S. aureus* cultures to late log phase ($O.D_{600}=0.8$) and further incubated for 48 h. At the end of incubation, the culture medium from each well was carefully removed and stained with 1% Crystal violet for 5 min. The unbound stain was then removed by repeated washings with distilled water and air dried. The stained biofilms were then extracted and dissolved in 500 μl 100% of isopropanol. Aliquots of fully suspended biofilms (100 μl/well) in isopropanol from each well were spectrophotometrically ($\lambda=550$ nm) analyzed using a microtiter plate reader (Molecular Devices). The test samples were analyzed after subtracting the background values obtained from wells containing an only medium. All results were obtained with three independent cultures each in three wells. In another set of experiments. Inh2-B1 (25 μM) was added to the 48 h-grown established biofilms of *S. aureus* MW2 to determine the impact of Inh2-B1 on the preformed biofilms and its ability to disrupt or further formation of biofilms. For this, old medium was carefully removed to allow the minimal loss of the loosely attached apical part of the preformed biofilms and replace with 2 ml of fresh TSB medium with or without 25 μM Inh2-B1 inhibitor and incubated further for 48 h at 37° C. Subsequently, the biofilm formation or its disruption was quantitatively estimated as described above and statistically evaluated.

Ethical Statement:

The animal studies described herein were carried out in strict accordance with the recommendations in the Guide for the Care and Use of Laboratory Animals of the National Institutes of Health and the NC3R[S] recommended ARRIVE (Animal Research: Reporting of In Vivo Experiments) guidelines (https://www.nc3rs.org.uk/arrive-guidelines). All animal experiments, anesthesia procedures, and early removal criteria were observed and performed per the protocol (#2007A0134-R3) approved by the Ohio State University Institutional Animal Care and Use Committee (IACUC).

Animal Experiments.

The virulence potential of the wild-type S. aureus MW2 wild-type and corresponding MW2ΔSTK1 and MW2ΔSTP1 mutants was assessed using the mouse-septicemia model. CD-1 mice (5 weeks old, 20-22 g. Charles River Laboratories, ten female mice/group and housed in a group of 5 mice/cage) were lightly anesthetized with isoflurane and injected retro-orbitally with the S. aureus MW2 or isogenic MW2Δstk1 mutant (4×10$^8$ CFU/0.1 ml of PBS). Infected, as well as sham-infected animals, were observed for 10 days for survival/mortality and morbidity. For therapeutic studies, the animals were first challenged with MW2-WT strain as described above and subsequently administered with antibiotic and/or small molecule compounds. The latter was started 4 h after the challenge and subsequently 12 h apart for 4 days post infection. Thus, Inh2-B1 (5 mg/kg body weight in 0.3 ml vehicle buffer), Ceftriaxone (10 and 25 mg/kg body weight in 0.3 ml vehicle buffer). Cefotaxime (10 mg/kg body weight), combination of Ceftriaxone (10 mg and 25 mg/kg body weight in 0.3 ml vehicle buffer) or Cefotaxime (10 mg/kg body weight) with Inh2-B1 (5 mg/kg body weight in 0.3 ml vehicle buffer), or 0.3 ml of vehicle-buffer (50 mM Tris/HCl, pH 8.8, 1.67% [v/v] DMSO). Early removal and euthanasia criteria were applied to all experimental mice showing penultimate sign(s) of the unrecoverable stage of illness, including ruffled skin with a hunch back, loss of more than 20% of body mass as compared to unchallenged mice receiving mock treatment, dyspnea, and labored gasping. All experiments were performed twice. Data were combined, and percentage survival in each group was statistically evaluated by the Log-Rank test (Kaplan-Meier) using the GraphPad Prism 6 software. P<0.05 was treated as a significant difference. On Day 3 P.I., 3-6 mice from different groups receiving treatment with a single antibiotic or combination therapy were euthanized and sacrificed, and kidneys were sacrificed for determining the bacterial load, which was determined by counting the colony forming units in the homogenized tissue in sterile PBS buffer. Statistical analysis of these results was performed based on the median CFU counts and by employing the non-parametric t-test with Welch's correction.

TABLE 1

Strains and plasmids used

| S. No. | Plasmids | Purpose of the study | Reference |
|---|---|---|---|
| 1 | pET14b | E. coli expression vector (amp$^R$) with N-terminal histidine tag | Novagen |
| 2 | pET14B-STP1 | pET14B plasmid with entire SA1062 gene inserted between NdeI and BamHI | 1 |
| 3 | pET14B-STKK1 | pET14B plasmid with kinase domain of SA1063 gene inserted between Nde and BamH1 | This study |
| 4 | pET14B-WalR | pET14B plasmid with kinase domain of SA0017 gene inserted between XhoI and BamH1 | This study |
| 5 | pMADΔSTK1chl | pMAD containing up- and downstream regions of SA1063 (stk1)flanking chI | 1, 2 |
| 6 | pKOR1ΔSTP1 | pKOR1 containing up- and downstream regions of SA1062(stp1) | 1, 3 |
| 7 | PET14B-SP-STKK | pET14B plasmid with kinase domain of the SP-STP (SPy_1625, SP-STKK) encoding gene of Streptococcus pyogenes M1SF370 inserted between NdeI and BamH1 followed by HpaI and BAmH1 digestion and blunt end religation | 4 |

| S. No. | Strains | Purpose of the study | Reference/ Source |
|---|---|---|---|
| 1 | DH5α | E. coli: F- φ80lacZΔM15 Δ(lacZYA-argF) U169 recA1endA1 hsdR17(rK-, mK+) phoA supE44 λ- thi-1 gyrA96 relA1: used for cloning | Invitrogen |
| 2 | BL21(DE3)pLysS | E. coli: F ompT hsdS$_B$ (r$_B^-$ m$_B^-$) gal dcm(DE3)pLysS (Cam$^r$) for heterologous protein expression | Invitrogen |
| 3 | RN4220 | Restriction-deficient derivative of NCTC 8325-4 | NARSA |
| 4 | S. aureus MW2 (BK9897) | Community-associated Methicillin-resistant S. aureus parent strain | NARSA |
| 5 | MW2ΔSTP1 | MW2 lacking SA1062 | This study |
| 6 | MW2ΔSTK1 | MW2 lacking SA1063 | This study |
| 7 | Streptococcus pyogenes M1T1 5448 | For screening Inh-2-screening small molecule Inhibitors under study, In vivo binding of SP-STK | 4 |

REFERENCES FOR TABLE 1

1. Beltramini A M, Mukhopadhyay C D, Pancholi V. "Modulation of cell wall structure and antimicrobial susceptibility by a Staphylococcus aureus eukaryotic-like serine/threonine kinase and phosphatase." Infect Immun. Vol. 77, no. 4. (April 2009.): 1406-1416.

2. Arnaud, M., A. Chastanet, and M. Debarbouille. 2004. New vector for efficient allelic replacement in naturally nontransformable, low-GC-content, gram-positive bacteria. Appl. Environ. Microbiol. 70:6887-6891.
3. Bae, T., and O. Schneewind. 2006. Allelic replacement in *Staphylococcus aureus* with inducible counter-selection. Plasmid 55:58-63.
4. Jin, H, and Pancholi, V. 2006. Identification and biochemical characterization of a eukaryotic-type serine/threonine kinase and its cognate phosphatase in *Streptococcus pyogenes*: Their biological functions and substrate identification. J. Mol. Biol. 357:1351-1372.

described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a

TABLE 2

Primer sequences used for construction of recombinant proteins, qRT-PCR analysis and probe amplification for EMSA. The open reading frame (ORF) numbers are based on the genome sequence data of *S. aureus* N315 strain. Restriction sites are in underlined Primers used for the construction of recombinant proteins

| ORF | Name | Forward (5'-3') | Reverse (5'-3') |
| --- | --- | --- | --- |
| SA1063 | STKK | CTACGGCCATATGATAGGTAAAATAATAAATGAACG | CGCGGGATCCTTAGACATCTTCATTCGC |
| SA1062 | STP | CTACGGCCATATGCTAGAGGCACAATTTTTTACTGATACTGGAC | CCGCGGATCCTCATACTTTATCACCTTCAATAGCCG |
| SA0017 | WalR | AAACTCGAGATGCAAATGGCTAGAAAAGTT | TTTGGATCCCTACTCATGTTGTTGGAGGAA |

Primer for Real Time PCR

| ORF | Gene | Forward (5'-3') | Reverse (5'-3') |
| --- | --- | --- | --- |
| SA0017 | walR/vicR | TGGAAGTATGTCGTGAAG | GTGCTGGTTGTGAGTAAT |
| SA0265 | lytM | TAGGTCCAGACGCGAGCTAT | CGTCTTTCGCATGACCACTA |
| SA0270 | ssa-like | TCGGTATTGCTGGTGTCAAA | CAACACGCCAAACAACAATC |
| SA0423 | sle1 | CGAACTCAGGATCTGCAACA | CGCTGCGTTATCCCAGTTAT |
| SA0620 | ssaA homologue | CCACCTGATCCACCATTAGG | GCTGGTTCAGCATCATCTCA |
| SA0710 | lytE | CACAACAACATGGCACACAA | TGAAATCACGTCACCAGGAA |
| SA0905 | atlA | AATGGTTGCATTAACGCTTGT | TTGCTGTTTTTGGTTGGACA |
| SA1090 | lytN | TGGGTATGTCGAACAAAGCA | TTTCCGTTTGAAATTGCTGA |
| SA1898 | sceD | AGGAAATGCAGGTCACGAAG | TTAGTTGCAGGTGCTTGTGC |
| SA2093 | ssaA | AATGGCCGTTCAATCTCAAG | ACGTATGCAACGTGACCGTA |
| SA2097 | ssaA | AGGTCAAGCACATCATGCAG | ACCGATTTCTCCGCCTACTT |
| SA2353 | ssaA1 | TAACCACACCAGCACCATGT | TGTTGGTGGGAAAATTGGTT |
| SA2356 | isaA | CTGCAGGTGCTACTGGTTCA | ACAGCTGCGTTGATTTGTTG |
| SArRNA01 | 16S | GTTATCCGGAATTATTGGGCG | CCGGGCTTTCACATCAGACT |

Primers for probe amplification for EMSA

| Name | Forward (5'-3') | Reverse (5'-3') |
| --- | --- | --- |
| PSA0710 | AGTACAATTCGGTAGATAGAGTTAG | CTTGCTGTCATTCCTTTGCTGTTAG |
| PSA0905 | AGTTGTATCTATTTTAGAAACATTTGT | TTCTATTTATTACTCCTAACAT |
| PSA2097 | TCCTATTAATTATCTGTTAATCTC | GAATAAAGTCCTCCAAAGTTCTAT |
| PSA2353 | ATCCTCCCAATAATCAAAACACTCT | CTTGATGCACTAAACTTTTGAAATAT |

The compounds and methods of the appended claims are not limited in scope by the specific compounds and methods combination of steps, elements, components, or constituents can be explicitly mentioned herein; however, all other combinations of steps, elements, components, and constituents are included, even though not explicitly stated.

What is claimed is:

1. A method of treating a bacterial infection in a subject, the method comprising administering to the subject a therapeutically effective amount of a cephalosporin and a Ser/Thr protein kinase (STK1) inhibitor defined by Formula IA

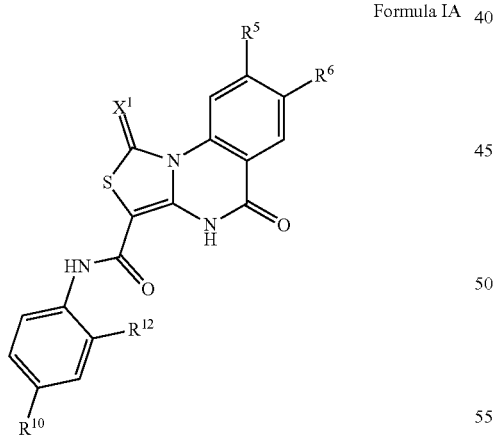

Formula IA wherein
$R^5$ is $C(O)OR^{a1}$, $R^6$ is H, and $R^{a1}$ is selected from $C_{1-6}$ alkyl and $C_{1-4}$ haloalkyl, or wherein $R^5$ is H, $R^6$ is $C(O)OR^{a1}$, and $R^{a1}$ is selected from $C_{1-6}$ alkyl and $C_{1-4}$ haloalkyl;
$X^1$ is selected from the group consisting of S and O;
$R^{10}$ and $R^{12}$ are each independently selected from the group consisting of H, halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)$ $NR^c$-$R^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR'S(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkyl sulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or a pharmaceutically acceptable salt, ester, or N-oxide thereof.

2. The method of claim 1, wherein $R^{12}$ is selected from $C_{1-6}$ alkyl, $C_{1-4}$ haloalkyl, $C_{1-6}$ alkoxy, or $C_{1-6}$ haloalkoxy.

3. The method of claim 1, wherein $R^{12}$ is halo.

4. The method of claim 1, wherein $R^{10}$ is selected from $C_{1-6}$ alkyl, $C_{1-4}$ haloalkyl, $C_{1-6}$ alkoxy, $C_{1-6}$ haloalkoxy, or halo.

5. The method of claim 1, wherein the STK1 inhibitor is Inh2-B1 (methyl 5-oxo-3-(phenyl carbamoyl)-1-thioxo-4,5dihydro[1,3]thiazolo[3,4-a]quinazoline-8-carboxylate) or a salt, ester, or N-oxide thereof.

6. The method of claim 1, wherein the cephalosporin is a third generation cephalosporin.

7. The method of claim 1, wherein the bacterial infection is a *Staphylococcus aureus* infection.

8. The method of claim 1, wherein the cephalosporin and the STK1 inhibitor are administered to the subject simultaneously.

9. The method of inhibiting Ser/Thr protein kinase (STK1) in a bacterial cell, the method comprising contacting the bacterial cell with a Ser/Thr protein kinase (STK1) inhibitor defined by Formula IA

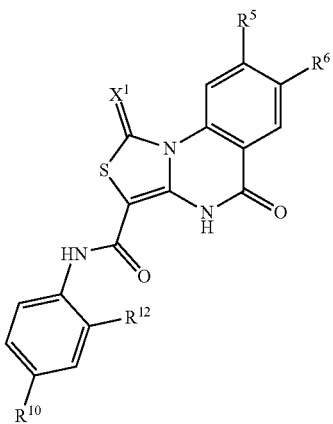

Formula IA wherein $R^5$ is C(O)O$R^{a1}$, $R^6$ is H, and $R^{a1}$ is selected from $C_{1-6}$ alkyl and $C_{1-4}$ haloalkyl, or wherein $R^5$ is H, $R^6$ is C(O)O$R^{a1}$, and $R^{a1}$ is selected from $C_{1-6}$ alkyl and $C_{1-4}$ haloalkyl;

$X^1$ is selected from the group consisting of S and O;

$R^{10}$ and $R^{12}$ are each independently selected from the group consisting of H, halo, $C_{1-6}$ alkyl, $C_{2-6}$ alkenyl, $C_{2-6}$ alkynyl, $C_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR'S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^B$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^B$ groups;

each $R^e$ is independently selected from H, CN, $C_{1-6}$ alkyl, $C_{1-6}$ haloalkyl, $C_{1-6}$ alkylthio, $C_{1-6}$ alkyl sulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^B$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$alkyl) aminosulfonylamino, aminocarbonylamino, $C_{1-6}$ alkylaminocarbonylamino, and di($C_{1-6}$alkyl)aminocarbonylamino;

or a pharmaceutically acceptable salt, ester, or N-oxide thereof.

10. The method of claim 1, wherein the cephalosporin is ceftriaxone.

11. The method of claim 1, wherein the cephalosporin is cefotaxime.

12. The method of claim 1, wherein the bacterial infection is a methicillin-resistant *Staphylococcus aureus* infection.

\* \* \* \* \*

UNITED STATES PATENT AND TRADEMARK OFFICE
CERTIFICATE OF CORRECTION

PATENT NO. : 11,318,141 B2
APPLICATION NO. : 16/627575
DATED : May 3, 2022
INVENTOR(S) : Vijay Pancholi It is certified that error appears in the above-identified patent and that said Letters Patent is hereby corrected as shown below:

In the Claims

Claim 1, Column 72, Line 33 reading:
$NR^c\text{-}R^d$, $NR^cR^d$, $NR^cOR^d$, $NR^cC(O)R^b$, $NR^cC(O)OR^a$, Should read:
$NR^cR^d$, $NR^cR^d$, $NR^cOR^d$, $NR^cC(O)R^b$, $NR^cC(O)OR^a$, Claim 1, Column 72, Line 35 reading:
$NR^cC(=NR^e)NR^cR^d$, $NR'S(O)R^b$, $NR^cS(O)_2R^b$, Should read:
$NR^cC(=NR^e)NR^cR^d$, $NR^cS(O)R^b$, $NR^cS(O)_2R^b$, Claim 9, Column 74, Line 8 reading:
$NR^cC(=NR^e)NR^cR^d$, $NR'S(O)R^b$, $NR^cS(O)_2R^b$, Should read:
$NR^cC(=NR^e)NR^cR^d$, $NR^cS(O)R^b$, $NR^cS(O)_2R^b$, Signed and Sealed this
Twenty-ninth Day of November, 2022

Katherine Kelly Vidal
*Director of the United States Patent and Trademark Office*